United States Patent
Mansour et al.

(10) Patent No.: US 10,022,441 B2
(45) Date of Patent: Jul. 17, 2018

(54) METHOD FOR IMPROVING THE EFFICACY OF A SURVIVIN VACCINE IN THE TREATMENT OF CANCER

(71) Applicant: IMMUNOVACCINE TECHNOLOGIES, INC., Halifax, Nova Scotia (CA)

(72) Inventors: Marc Mansour, Halifax (CA); Neil L. Berinstein, Toronto (CA); Genevieve Mary Weir, Dartmouth (CA); Marianne M. Stanford, Dartmouth (CA)

(73) Assignee: Immunovaccine Technologies, Inc., Halifax, Nova Scotia (CA)

( * ) Notice: Subject to any disclaimer, the term of this patent is extended or adjusted under 35 U.S.C. 154(b) by 21 days.

(21) Appl. No.: 14/778,897

(22) PCT Filed: Mar. 27, 2013

(86) PCT No.: PCT/CA2013/050248
§ 371 (c)(1),
(2) Date: Sep. 21, 2015

(87) PCT Pub. No.: WO2014/153636
PCT Pub. Date: Oct. 2, 2014

(65) Prior Publication Data
US 2016/0067335 A1 Mar. 10, 2016

(51) Int. Cl.
*A61K 39/39* (2006.01)
*A61K 31/675* (2006.01)
*A61K 39/00* (2006.01)
*A61K 9/127* (2006.01)
*A61K 39/05* (2006.01)

(52) U.S. Cl.
CPC ............. *A61K 39/39* (2013.01); *A61K 9/127* (2013.01); *A61K 31/675* (2013.01); *A61K 39/0011* (2013.01); *A61K 39/05* (2013.01); *A61K 2039/545* (2013.01); *A61K 2039/55511* (2013.01); *A61K 2039/55555* (2013.01); *A61K 2039/55561* (2013.01); *A61K 2039/55566* (2013.01); *A61K 2039/6037* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 4,722,848 A | 2/1988 | Paoletti et al. | |
| 5,580,859 A | 12/1996 | Felgner et al. | |
| 5,589,466 A | 12/1996 | Felgner et al. | |
| 5,679,647 A | 10/1997 | Carson et al. | |
| 5,736,524 A | 4/1998 | Content et al. | |
| 5,739,118 A | 4/1998 | Carrano et al. | |
| 5,804,566 A | 9/1998 | Carson et al. | |
| 5,922,687 A | 7/1999 | Mann et al. | |
| RE37,224 E | 6/2001 | Brown et al. | |
| 6,245,523 B1 | 6/2001 | Altieri | |
| 6,793,923 B2 | 9/2004 | Brown et al. | |
| 7,824,686 B2 | 11/2010 | Brown et al. | |
| 8,628,937 B2 | 1/2014 | Brown et al. | |
| 9,114,174 B2 | 8/2015 | Brown et al. | |
| 2006/0051354 A1* | 3/2006 | Simard | A61K 39/0011 424/178.1 |
| 2008/0233143 A1 | 9/2008 | Jackson et al. | |
| 2009/0297593 A1 | 12/2009 | Daftarian et al. | |
| 2010/0129385 A1 | 5/2010 | Jackson et al. | |
| 2010/0203116 A1 | 8/2010 | Mansour et al. | |
| 2010/0209452 A1 | 8/2010 | Mansour et al. | |
| 2011/0070298 A1 | 3/2011 | Mansour et al. | |
| 2011/0091489 A1* | 4/2011 | Andersen | A61K 39/0011 424/185.1 |
| 2011/0200632 A1 | 8/2011 | Jackson et al. | |
| 2014/0234404 A1 | 8/2014 | Mansour et al. | |
| 2015/0202152 A1 | 7/2015 | Daftarian et al. | |

FOREIGN PATENT DOCUMENTS

| | | |
|---|---|---|
| CN | 1767848 | 5/2006 |
| WO | WO 1998/004720 | 2/1998 |
| WO | WO 2002/038175 A1 | 5/2002 |
| WO | 2004067023 | 8/2004 |
| WO | WO 2004/067023 | 8/2004 |
| WO | WO 2006/081826 | 8/2006 |
| WO | WO 2007/041832 A1 | 4/2007 |
| WO | WO 2009/039628 A1 | 9/2008 |
| WO | WO 2009/043165 | 4/2009 |
| WO | WO 2009/146523 A1 | 12/2009 |
| WO | WO 2013/049941 A1 | 4/2013 |

OTHER PUBLICATIONS

Wobser et al. (Cancer Immunol. Immunother., 55: 1294-1298, 2006).*
Colleoni et al. (Annals of Oncology, 17: 232-238, 2006).*
Machiels et al. (Cancer Research, 61: 3689-3697, 2001).*
Alonso MJ et al, Biodegradable microspheres as controlled-release tetanus toxoid delivery systems, Vaccine, Mar. 1994, 299-306, 12(4).
Altieri DC et al, Survivin apoptosis: an interloper between cell death and cell proliferation in cancer, Lab Invest, Nov. 1998, 1327-1333, 79(11).
Altschul SF et al, Basic local alignment search tool, J Mol Biol, Oct. 5, 1990, 403-410, 215(3).

(Continued)

*Primary Examiner* — Nelson B Moseley, II
(74) *Attorney, Agent, or Firm* — Troutman Sanders LLP

(57) ABSTRACT

The present invention provides methods for improving the efficacy of a vaccine in the treatment of cancer. The methods of the invention comprise the administration of at least two doses of an agent that interferes with DNA replication prior to vaccination with a survivin vaccine. Also provided are compositions for use in the methods of the invention.

29 Claims, 7 Drawing Sheets

(56) References Cited

OTHER PUBLICATIONS

Angulo I et al, Nitric oxide-producing CD11b(+)Ly-6G(Gr-1)(+)CD31(ER-MP-12)(+) cells in the spleen of cyclophosphamide-treated mice: implications for T-cell responses in immunosuppressed mice, Blood, 2000, 212-220, 95(1).

Audia S et al, Increase of CD4+ CD25+ regulatory T cells in the peripheral blood of patients with metastatic carcinoma: a Phase I clinical trial using cyclophosphamide and immunotheraphy to eliminate CD4+ CD25+ T lymphocytes, Clin Exp Immunol, Dec. 2007, 523-530, 150(3).

Awwad M et al, Cyclophosphamide (Cy)-facilitated adoptive immunotherapy of a Cy-resistant tumour. Evidence that Cy permits the expression of adoptive T-cell mediated immunity by removing suppressor T cells rather than by reducing tumour burden, Immunology, Sep. 1998, 87-92, 65(1).

Balkwill F et al, B regulatory cells in cancer, Trends Immunol, Apr. 2013, 169-173, 34(4), Elsevier.

Banga AK, Therapeutic Peptides and Proteins, Formulation, Processing and Delivery Systems, 1995, Technomic Publishing Co, Lancaster, Pennsylvania, USA.

Barbon CM et al, Consecutive low doses of cyclophosphamide preferentially target Tregs and potentiate T cell responses induced by DNA PLG microparticle immunization, Cell Immunol, 2010, 150-161, 262(2).

Berinstein NL et al, First-in-man application of a novel therapeutic cancer vaccine formulation with the capacity to induce multi-functional T cell responses in ovarian, breast and prostate cancer patients, J Transl Med, Aug. 3, 2012, 156, 10.

Berzofsky JA et al, Strategies to use immune modulators in therapeutic vaccines against cancer, Semin Oncol, Jun. 2012, 348-357, 39(3), Elsevier.

Bracci LF et al, Cyclophosphamide enhances the antitumor efficacy of adoptively transferred immune cells through the induction of cytokine expression, B-cell and T-cell homeostatic proliferation, and specific tumor infiltration, Clin Cancer Res, 2007, 644-653, 13(2 pt 1).

Browder T et al, Antiangiogenic scheduling of chemotheraphy improves efficacy against experimental drug-resistant cancer, Cancer Res, Apr. 1, 2000, 1878-1886, 60(7).

Bruce WR et al, Comparison of the sensitivity of normal hematopoietic and transplanted lymphoma colony-forming cells to chemotherapeutic agents administered in vivo, J Natl Cancer Inst, 1996, 233-245, 37(2).

Caruthers MH et al, New chemical methods for synthesizing polynucleotides, Nucleic Acids Symp Ser, 1980, 215-223, (7).

Cease KB et al, Toward a vaccine for AIDS: the emergence of immunobiology-based vaccine development, Annu Rev Immunol, 1994, 923-989, 12.

Celis E, Recognition of hepatitis B surface antigen by human T lymphocytes. Proliferative and cytotoxic responses to a major antigenic determinant defined by synthetic peptides, J Immunol, Mar. 15, 1988, 1808-1815, 140(6).

Chakrabarti S et al, Expression of the HTLV-III envelope gene by a recombinant vaccinia virus, Nature, Apr. 10-16, 1986, 535-537, 320(6026).

Chanda PK et al, High level expression of the envelope glycoproteins of the human immunodeficiency virus type I in presence of rev gene using helper-independent adenovirus type 7 recombinants, Virology, Apr. 1990, 535-547, 175(2).

Chong P et al, Identification of T- and B-cell epitopes of the S2 and S3 subunits of pertussis toxin by use of synthetic peptides, Infect Immun, Nov. 1992, 4640-4647, 60(11).

Chu CS et al, Phase I/II randomized trial of dendritic cell vaccination with or without cyclophosphamide for consolidation therapy of advanced ovarian cancer in first or second remission, Cancer Immunol Immunother, May 2012, 629-641, 61(5).

Cohen JL et al, Pharmacokinetics of cyclophosphamide in man, Br J Pharmacol, Nov. 1971, 677-680, 43(3).

Curiel TJ et al, Specific recruitment of regulatory T cells in ovarian carcinoma fosters immune privilege and predicts reduced survival, Nat Med, Sep. 2004, 942-949, 10(9), Nature Publishing Group.

Daftarian PM et al, Rejection of large HPV-16 expressing tumors in aged mice by a single immunization of VacciMax encapsulated CTL/T helper peptides, J Transl Med, Jun. 7, 2007, 26, 5.

De Jonge ME et al, Clinical pharmacokinetics of cyclophosphamide, Clin Pharmacokinet, 2005, 1135-1164, 44(11).

Demotz S et al, Delineation of several DR-restricted tetanus toxin T cell epitopes, J Immunol, Jan. 15, 1989, 394-402, 142(2).

Diethelm-Okita BM et al, Universal epitopes for human CD4+ cells on tetanus and diphtheria toxins, J Infect Dis, Mar. 2000, 1001-1009, 181(3).

D'Incalci M et al, Decreased half life of cyclophosphamide in patients under continual treatment, Eur J Cancer, Jan. 1979, 7-10, 15(1).

Ding ZC et al, Cytotoxic chemotherapy and CD4+ effector T cells: an emerging alliance for durable antitumor effects, Clin Dev Immunol, 2011, 890178.

Eldridge JH et al, Biodegradable microspheres as a vaccine delivery system, Mol Immunol, Mar. 1991, 287-294, 28(3).

Eldridge JH et al, New advances in vaccine delivery systems, Semin Hematol, Oct. 1993, 16-24, 30(4 Suppl 4), discussion 25.

Ellebaek EL et al, Metastatic melanoma patients treated with dendritic cell vaccination, Interleukin-2 and metronomic cyclophosphamide: results from a phase II trial, Cancer Immunol Immunother, 2012, 1791-1804, 61(10).

Emmenegger U et al, Pharmacodynamic and pharmacokinetic study of chronic low-dose metronomic cyclophosphamide therapy in mice, Mol Cancer Ther, Aug. 6, 2007, 2280-2289, 6(8).

Emmenegger U et al, Tumors that acquire resistance to low-dose metronomic cyclophosphamide retain sensitivity to maximum tolerated dose cyclophosphamide, Neoplasia, Jan. 2011, 40-48, 13(1).

Engell-Noerregaard L et al, FDG PET scans as evaluation of clinical response to dendritic cell vaccination in patients with malignant melanoma, Cancer Immunol Immunother, Jan. 2013, 17-25, 62(1).

Falo LD Jr et al, Targeting antigen into the phagocytic pathway in vivo induces protective tumour immunity, Nat Med, Jul. 1995, 649-653, 1(7).

Frezard F, Liposomes: from biophysics to the design of peptide vaccines, Braz J Med Biol Res, Feb. 1999, 181-189, 32(2).

Ghiringhelli F et al, Metronomic cyclophosphamide regimen selectively depletes CD4+CD25+ regulatory T cells and restores T and NK effector functions in end stage cancer patients, Cancer Immunol Immunother, May 2007, 641-648, 56(5).

Gregoriadis G, Immunological adjuvants: a role for liposomes, Immunol Today, Mar. 1990, 89-97, 11(3).

Gupta RK et al, Adjuvants—a balance between toxicity and adjuvanticity, Vaccine, 1993, 293-306, 11(3).

Hanahan D et al, Hallmarks of cancer: the next generation, Cell, Mar. 4, 2011, 646-674, 144(5), Elsevier.

Hermans IF et al, Synergistic effect of metronomic dosing of cyclophosphamide combined with specific antitumor immunotherapy in a murine melanoma model, Cancer Res, Dec. 1, 2003, 8408-8413, 63(23).

Higano CS et al, Integrated data from 2 randomized, double-blind, placebo-controlled, phase 3 trials of active cellular immunotherapy with sipuleucel-T in advanced prostate cancer, Cancer, 2009, 3670-3679, 115(16).

Hu KF et al, The immunostimulating complex (ISCOM) is an efficient mucosal delivery system for respiratory syncytial virus (RSV) envelope antigens inducing high local and systemic antibody responses, Clin Exp Immunol, Aug. 1998, 235-243, 113(2).

Hu SL et al, Expression of AIDS virus envelope gene in recombinant vaccinia viruses, Nature, Apr. 10-16, 1986, 537-40, 320(6062).

Jones DH et al, Protection of mice from Bordetella pertussis respiratory infection using microencapsulated pertussis fimbriae, Vaccine, May 1995, 675-681, 13(7).

Juma FD et al, Pharmacokinetics of cyclophosphamide and alkylating activity in man after intravenous and oral administration, Br J Clin Pharmacol, Sep. 8, 1979, 209-217, 8(3).

Kieny M-P et al, AIDS virus env protein expressed from a recombinant vaccinia virus, Nature Biotechnology, 1986, 790-795, 4.

(56) References Cited

OTHER PUBLICATIONS

Kofler N, Preparation and characterization of poly(D,L-lactide-co-glycolide and poly-(L-lactic acid) microspheres with entrapped pneumotropic bacterial antigens, J Immunol Methods, Jun. 10, 1996, 25-35, 192(1-2).
Le DT et al, Regulatory T-cell modulation using cyclophosphamide in vaccine approaches: a current perspective, Cancer Res, Jul. 15, 2012, 3439-3444, 72(14).
Liu WM et al, The potential beneficial effects of drugs on the immune response to vaccination, Semin Oncol, Jun. 2012, 340-347, 39(3), Elsevier.
Lutsiak ME et al, Inhibition of CD4(+)25(+) T regulatory cell function implicated in enhanced immune response by low does cyclophosphamide, Blood, Apr. 1, 2005, 2862-8, 105(7).
Machiels JP et al, Cyclophosphamide, doxorubicin, and paclitaxel enhance the antitumor response of granulocyte/macrophage-colony stimulating factor-secreting whole-cell vaccines in HER-2/neu tolerized mice, Cancer Res, 2001, 3689-3697, 61(9).
Man S et al, Antitumor effects in mice of low-dose (metronomic) cyclophosphamide administered continuously through the drinking water, Cancer Res, May 15, 2002, 2731-2735, 62(10).
Mansour M et al, Therapy of established B16-F10 melanoma tumors by a single vaccination of CTL/T helper peptides in VacciMax, J Transl Med, Apr. 23, 2007, 20, 5.
Merrifield B, Concept and early development of solid-phase peptide synthesis, Methods Enzymol, 1997, 3-13, 289.
Mikyskova R et al, Cyclophosphamide induced myeloid-derived suppressor cell population is immunosuppressive but not identical to myeloid-derived suppressor cells induced by growing TC-1 tumors, J Immunother, 2012, 374-384, 35(5).
Mouridsen HT et al, The biotransformation of cyclophosphamide in man: analysis of the variation in normal subjects, Acta Pharmacol Toxicol (Copenh), Aug. 1974, 98-106, 35(2).
Moyle PM et al, Self-adjuvanting lipopeptide vaccines, Curr Med Chem, 2008, 506-516, 15(5).
Nagaraj S et al, Tumor escape mechanism governed by myeloid-derived suppressor cells, Cancer Res, Apr. 15, 2008, 2561-2563, 68(8), American Association for Cancer Research.
Needleman SB et al, A general method applicable to the search for similarities in the amino acid sequence of two proteins, J Mol Biol, Mar. 1970, 443-453, 48(3).
North RJ, Cyclophosphamide-facilitated adoptive immunotherapy of an established tumor depends on elimination of tumor-induced suppressor T cells, J Exp Med, Apr. 1, 1982, 1063-1074, 155(4).
Pearson WR et al, Improved tools for biological sequence comparison, Proc Natl Acad Sci USA, 1988, 2444-2448, 85(5).
Peng S et al, Low-dose cyclophosphamide administered as daily or single dose enhances the antitumor effects of a therapeutic HPV vaccine, Cancer Immunol Immunother, Jan. 2013 (Epub Aug. 4, 2012), 171-182, 62(1).
Radojcic V et al, Cyclophosphamide resets dendritic cell homeostasis and enhances antitumor immunity through effects that extend beyond regulatory T cell elimination, Cancer Immunol Immunother, Jan. 2010 (Epub Jul. 10, 2009), 137-148, 59(1).
Reagan-Shaw S et al, Dose translation from animal to human studies revisited, FASEB J, Mar. 2008, 659-661, 22(3).
Reddy R et al, In vivo cytotoxic T lymphocyte induction with soluble proteins administered in liposomes, J Immunol, Mar. 1, 1992, 1585-1589, 148(5).
Roberge JY et al, A strategy for a convergent synthesis of N-linked glycopeptides on a solid support, Science, Jul. 14, 1995, 202-204, 269(5221).
Robinson HL et al, Protection against a lethal influenza virus challenge by immunization with a haemagglutinin-expressing plasmid DNA, Vaccine, 1993, 957-960, 11(9).
Rock KL, A new foreign policy: MHC class I molecules monitor the outside world, Immunol Today, Mar. 1996, 131-137, 17(3).
Salem ML et al, Defining the ability of cyclophosphamide preconditioning to enhance the antigen-specific CD8+ T-cell response to peptide vaccination: creation of a beneficial host microenvironment involving type I IFNs and myeloid cells, J Immunother, Jan. 2007, 40-53, 30(1).
Salem ML et al, Kinetics of rebounding of lymphoid and myeloid cells in mouse peripheral blood, spleen and bone marrow after treatment with cyclophosphamide, Cell Immunol, Mar.-Apr. 2012, 67-74, 276(1-2).
Schiavoni G et al, Cyclophosphamide induces type I interferon and auments the number of CD44(hi) T lymphocytes in mice: implications for strategies of chemoimmunotherapy of cancer, Blood, Mar. 15, 2000, 2024-2030, 95(6).
Sistigu A et al, Immunomodulatory effects of cyclophosphamide and implementations for vaccine design, Semin Immunopathol, Jul. 2011, 369-383, 33(4).
Slingluff CL Jr et al, Phase I trial of a melanoma vaccine with gp100(280-288) peptide and tetanus helper peptide in adjuvant: immunologic and clinical outcomes, Clin Cancer Res, Oct. 2001, 3012-3024, 7(10).
Slingluff CL Jr et al, Randomized multicenter trial of the effects of melanoma-associated helper peptides and cyclophosphamide on the immunogenicity of a multipeptide melanoma vaccine, J Clin Oncol, Jul. 20, 2011, 2924-2932, 29(21).
Smith PC et al, Sensitivity of murine B- and T-lymphocytes to oxazaphosphorine and non-oxazaphosphorine nitrogen mustards, Biochem Pharmacol, Oct. 1, 1985, 3459-3463, 34(19).
Smith TF et al, Comparison of biosequences, Adv Appl Math, 1981, 428-489, 2(4).
So et al, Vigorous response of human innate functioning IgM memory B cells upon infection by Neisseria gonorrhoeae, J Immunol, Apr. 15, 2012, 4008-4022, 188(8).
Stover CK et al, New use of BCG for recombinant vaccines, Nature, Jun. 6, 1991, 456-460, 351(6326).
Taieb J et al, Chemoimmunotherapy of tumors: cyclophosphamide synergizes with exosome based vaccines, J Immunol, Mar. 1, 2006, 2722-2729, 176(5).
Takahashi H et al, Induction of CD8+ cytotoxic T cells by immunization with purified HIV-1 envelope protein in ISCOMs, Nature, Apr. 26, 1990, 873-875, 344(6269).
Tam JP, Recent advances in multiple antigen peptides, Sep. 13, 1996, 17-32, 196(1).
Tam JP, Synthetic peptide vaccine design: synthesis and properties of a high-density multiple antigenic peptide system, Proc Natl Acad Sci USA, Aug. 1988 5409-13, 85(15).
Tongu M et al, Metronomic chemotherapy with low-dose cyclophosphamide plus gemcitabine can induce anti-tumor T cell immunity in vivo, Cancer Immunol Immunother, 2012, 383-391, 62(2).
Top FH Jr, Immunization with live types 7 and 4 adenovirus vaccines. I. Safety, infectivity, antigenicity, and potency of adenovirus type 7 vaccine in humans, J Infect Dis, Aug. 1971, 148-154, 124(2).
Ugel S et al, Immune tolerance to tumor antigens occurs in a specialized environment of the spleen, Cell Rep, 2012, 628-639, 2(3).
Ulmer JB et al, Heterologous protection against influenza by injection of DNA encoding a viral protein, Science, Mar. 19, 1993, 1745-1749, 259(5102).
Veltman JD et al, Low-dose cyclophosphamide synergizes with dendritic cell-based immunotherapy in antitumor activity, J Biomed Biotechnol, 2010, 798467.
Vermeij R et al, Potentiation of a p53-SLP vaccine by cyclophosphamide in ovarian cancer: a single-arm phase II study, Int J Cancer, Sep. 1, 2012, E670-E680, 131(5), UICC.
Vitiello A et al, Development of a lipopeptide-based therapeutic vaccine to treat chronic HBV infection. I. Induction of a primary cytotoxic T lymphocyte response in humans, J Clin Invest, Jan. 1995, 341-349, 95(1).
Voelcker G et al, Pharmacokinetics of "activated" cyclophosphamide and therapeutic efficacies, Cancer, Sep. 15, 1984, 1179-1186, 54(6 Suppl).
Wada S et al, Cyclophosphamide augments antitumor immunity: studies in an autochtonous prostate cancer model, Cancer Res, May 15, 2009, 4309-4318, 69(10).

(56) References Cited

OTHER PUBLICATIONS

Walter S et al, Multipeptide immune response to cancer vaccine IMA901 after single-dose cyclophosphamide associates with longer patient survival, Aug. 2012, 1254-1261, 18(8).
Warren HS et al, Current status of immunological adjuvants, Annu Rev Immunol, 1986, 396-88, 4.
Weir GM et al, Immune modulation by chemotherapy or immunotherapy to enhance cancer vaccines, Cancers (Basel.), Aug. 5, 2011, 3114-3142, 3(3), MDPI AG, Basel (Switzerland).
Wolff JA et al, Direct gene transfer into mouse muscle in vivo, Science, Mar. 23, 1990, 1465-1468, 247(4949 Pt 1).
Wonderlich J et al, Induction and measurement of cytotoxic T lymphocyte activity, Curr Protoc Immunol, 2006, Chapter 3, Unit 3.11.
Yang L et al, TGF-beta and immune cells: an important regulatory axis in the tumor microenvironment and progression, Trends Immunol, Jun. 2010, 220-227, 31(6), Elsevier.
Yong X et al, Strategies for enhancing vaccine-induced CTL anti-tumor immune responses, J Biomed Biotechnol, 2012, 605054 (Epub).
Zhang J et al, Metabolism and transport of oxazaphosporines and the clinical implications, Drug Metab Rev, 2005, 27(4), 611-703, 37(4).
Zhao J et al, Selective depletion of CD4+CD25+Foxp3+ regulatory T cells by low-dose cyclophosphamide is explained by reduced intracellular ATP levels, Cancer Res, Jun. 15, 2010, 4850-4858, 70(12).
Zitvogel et al, Immunological aspects of cancer chemotherapy, Nat Rev Immunol, Jan. 2008, 59-73, 8(1), Nature Publishing Group.
International Search Report and Written Opinion for PCT/CA2013/050248.
Weir, G. et al. "Immune Modulation and Treg Suppression with Metrononic Cyclophosphamide Enhances the Antitumor Effect of a Therapeutic peptide vaccine in a murine model." Amer Assoc for Cancer Res, Proceedings of the 103rd Annual Meeting of the Amer Assoc for Cancer Res., (2012 Abs No. 4405).
Emens, L.A. et al. "Timed Sequential Treatmand with Cyclophosphamide, Doxorubicin, and an Allogeneic Granulocyte-Macrophage Colony-Stimulating Factor-Secreting Breast Tumor Vaccine: A Chemotherapy Dose-Ranging Factorial Study of Safety and Immune Activation." Journ. of Clin. Onc. (2009) vol. 27(35), pp. 5911-5918.
Berd, D. et al. "Induction of Cell-Mediated Immunity to Autologous Melanoma Cells and Regresson of Metastases after Treatment with a Melanoma Cell Vaccine Preceded by Cyclophosphamide." Cancer Res. (1986) vol. 46, pp. 2572-2577.
Karkada M. et al., "A Novel Breast/Ovarian Cancer Peptide Vaccine Platform That Promotes Specific Type-1 but not Treg/Tr1-type Responses." Journal of Immun (2010, vol. 33, pp. 250-261.
Fi Lipazzi Paola et al: "Limited Induction of Tumor Cross-Reactive T Cells without a Measurable Clinical Benefit in Early Melanoma Patients Vaccinated with Human Leukocyte Anti gen Class I-Modified Peptides", Clinical Cancer Research, vol. 18, No. 23, Dec. 1, 2012 (Dec. 1, 2012) , pp. 6485-6496, XP002761373.
Filipazzi P, et al .: "Supplementary Figure 1: Limited Induction of Tumor-cross-reactive T Cells without a Measurable Clinical Benefit in Early Melanoma Patients Vaccinated with Human Leukocyte Anti gen-Class I-Modified Peptides" , Clinical Cancer Research Dec. 1, 2012 (Dec. 1, 2012), XP002761465, (1 pg.).
Lotte Engell-Noerregaard: "Influence of metronomic cyclophosphamide and Interleukine-2 alone or combined on blood regulatory T cells in patients with advanced malignant melanoma treated with dendritic cell vaccines", J. Clinical & Cellula Immunology,vol. 3, No. 1 Mar. 10, 2012 (Mar. 10, 2012), pp. 1-8, XP002761374.
Engell-Noerregaard Lotte et al: "Dendritic Cells Transfected with mRNA for p53, Survivin and hTERT as Treatment for Patients With Malignant Melanoma or Breast Cancer—A Phase I Study", Journal of Immunotherapy; 25th Annual Scientific Meeting of the International Society for Biological Therapy of Cancer, Lippincott Williams & Wilkings Inc, US; Washington, DC, USA vol. 33; No. 8 Oct. 1 2(:)1(:) (Oct. 2010-(:)1). p. 876, XP008181393.
Engell-Noerregaard Lotte et al: "Combined Treatment with Dendritic Cell Vaccine and Low-Dose Cyclophosphamide in Patients with Malignant Melanoma", Journal of Immunotherapy; 25th Annual Scientific Meeting of the International Society for Biological Therapy of Cancer, Lippincott Williams & Wilkings Inc, US; Washington, DC, USA vol. 33, No. 8 Oct. 1, 2010 (Oct. 1, 2010), pp. 876-877.XP008181394.
Riedmann Eva M: "Ovarian cancer vaccine candidate DPX-Survivac: positive interim results from phase 111", Human Vaccines & Immunotherapeutics, Taylor & Franci s, US, vol. 8, No. 12, Dec. 1, 2012 (Dec. 1, 2012), p. 1743, XP008181391.
Ellebaek Eva et al: "Metastatic melanoma patients treated with dendriti c cell vaccination, Interleukin-2 and metronomic cyclophosphamide: results from a phase II trial", Cancer Immunology Immunotherapy, vol. 61, No. 10, Oct. 2012 (Oct. 2012), pp. 1791-1804, XP035115266.
Genevieve Weir et al: "Immune modulation and Treg suppression with metronomic cyclophosphamide enhances the anti-tumor effect of a therapeutic peptide vaccine in a murine model", American Association for Cancer Research. Proceedings of the Annual Meeting, American Association for Cancer Research, US, vol. 103, Apr. 3, 2012 (Apr. 3, 2012). XP008180946 (3 pgs.).
Supplemental European Search Report related to EP 13 88 0361, dated Sep. 1, 2016 (9 pgs.).
Bystryn, et al., "Immunogenicity of a Polyvalent Melanoma Antigen Vaccine in Humans," Cancer 61:1065-1070, Mar. 15, 1988.
Oratz, et al., "Lack of Effect of Cyclophosphamide on the Immunogenicity of a Melanoma Antigen Vaccine," Cancer Research 51: 3643-3647, Jul. 15, 1991.
Office Action regarding related Japanese patent application No. 2016-504427, dated Mar. 7, 2017 (3pgs).
English translation of Office Action regarding related Japanese patent application No. 2016-504427, dated Mar. 7, 2017 (3pgs).
Fujisawa et al., "IL-13 Mediates Invasion and Metastasis Through IL-13Rx2 VIA ERK/AP-I Pathway In Vivo Mouse Model of Human Ovarian Cancer," J. Immunother, vol. 34, No. 9, Nov.-Dec. 2011 pp. 1703 (2 pgs).
Fillipazzi et al., "Limited Induction of Tumor Cross-Reactive T Cells without a Measurable Clinical Benefit in Early Melanoma Patients Vaccinated with Human Leukocyte Antigen Class I-Modified," Clin Cancer Res; 18(23) Dec. 1, 2012 pp. 6485-6496 (22 pgs.)
Engell-Noerregaard et al., "Influence of Metronomic Cyclophoshamide and Interleukine-2 alone or combined on Blood Regulatory T Cells in Patients with Advanced Malignant Melanoma Treated with Dendritic Cell Vaccines," J. Clin Cell Immunol 2012 3:1 (8 pgs.).
de Veer et al., "Cell Recruitment and Antigen Trafficking in Afferent Lymph After Injection of Antigen and poly(I:C) Containing Liposomes, in Aqueous or Oil-Based Formulations," Vaccine 31 (2013) pp. 1012-1018.
Colleoni et al., "Metronomic low-dose oral cyclophosphamide and methotrexate plus or minus thalidomide in metastatic breast cancer: antitumor activity and biological effects," Annals of Oncology 17: 232-238, 2006 doi:10.1093/annonc/mdj066 Published online Dec. 1, 2005 (7 pgs.).
Office Action related to related Chinese application 2013800769243.

\* cited by examiner

SEQUENCE LISTING

```
<160> NUMBER OF SEQ ID NOS: 14

<210> SEQ ID NO 1
<211> LENGTH: 9
<212> TYPE: PRT
<213> ORGANISM: Synthetic peptide
<220> FEATURE:
<223> OTHER INFORMATION: Survivin peptide SurA1
<220> FEATURE:
<221> NAME/KEY: misc_feature
<222> LOCATION: (1)..(9)
<223> OTHER INFORMATION: survivin93-101

<400> SEQUENCE: 1

Phe Glu Glu Leu Thr Leu Gly Glu Phe
1               5

<210> SEQ ID NO 2
<211> LENGTH: 9
<212> TYPE: PRT
<213> ORGANISM: Synthetic peptide
<220> FEATURE:
<223> OTHER INFORMATION: Modified survivin peptide SurA1.T

<400> SEQUENCE: 2

Phe Thr Glu Leu Thr Leu Gly Glu Phe
1               5

<210> SEQ ID NO 3
<211> LENGTH: 9
<212> TYPE: PRT
<213> ORGANISM: Synthetic peptide
<220> FEATURE:
<223> OTHER INFORMATION: Survivin peptide SurA2
<220> FEATURE:
<221> NAME/KEY: misc_feature
<222> LOCATION: (1)..(9)
<223> OTHER INFORMATION: survivin96-104

<400> SEQUENCE: 3

Leu Thr Leu Gly Glu Phe Leu Lys Leu
1               5

<210> SEQ ID NO 4
<211> LENGTH: 9
<212> TYPE: PRT
<213> ORGANISM: Synthetic peptide
<220> FEATURE:
<223> OTHER INFORMATION: Modified survivin peptide SurA2.M

<400> SEQUENCE: 4

Leu Met Leu Gly Glu Phe Leu Lys Leu
1               5
```

```
<210> SEQ ID NO 5
<211> LENGTH: 10
<212> TYPE: PRT
<213> ORGANISM: Synthetic peptide
<220> FEATURE:
<223> OTHER INFORMATION: Survivin peptide SurA3
<220> FEATURE:
<221> NAME/KEY: misc_feature
<222> LOCATION: (1)..(10)
<223> OTHER INFORMATION: survivin18-27

<400> SEQUENCE: 5

Arg Ile Ser Thr Phe Lys Asn Trp Pro Phe
1               5                   10

<210> SEQ ID NO 6
<211> LENGTH: 10
<212> TYPE: PRT
<213> ORGANISM: Synthetic peptide
<220> FEATURE:
<223> OTHER INFORMATION: Modified survivin peptide SurA3.K

<400> SEQUENCE: 6

Arg Ile Ser Thr Phe Lys Asn Trp Pro Lys
1               5                   10

<210> SEQ ID NO 7
<211> LENGTH: 9
<212> TYPE: PRT
<213> ORGANISM: Synthetic peptide
<220> FEATURE:
<223> OTHER INFORMATION: Survivin peptide SurA24
<220> FEATURE:
<221> NAME/KEY: misc_feature
<222> LOCATION: (1)..(9)
<223> OTHER INFORMATION: survivin20-28

<400> SEQUENCE: 7

Ser Thr Phe Lys Asn Trp Pro Phe Leu
1               5

<210> SEQ ID NO 8
<211> LENGTH: 9
<212> TYPE: PRT
<213> ORGANISM: Synthetic peptide
<220> FEATURE:
<223> OTHER INFORMATION: Survivin peptide SurB7
<220> FEATURE:
<221> NAME/KEY: misc_feature
<222> LOCATION: (1)..(9)
<223> OTHER INFORMATION: survivin6-14

<400> SEQUENCE: 8

Leu Pro Pro Ala Trp Gln Pro Phe Leu
1               5

<210> SEQ ID NO 9
<211> LENGTH: 16
<212> TYPE: PRT
<213> ORGANISM: Synthetic peptide
<220> FEATURE:
<223> OTHER INFORMATION: Universal T-helper epitope from tetanus toxoid

<400> SEQUENCE: 9

Ala Gln Tyr Ile Lys Ala Asn Ser Lys Phe Ile Gly Ile Thr Glu Leu
1               5                   10                  15
```

<210> SEQ ID NO 10
<211> LENGTH: 429
<212> TYPE: DNA
<213> ORGANISM: Homo sapiens

<400> SEQUENCE: 10

```
atgggtgccc cgacgttgcc ccctgcctgg cagcccttc tcaaggacca ccgcatctct      60
acattcaaga actggccctt cttggagggc tgcgcctgca ccccggagcg gatggccgag     120
gctggcttca tccactgccc cactgagaac gagcccagact tggcccagtg tttcttctgc   180
ttcaaggagc tggaaggctg ggagccagat gacgacccca tagaggaaca taaaaagcat    240
tcgtccggtt gcgctttcct ttctgtcaag aagcagtttg aagaattaac ccttggtgaa    300
tttttgaaac tggacagaga aagagccaag aacaaaattg caaaggaaac caacaataag    360
aagaaagaat tgaggaaac tgcgaagaaa gtgcgccgtg ccatcgagca gctggctgcc    420
atggattga                                                             429
```

<210> SEQ ID NO 11
<211> LENGTH: 142
<212> TYPE: PRT
<213> ORGANISM: Homo sapiens

<400> SEQUENCE: 11

```
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140
```

<210> SEQ ID NO 12
<211> LENGTH: 13
<212> TYPE: PRT
<213> ORGANISM: Synthetic Peptide
<220> FEATURE:
<223> OTHER INFORMATION: Universal T-helper epitope PADRE (pan-DR epitope)
<220> FEATURE:
<221> NAME/KEY: misc_feature
<222> LOCATION: (3)..(3)
<223> OTHER INFORMATION: Xaa can be any amino acid

<400> SEQUENCE: 12

```
Ala Lys Xaa Val Ala Ala Trp Thr Leu Lys Ala Ala Ala
1               5                   10
```

<210> SEQ ID NO 13
<211> LENGTH: 21

```
<212> TYPE: PRT
<213> ORGANISM: Synthetic Peptide
<220> FEATURE:
<223> OTHER INFORMATION: T-helper epitope, tetanus toxoid peptide F21E

<400> SEQUENCE: 13

Phe Asn Asn Phe Thr Val Ser Phe Trp Leu Arg Val Pro Lys Val Ser
1               5                   10                  15

Ala Ser His Leu Glu
            20

<210> SEQ ID NO 14
<211> LENGTH: 20
<212> TYPE: DNA
<213> ORGANISM: Artificial Sequence
<220> FEATURE:
<223> OTHER INFORMATION: Synthetic CpG oligonucleotide

<400> SEQUENCE: 14
tccatgacgt tcctgacgtt                                            20
```

METHOD FOR IMPROVING THE EFFICACY OF A SURVIVIN VACCINE IN THE TREATMENT OF CANCER

FIELD OF THE INVENTION

The present invention relates generally to methods for treating cancer and, in particular, to methods for improving the efficacy of a survivin vaccine in the treatment of cancer by prior treatment with an agent that interferes with DNA replication.

BACKGROUND OF THE INVENTION

Immune responses induced by vaccination can be categorized broadly into humoral or cellular types. A humoral response is typically desired to protect against viral or bacterial invaders, whereas immunity against virally infected cells and cancer cells typically involves a cell mediated response. Humoral immunity is typified by high levels of antibody production by B cells, whereas cellular immunity is characterized by increased activation of cytotoxic CD8+ T lymphocytes.

Many vaccines that have shown promise in pre-clinical development have ultimately failed to demonstrate clinical benefit when tested in humans. As relates to cancer vaccines, therapeutic intervention is a complex challenge, and many aspects of the disease such as timing of therapy relative to standard of care, stage and type of cancer all have influence on the outcome of treatment. However, there are three features of immunotherapy that may provide better outcome if they are stringently combined: (1) vaccine immunogenicity (i.e. adjuvant); (2) appropriate selection of tumor associated antigens; and (3) ability to overcome tumor induced immune suppression (Weir et al., *Cancer* 3: 3114-3142, 2011; Berzofsky et al., *Semin Oncol* 39(3): 348-357, 2012).

SUMMARY OF THE INVENTION

Applicants have now discovered that the efficacy of a cancer vaccine (i.e. a survivin vaccine) can be improved with the prior administration of at least two doses of an agent that interferes with DNA replication.

Accordingly, in one aspect, the present invention relates to a method for improving the efficacy of a vaccine in the treatment of cancer in a subject, said method comprising: (i) administering to the subject at least two doses of an agent that interferes with DNA replication in an amount sufficient to provide an immune-modulating effect; and (ii) subsequently administering to the subject a therapeutically effective amount of the vaccine, wherein the vaccine comprises at least one survivin antigen.

In an embodiment of the method of the present invention, the agent that interferes with DNA replication is administered to the subject daily for seven consecutive days every fourteen days (i.e. alternating weekly treatment). In an embodiment, this alternating weekly treatment with the agent that interferes with DNA replication begins about one week before the first administration of the survivin vaccine.

In an embodiment of the method of the present invention, the survivin vaccine is administered to the subject once every three weeks.

In an embodiment of the method of the present invention, the agent that interferes with DNA replication is an alkylating agent, such as for example cyclophosphamide.

In an embodiment of the method of the present invention, the survivin vaccine is a vaccine comprising one or more survivin peptide antigens having the amino acid sequence: FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); and LPPAWQPFL (SEQ ID NO: 8).

In an embodiment of the method of the present invention, the survivin vaccine is Immunovaccine, Inc's candidate anti-cancer immunotherapeutic vaccine DPX-Survivac. DPX-Survivac comprises five synthetic survivin peptide antigens having the amino acid sequences: FTELTLGEF (SEQ ID NO: 2), LMLGEFLKL (SEQ ID NO: 4), RISTFKNWPK (SEQ ID NO: 6), STFKNWPFL (SEQ ID NO: 7), and LPPAWQPFL (SEQ ID NO: 8); a universal T-helper epitope from tetanus toxoid (AQYIKANSKFIGITEL; SEQ ID NO: 9); a polyI:C polynucleotide adjuvant; liposomes consisting of DOPC and cholesterol; and the hydrophobic carrier Montanide® ISA 51 VG.

In another aspect, the present invention relates to the use of an agent that interferes with DNA replication in combination with a vaccine comprising at least one survivin antigen for improving the efficacy of the vaccine in the treatment of cancer, wherein at least two doses of the agent are for administration prior to the vaccine.

In another aspect, the present invention relates to a composition for use in a method as described herein.

Other aspects and features of the present invention will become apparent to those of ordinary skill in the art upon review of the following description of specific embodiments of the invention in conjunction with the accompanying figures.

BRIEF DESCRIPTION OF THE FIGURES

In the figures, which illustrate embodiments of the invention by way of example only.

DETAILED DESCRIPTION

Figure 1:
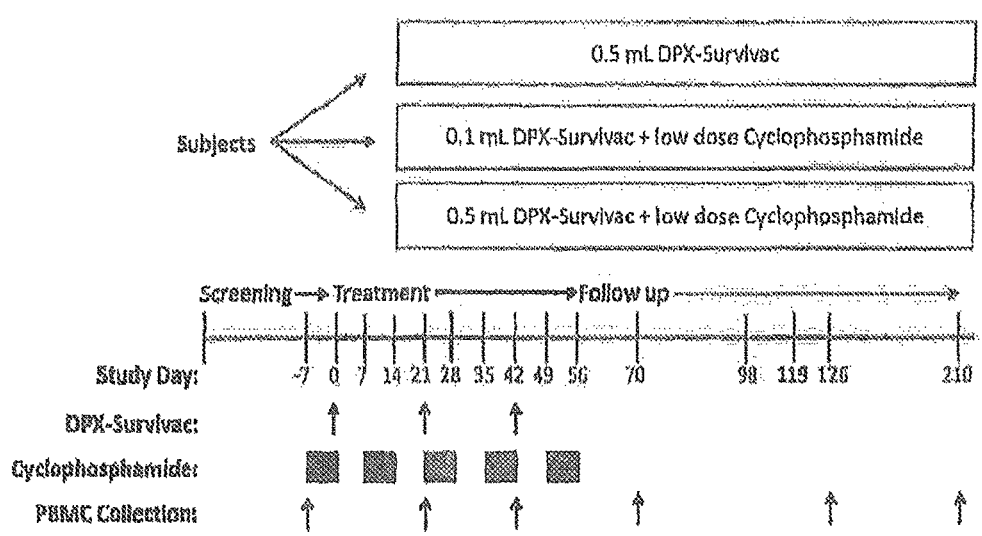
FIG. 1 illustrates a phase I clinical trial design to evaluate the safety and immunogenicity of DPX-Survivac. The vaccine was administered every three weeks (3 vaccinations approximately 21 days apart) with or without oral administration of low dose cyclophosphamide (50 mg twice a day, Baxter) between study days −7 and +49. The low dose cyclophosphamide was given daily for 7 consecutive days every 14 days. Cyclophosphamide was initiated one week before the first vaccination. Patients received either (1) three administrations of 0.5 mL of DPX-Survivac (Cohort A), (2) three administrations of 0.1 mL of DPX-Survivac in combination with low dose oral cyclophosphamide as outlined (Cohort B) or (3) three administrations of 0.5 mL of DPX-Survivac in combination with low dose cyclophosphamide as outlined (Cohort C). Blood samples were collected prior to the first vaccination (baseline) and approximately 3-4 weeks following each vaccination to isolate and cryo-preserve peripheral blood mononuclear cells (PBMC's). Blood samples were also collected at later time points when possible. PBMC's were used for immunological assays including ELISPOT and flow cytometry-based assays such as tetramer staining and intracellular cytokine staining (ICS).

Advanced cancers utilize several mechanisms to escape immune-mediated detection and destruction thus reducing the effectiveness of cancer therapeutics on multiple levels.

Tumor induced immune suppression is one of the hallmarks of cancer and a significant hurdle to any immunotherapy for cancer, including peptide vaccines (Hanahan and Weinberg, Cell, 144(5): 646-674, 2011). As they develop, tumors adapt to avoid and escape immune detection through several mechanisms. The tumor microenvironment, for example, upregulates many factors that promote the development of suppressive immune cells, such as CD4+FoxP3+ regulatory T cells (Tregs) (Curiel et al., Nat Med 10(9): 942-949, 2004) and myeloid-derived suppressor cells (MDSCs) (Nagaraj and Gabrilovich, Cancer Res 68(8): 2561-3, 2008). The tumor microenvironment also contributes to the direct suppression of activated CD8+ T cells by releasing immunosuppressive cytokines such as TNF-β (Yang et al., Trends Immunol 31(6): 220-227, 2010). Other tumor escape mechanisms that respond to immune pressure are immuno-editing, downregulation of MHC class I and alterations in antigen processing and presentation. Therefore, it is imperative that vaccine-induced CD8+ T cells have the opportunity to quickly recognize and destroy tumor cells before they have a chance to adapt. The use of immune modulating agents to counteract tumor induced immune suppression could improve the efficacy cancer vaccines (Yong et al., J Biomed Biotechnol 2012: 605045).

The methods of the present invention relate to the treatment of cancer in a subject by combined administration of an agent that interferes with DNA replication and a survivin vaccine.

Survivin, a protein involved in the negative regulation of apoptosis, is highly expressed in many tumor types and has reported prognostic value. As used herein, "survivin vaccine" is intended to encompass any vaccine or antigen delivery means for administering one or more of the survivin antigens described herein to a subject. Exemplary embodiments of such "survivin vaccines" are described herein; however, the skilled person will appreciate that any vaccine or means for delivering antigens to a subject is encompassed.

Embodiments of the methods of the present invention relate to improving the efficacy of a vaccine (i.e. survivin vaccine) in the treatment of cancer by prior administration of at least two doses of an agent that interferes with DNA replication.

In a particular embodiment therefore, the invention relates to a method for improving the efficacy of a vaccine in the treatment of cancer in a subject, said method comprising: (i) administering to the subject at least two doses of an agent that interferes with DNA replication in an amount sufficient to provide an immune-modulating effect; and (ii) subsequently administering to the subject a therapeutically effective amount of the vaccine, wherein the vaccine comprises at least one survivin antigen.

As used herein, "improving vaccine efficacy" or "improving the efficacy of a vaccine" or the like refers to any change or alteration in the immune response of a subject that is capable of rendering the survivin vaccine of the invention more effective in the treatment of cancer. In some embodiments, this may involve accelerating the appearance of an immune response and/or improving the persistence or strength of an immune response to the survivin vaccine. The immune response may either be a cell-mediated immune response or a humoral immune response.

In the methods of the invention, an agent that interferes with DNA replication may "improve the efficacy of the vaccine" by either directly or indirectly enhancing the immune response against the survivin antigen in the vaccine. This may be accomplished, for example, by reducing the number and/or activity of suppressive immune cells. It has been reported that the tumor microenvironment, for example, upregulates many factors that promote the development of suppressive immune cells, such as CD4+FoxP3+ regulatory T cells (Tregs) (Curiel et al., Nat Med 10(9): 942-949, 2004), myeloid-derived suppressor cells (MDSCs) (Nagaraj and Gabrilovich, Cancer Res 68(8): 2561-3, 2008), and CD19+CD5+CD1d$^{hi}$IL-10+ B cells (Bregs) (Balkwill et al., Trends Immunol, 3 Dec. 2012, 10.1016/j.it.2012.10.007

(Epub ahead of print)). Therefore, the ability to reduce the number or activity of these suppressive immune cells represents an embodiment for improving vaccine efficacy.

"Improving the efficacy of a vaccine" may also be accomplished, for example, by increasing the number and/or activity of antigen-specific CD8+ T cells. In this regard, it has been reported that the tumor microenvironment, for example, contributes to the direct suppression of activated CD8+ T cells by releasing immunosuppressive cytokines such as TNF-13 (Yang et al., Trends Immunol 31(6): 220-227, 2010). Therefore, the ability to increase the activity of antigen-specific CD8+ T cells represents a potential mechanism of improving vaccine efficacy. An increase in antigen-specific CD8+ T cells may be the result of an increased number of such cells, increased activity or such cells, and/or the generation of an enriched population of antigen-specific CD8+ T cells relative to total CD8+ T cells, such as for example by a relative decrease in total CD8+ T cells.

More generally, "improving the efficacy of a vaccine" refers to the ability of the methods of the invention to enhance the immunogenicity of the vaccine, either by enhancing a cell-mediated immune response or a humoral immune response induced by the vaccine; increase the number of immune cells at a site of vaccination or a tumor site; or improve a therapeutic effect provided by the vaccine of the invention, such as by enhancing the prophylactic and/or therapeutic treatment of cancer and/or alleviating, delaying or inhibiting the progression of disease symptoms. Improving the efficacy of a vaccine may also be associated with an improved quality of life or a decreased morbidity, as compared with monotherapy treatment.

"Improving the efficacy of a vaccine" may also mean that lower doses of the active ingredients of the combination of the invention are needed to produce the desired result. This encompasses both embodiments where the dosages themselves are smaller and embodiments where the vaccine, and/or the agent that interferes with DNA replication, are applied less frequently.

Several chemotherapeutics have demonstrated immune modulatory activity when used at low, non-cytotoxic doses (Zitvogel et al., Nat Rev Immunol 8(1): 59-73, 2008; Liu and Dalgleish, Semin Oncol 39(3): 340-347, 2012). Cyclophosphamide was one of the first immune modulatory agents described and has multiple effects on the immune system when used at a fraction of the dose commonly used for its cytotoxic effects (Sistigu et al., Semin Immunopathol 33(4): 369-383, 2011). Low dose cyclophosphamide has been reported to selectively reduce and impair functionality of Tregs (Lutsiak et al., Blood 105(7):2862-2868, 2005), inhibit tumor angiogenesis (Browder et al., Cancer Res 60(7):1878-1886, 2000), increase activation of dendritic cells (Radojcic et al., Cancer Immunol Immunother 59(1): 137-148, 2009) and skew immune response towards Th1 (Schiavoni et al., Blood 95(6):2024-2030, 2000). In mice, the effects of a single bolus low dose administration of cyclophosphamide are transient, typically reaching nadir within 4 days after administration and returning to normal by 7-10 days (Lutsiak et al., Blood 105(7):2862-2868, 2005).

When used in combination with cancer vaccines, low dose cyclophosphamide is typically administered as a single bolus IV injection of around 100-300 mg/m$^2$ in humans (in contrast to the chemotherapeutic dose of 1-5 g/m$^2$) one to three days prior to vaccination (Audia et al., Clin Exp Immunol 150(3):523-530, 2007; Vermeij et al., Int J Cancer 131(5): E670-680, 2012). While this regimen has demonstrated promise in pre-clinical models, translation to clinical trials has not yielded the same equivocal results (Audia et al., Clin Exp Immunol 150(3):523-530, 2007; Vermeij et al., Int J Cancer 131(5): E670-680, 2012), although Walter et al. recently published data showing that a single dose of cyclophosphamide before a peptide vaccine was associated with longer patient survival in a Phase II study in renal cell carcinoma (RCC) patients (Walter et al., Nat Med 18: 1254-1261, 2012). However, there was no measurable effect of sbCPA treatment on the immunogenicity of the vaccine.

An alternate approach to single bolus administration of cyclophosphamide is to deliver it in a metronomic schedule by administering a very low dose cyclophosphamide daily. Metronomic cyclophosphamide administration has been reported to have similar immunomodulatory effects to the single low dose cyclophosphamide (Ghiringhelli et al., Cancer Immunol Immunother 56(5): 641-648, 2007; Le and Jaffee, Cancer Res 72(14): 3439-3444, 2012).

It has now been surprisingly and unexpectedly found that the administration of at least two doses of cyclophosphamide to a subject prior to administration of a survivin vaccine (e.g. DPX-Survivac) is capable of improving the efficacy of the vaccine. This is quite a significant finding since the results disclosed herein relate to clinical phase studies in humans, as compared to pre-clinical animal studies.

DPX-Survivac, a survivin vaccine according to the present invention, is a candidate anti-cancer immunotherapeutic vaccine for the treatment of cancer. DPX-Survivac vaccine is designed to target survivin. As described herein, DPX-Survivac contains one decapeptide (SEQ ID NO: 6) and four nonapeptides (SEQ ID NOs: 2, 4, 7 and 8) from the protein sequence of survivin, with different HLA restrictions (HLA-A1, A2, A3, A24 and B7).

The treatment of subjects with DPX-Survivac in the cohort A, cohort B and cohort C (see FIG. 1), as described herein, aimed to address the best treatment schedule to generate strong antigen-specific immune responses upfront, and the maintenance of persistent, tumor directed immune responses over time. This antigen-specific T cell response is expected to exert continuous pressure on developing or new tumors, keeping patients in remission longer.

Subjects treated with DPX-Survivac, in accordance with the methods of the present invention, had extensive immune analysis that lead to several important findings in the Phase I portion of the clinical study. All subjects receiving the DPX-Survivac combination therapy (cohorts B and C, n=12), which comprised a period of low dose cyclophosphamide treatment prior to administration of the vaccine, demonstrated antigen-specific immune responses as measured by at least one of the study's three immune monitoring assays (ELISPOT, tetramer analysis, and multi-parametric intracellular cell staining; Table 1).

TABLE 1

Summary of immune monitoring results from 18 phase 1 subjects treated with a survivin vaccine, with or without low dose cyclophosphamide (IND #14731).

| Cohort/ Subject Id | HLA Type | ELISPOT | Ex vivo Tetramer | In vitro Tetramer | Polyfunctionality by ICS |
|---|---|---|---|---|---|
| A/02-01[a] | A26, A29 | L | − | +[b] | − |
| A/01-02 | A24 | M | N/A | N/A | − |
| A/02-03[a] | A31, A33 | L | N/A | N/A | − |
| A/09-13 | A2 | L, M | − | + | + |
| A/02-18 | A1 | M | + | + | − |
| A/01-19 | A24 | L | N/A | N/A | + |

TABLE 1-continued

Summary of immune monitoring results from 18 phase 1 subjects treated with a survivin vaccine, with or without low dose cyclophosphamide (IND #14731).

| Cohort/ Subject Id | HLA Type | ELISPOT | Ex vivo Tetramer | In vitro Tetramer | Polyfunc- tionality by ICS |
|---|---|---|---|---|---|
| B/02-04 | A2, A1 | M, H | + | + | + |
| B/09-05 | A3, B7 | M, H | + | + | − |
| B/03-06 | A2, A3 | M | − | +[c] | − |
| B/03-07 | A1 | L, M | − | + | − |
| B/02-11 | A24 | M | N/A | N/A | + |
| B/01-12 | A3, A24 | L, M | − | + | − |
| C/09-08 | A2 | H | + | + | + |
| C/10-09 | A2, A24 | H | + | + | + |
| C/11-10 | A2, A3 | H | + | +[c] | + |
| C/01-15 | B7 | M | N/A | N/A | − |
| C/02-16 | A1 | H | + | +[c] | + |
| C/11-17 | A2 | L | − | + | + |

[a] HLA-non-match for survivin peptides in DPX-Survivac;
[b] cross reactive to HLA-A1 tetramer;
[c] positive with tetramer reagents based on two HLA-types, A2 and A3 or A1 and A2.

In Table 1, ELISPOT results (SFU/$10^6$ PBMC), as seen at post treatment time points, are expressed as low (L) when SFU were <128, medium (M) for SFU in the range of 128-512 and high (H) for SFU >512. Tetramer analysis of PBMC was performed either ex vivo (without stimulation) or in vitro (with peptide stimulation), and a two-fold increase of antigen-specific CD8+ T cells over pre-vaccination levels are indicated as positive responders; N/A, not applicable (lack of suitable test reagent). Poly-functional antigen specific CD8+ T cells are defined as those cells secreting IFN-γ and at least one or both of TNF-α and IL-2 simultaneously.

All of the study's high responders were seen within cohorts B and C receiving combination therapy in accordance with the methods of the present invention. In 11 of 12 subjects in cohort B and C, the immune responses were confirmed by two assays (five subjects) or three assays (six subjects). Immune responses were generally established with one or two vaccinations and increased or maintained with boosters. A dose response was observed, with cohort C patients producing significantly higher magnitude responses (cohort C versus cohort B, P=0.013). Low dose cyclophosphamide, beginning prior to vaccine administration, significantly enhanced the 0.5 ml dose (cohort C versus cohort A, P=0.015). Notably, the highest frequency of antigen specific CD8+ T cells were detected ex vivo in PBL's using tetramers and further characterized as polyfunctional by multi-parametric ICS in patients from cohort C, demonstrating that the combination of low dose cyclophosphamide with the survivin vaccine produced the most robust anti-survivin immune response.

Figure 2:
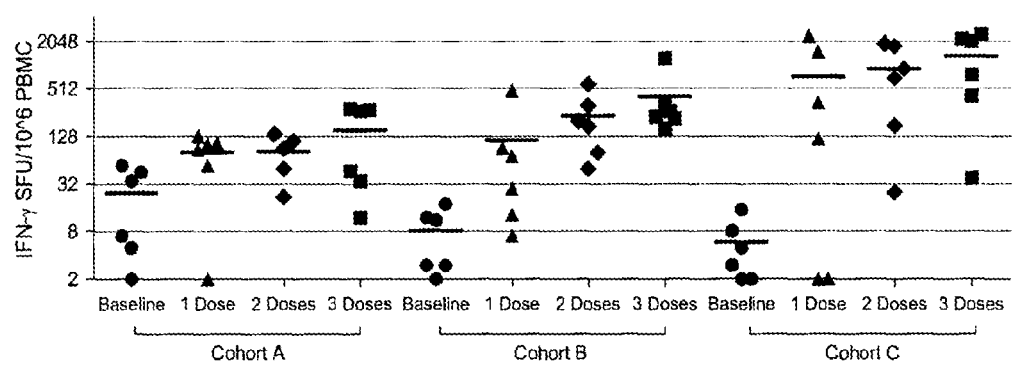
FIG. 2 provides ELISPOT detection results and shows the DPX-Survivac induced increase in interferon gamma production in the peripheral blood mononuclear cells (PBMC) from vaccinated ovarian cancer patients. Subject PBMC were stimulated overnight with survivin peptides in an IFN-γ ELISPOT assay. Data presented represent the number of spot forming units (SFU) per million PBMC from individual subjects and the lines represent mean values at baseline and after one, two and three doses of vaccine administration.

The ELISPOT data for cohorts A and C in FIG. 2 is summarized in Table 2.

TABLE 2

| Number of Vaccinations | Cohort A Highest Immune Response by ELISPOT (SFU/$10^6$ PBMC) | Cohort C Highest Immune Response by ELISPOT (SFU/$10^6$ PBMC) | Fold Difference (Cohort C/ Cohort A) |
|---|---|---|---|
| 1 | 130 | 2309 | 17.7 |
| 2 | 137 | 1911 | 13.9 |
| 3 | 284 | 2517 | 8.9 |

It will be seen from the above table (Table 2) that the highest immune response achieved after a single vaccination in cohort A (vaccine only; n=6) by ELISPOT was 130 SFU/$10^6$ PBMC's (range 55-130). In contrast, the highest response achieved after a single vaccination in cohort C (prior cyclophosphamide+vaccine; n=6) by ELISPOT was 2309 SFU/$10^6$ PBMC's (range 2-2309). This represents a 17.7 times improvement in the highest immune response achieved, demonstrating that the methods of the invention comprising prior administration of an agent that interferes with DNA replication, provide a significant improvement in the efficacy of a survivin vaccine.

Similarly, the efficacy of the DPX-Survivac vaccine was also found to be enhanced by the methods of the invention when two doses or three doses of the vaccine were administered. As shown in Table 2, the highest immune response achieved after two vaccinations in cohort A (vaccine alone; n=5) by ELISPOT is 137 SFU/$10^6$ PBMC's (range 22-137), whereas the highest response achieved after two vaccinations in cohort C (prior cyclophosphamide+vaccine; n=6) by ELISPOT is 1911 SFU/$10^6$ PBMC's (range 25-1911). This represents a 13.9 times improvement in the highest immune response achieved.

After three vaccinations, the highest immune response achieved in cohort A (vaccine alone; n=6) by ELISPOT was 284 SFU/$10^6$ PBMC's (range 12-284). In contrast, the highest immune response achieved in cohort C (prior cyclophosphamide+vaccine; n=6) by ELISPOT was 2517 SFU/$10^6$ PBMC's (range 38-2517). This represents an 8.9 times improvement in the highest immune response achieved.

Figure 4:
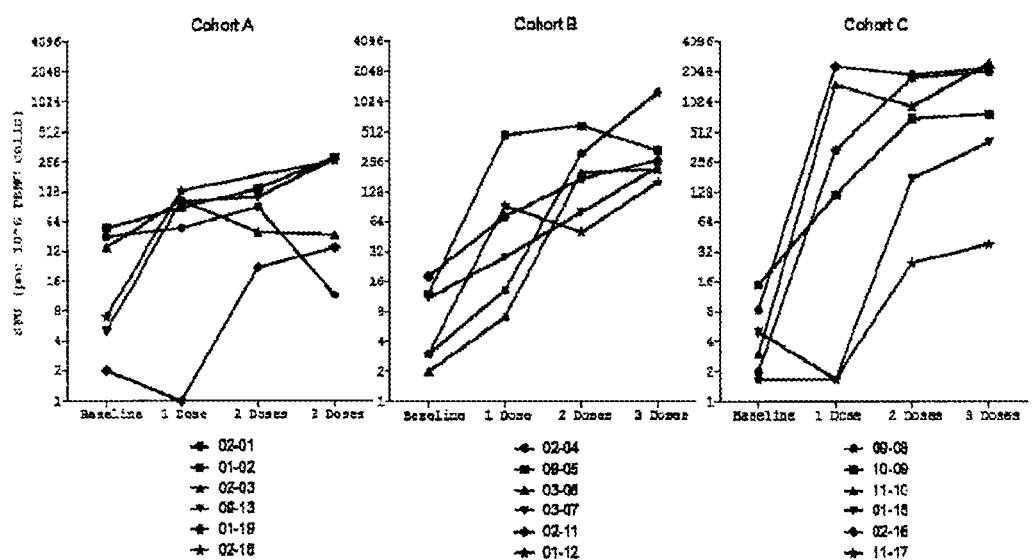
FIG. 4 provides ELISPOT detection results and shows the DPX-Survivac induced increase in IFN-gamma production in the PBMCs from vaccinated ovarian cancer patients. Subject PBMC were stimulated overnight with survivin peptides in an IFN-γ ELISPOT assay. Data presented represent the number of spot forming units (SFU) per million PBMC from individual subjects.

Moreover, as shown in FIG. 4, it was found that after three vaccinations, 4/6 patients in cohort C (prior cyclophosphamide+vaccine) had ELISPOT responses above 512 spots/$10^6$ PBMC's, compared to 0/6 patients in cohort A (survivin vaccine alone) (see FIG. 4). These results show that low dose cyclophosphamide significantly enhanced the immune response provided by the 0.5 ml dose of survivin vaccine. Even after three doses of vaccination in cohort A, none of the patients in cohort A were capable of achieving what was considered for the study to be a high immune response (i.e. SFU >512).

Figure 3:
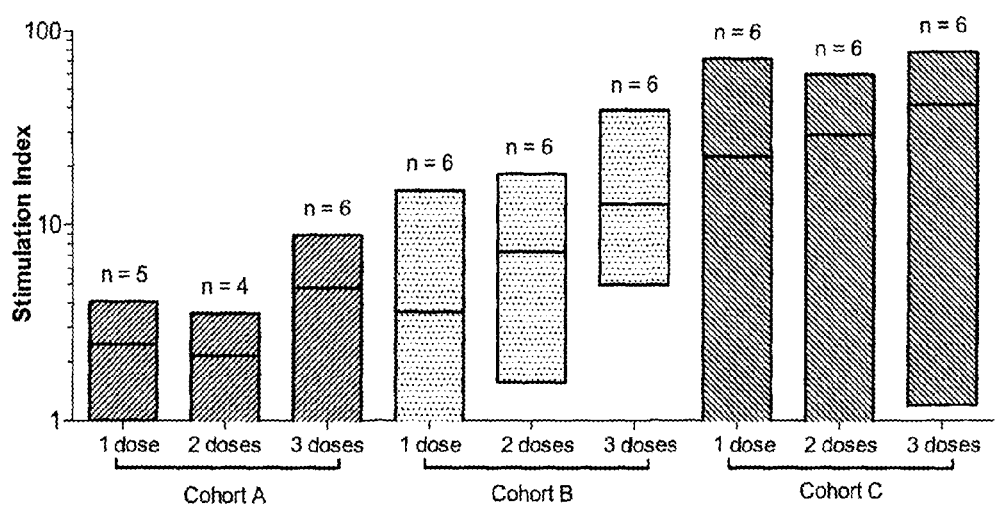
FIG. 3 provides a summary of stimulation factors representing the fold increase in IFN-gamma secreting cells for patients relative to baseline immune responses in these patients. Stimulation factors were calculated using available ELISPOT results. Samples with unexplained high backgrounds in ELISPOT in the absence of peptide stimulation were excluded from the analysis. A minimum stimulation factor of 2× was required to consider a patient an immune responder at a given time point.

The ability of the methods of the invention to improve the efficacy of DPX-Survivac vaccine is further illustrated by the data presented in FIG. 3 which shows the stimulation index for the 1, 2, and 3 dose administrations of vaccine in cohorts A, B and C. The stimulation index represents the fold increase in IFN-gamma secreting cells for patients relative to baseline immune responses in these patients. As shown in FIG. 3, the stimulation factor achieved after three vaccinations in cohort A (vaccine alone; n=6) was 0.4-8.9×, whereas the stimulation factor achieved after three vaccinations in cohort C (prior cyclophosphamide+vaccine; n=6) was 1.2-79×. This represents an 8.9 times improvement in the highest immune response achieved at this time point, demonstrating that the methods of the invention comprising prior administration of an agent that interferes with DNA replication, provide a significant improvement in the efficacy of a survivin vaccine.

Moreover, the highest stimulation factor achieved in at least one patient after 2 doses in cohort A (vaccine alone; n=4) was 3.5×, whereas the highest stimulation factor achieved in at least one patient after 2 doses in cohort C (prior cyclophosphamide+vaccine; n=6) was 59.7×. This represents a 17.1 times improvement in the highest immune response achieved at that time point by the methods of the invention comprising administration of an agent that interferes with DNA replication prior to vaccination with a survivin vaccine.

The higher magnitude of immune responses generated by the methods of the invention (e.g. cohorts B and C), as detected by ELISPOLT, were also characterised by the detection of circulating antigen-specific T cell responses (by tetramer staining) and a polyfunctional T cell response profile in the blood (by ICS staining).

In Vitro Tetramer:

10 of 12 subjects in cohort B and C were evaluable by tetramer staining (Table 1). All 10 showed strong evidence of survivin-specific CD8+ T cell induction following one or two vaccinations with DPX-Survivac. The activation and maintenance of these specific immune cells is of significance since CD8+ T cells are implicated in identifying cancer cells, infiltrating tumors and killing cancer targets. It was found that all evaluable patients in cohort C had tetramer positivity above 1% of total CD8+ T cells (with in vitro stimulation) and reaching as high as 34% of total CD8+ T cells. In contrast, the highest tetramer positivity recorded in cohort A by SD70 was below 1% of total CD8+ T cells (0.7%).

Ex Vivo Tetramer:

As shown in Table 1 above, 1/6 patients in cohort A had detectable tetramer positive CD8+ T cells at least at one time point post vaccination in rested/Un-stimulated PBMCs. Of significance however, in this patient the antigen-specific CD8+ T cells were not polyfunctional as determined by ICS staining. In contrast, 4/6 patients in cohort C had tetramer positive CD8+ T cells at least at one time point post vaccination in rested/un-stimulated PBMCs, and in these patients the antigen-specific CD8+ T cells were confirmed to be polyfunctional by ICS.

Polyfunctionality by ICS:

Moreover, 5/6 patients in cohort C had detectable antigen specific polyfunctional CD8+ T cells, as compared to only 2/6 patients in cohort A (Table 1). These results indicate that patients in cohort C produced a significantly higher magnitude and higher frequency of antigen-specific polyfunctional CD8+ T cells than patients in cohort A.

The results obtained by tetramer and ICS staining were found to correlate with strong immune responses by ELISPOT. Cohort A patients who had tetramer positive cells in rested/unstimulated PBMC's or had polyfunctional antigen-specific CD8+ cells by ICS (i.e. positive by at least one assay but not both) were found to have low/moderate responses by ELISPOT (i.e. between 12-284 SFU/$10^6$ PBMC's after three vaccinations). In contrast, cohort C patients who were tetramer positive and had confirmed polyfunctional antigen-specific CD8+ T cells had moderate/ high immune responses by ELISPOT (i.e. between 773-2517 SFU/$10^6$ PBMC after three vaccinations).

Figure 7:
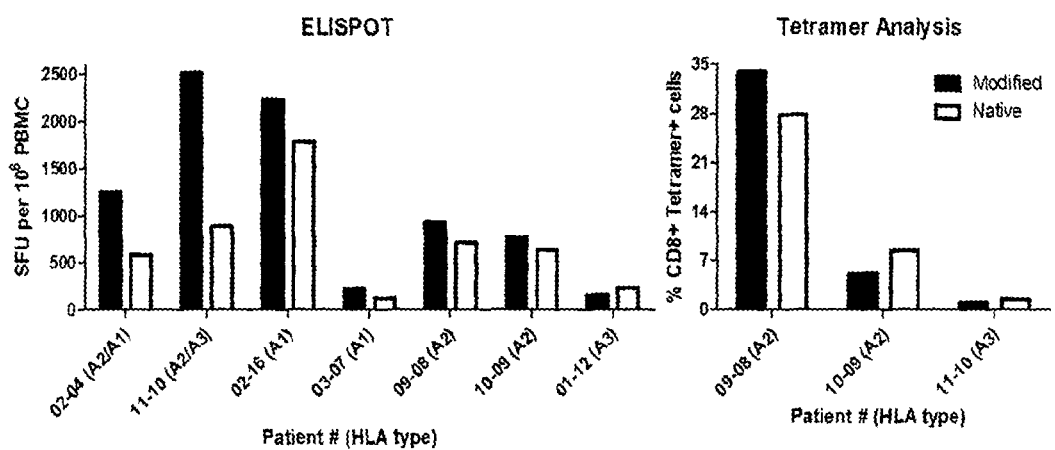
FIG. 7 illustrates ELISPOT and tetramer based analyses of immune responses and reactivity to single amino acid-modified or unmodified native survivin peptide sequences, demonstrating the ability of vaccine induced immune responses to recognize both modified and unmodified survivin peptides.

The results disclosed herein demonstrate that the methods of the invention, comprising prior administration of an agent that interferes with DNA replication, have the ability to improve the efficacy of a survivin vaccine. The methods of the invention may therefore be suitable for the treatment of cancer, particularly those cancers expressing survivin antigens on their cell surface. Moreover, the immune responses generated by the vaccines of the invention may have the potential to target not only tumor cells expressing the specific survivin antigen as contained in the vaccine. As shown in FIG. 7, the immune response generated by the modified survivin peptides in DPX-Survivac displayed cross reactivity to native peptides as well.

The level of immune induction observed by the methods of the invention, comprising prior administration of cyclophosphamide followed by a survivin vaccine was very pronounced and is rarely seen in other self-antigen targeted vaccine approaches. These robust immune responses are generally accepted to be very difficult to achieve in cancer patients and they will likely be the foundation of clinically meaningful anti-tumor immune responses. The strength of the responses in cohort C demonstrates that the prior addition of low dose cyclophosphamide, as an immune modulating drug, is a significant factor in improving the efficacy of the vaccine and generating the strong immune responses that were recorded.

The clinical results disclosed herein provide an exemplary embodiment of the methods of the invention which has broader application to any agent that interferes with DNA replication and to any survivin vaccine, as each are described herein.

Agent that Interferes with DNA Replication

The methods of the present invention involve administrating an agent that interferes with DNA replication prior to administering the vaccine as described herein.

As used herein, the expression "interferes with DNA replication" is intended to encompass any action that prevent, inhibits or delays the biological process of copying (i.e., replicating) the DNA of a cell. The skilled person will appreciate that there exist various mechanisms for preventing, inhibiting or delaying DNA replication, such as for example DNA cross-linking, methylation of DNA, base substitution, etc. The methods according to the invention encompass the use of any agent that interferes with DNA replication by any means known in the art. In an exemplary embodiment, and without limitation, the agent that interferes with DNA replication is a drug.

In an embodiment, the agent that interferes with DNA replication is one which, when used at doses that are non-chemotherapeutic, is capable of selectively affecting DNA replication in cells of the immune system, with the intent of modulating the immune system to enhance vaccine responses. By "non-chemotherapeutic", it is meant that the dose of the agent is a dose lower than that which would be used to directly and selectively destroy malignant or cancerous cells and tissues.

Other embodiments of an agent that interferes with DNA replication include agents that interfere with DNA replication to cause programmed cell death, with the ability to selectively target rapidly dividing cells of the immune system. The purpose of such agents is to modulate cells of the immune system to enhance vaccine responses. Such agents are typically used at doses that are not expected to be chemotherapeutic and are considered acceptable for use in humans. The purpose of selectively targeting immune cells may be to reduce the number of immune suppressive cells, and/or deplete useful immune cells involved in mediating the immune response for the purposes of inducing rapid proliferation upon removal of the drug targeting DNA replication.

Interference with DNA replication leading to cell death may be caused by numerous mechanisms, including but not limited to, the formation of DNA cross-linking (e.g. by alkylating agents, platinum compounds, etc.), methylation of DNA (i.e. by methylating agents), base substitution (i.e. by nucleoside analogs). Exemplary agents and their mechanisms are described in Cancer Chemotherapy and Biotherapy: Principles and Practice (Cabner B. A., 5$^{th}$ edition, Lippincott Williams & Wilkins, Pa., USA, 2011).

In an embodiment, the agent that interferes with DNA replication is an alkylating agent. Alkylating agents include, but are not limited to, cyclophosphamide, temozolomide, ifosfamide, mafosfamide, melphalan, busulfan, bendamustine, uramustine, carmustine or bis-chloroethylnitrosourea (BCNU), chlorambucil, mitomycin C, and their derivatives, active metabolites or metabolite intermediates. A suitable derivative may be, for example and without limitation, palifosfamide (e.g. a derivative of ifosfamide).

In another embodiment, the agent that interferes with DNA replication is a platinum compound. Platinum compounds include, but are not limited to, carboplatin, cisplatin, oxaliplatin and their derivatives.

In another embodiment, the agent that interferes with DNA replication is a methylating agent. Methylating agents include, but are not limited to, temzolomide, procarbazine and dacarbazine, and their derivatives.

In another embodiment, the agent that interferes with DNA replication is a nucleoside analog. Non-limiting examples of nucleoside analogs include gemcitabine, 5-fluorouracil, cytosine arabinoside (Ara-C) and their derivatives.

In another embodiment, any drug that inhibits DNA replication indirectly by inhibiting enzymes critical to DNA replication, such as topoisomerase I, topoisomerase II or DNA polymerase, may also be used. Such drugs include, for example and without limitation, doxorubicin, daunorubicin, mitoxantrone, etoposide, teniposide, topotecan, camptothecin, irinotecan, acyclovir and ganciclovir.

Exemplary agents that interfere with DNA replication, and which may be used in the methods of the invention include, without limitation, those listed below in Table 3. As the skilled person will appreciate, these are examples of agents that may be used. Additional agents include, for example, any drug or compound that interferes with DNA replication by a similar mechanism and/or that has a similar functional group.

TABLE 3

| DNA Replication Inhibitor | Functional group | Description | Exemplary Agents |
| --- | --- | --- | --- |
| Alkylating agents | Nitrogen mustard (bischloroethylamine) $RN(CH_2CH_2Cl)_2$ | Alkylate DNA | Cyclophosphamide |
|  |  |  | Ifosfamide |
|  |  |  | Mafosfamide |
|  |  |  | Melphalan |
|  |  |  | Bendamustine |
|  |  |  | Uramustine |
|  |  |  | Palifosfamide |
|  |  |  | Chlorambucil |
|  |  |  | 4-Hydroxycyclophosphamide |
| Alkylating agents | Nitrosourea | Alkylate DNA | Bis-chloroethylnitrosourea (BCNU) |
| Alkylating agents | Alkyl sulfonates | Alkylate DNA | Busulfan |
| Antitumor Antibiotics | Aziridines or Ethylene imines | Alkylate DNA and Intercalate DNA | Mitomycin C |

TABLE 3-continued

| DNA Replication Inhibitor | Functional group | Description | Exemplary Agents |
|---|---|---|---|
| | | | Yondelis 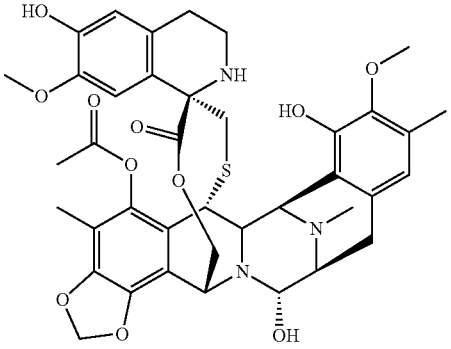 |
| Methylating Agents | Reactive N-methyl group | Methylate DNA | Procarbazine<br>Dacarbazine<br>Temozolomide 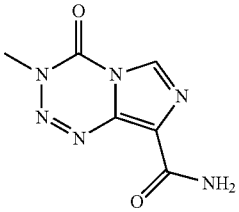 |
| Platinum compounds | Pt(II) | Covalently binds to DNA | Cisplatin<br>Carboplatin<br>Oxaliplatin |
| Nucleoside analogs | Resemble purine or pyrimidine bases | Incorporate into DNA during replication | Acyclovir<br>Gemcitabine<br>5-fluorouracil<br>Cytosine arabinoside<br>Ganciclovir |
| Camptothecin derivatives | Quinoline alkaloids | Inhibits activity of topoisomerase I | Camptothecin 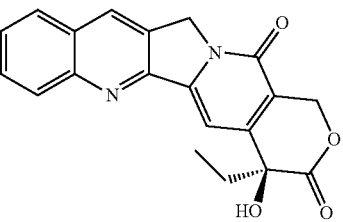 [SMILES: CC[C@@]1(O)C(=O)OCc2c1cc1n(c2=O)Cc2cc3ccccc3nc2-1] |

TABLE 3-continued

| DNA Replication Inhibitor | Functional group | Description | Exemplary Agents |
|---|---|---|---|
| | | | Topotecan |
| | | | Irinotecan |
| Anthracycline derivatives | Anthracycline antibiotics | Inhibit activity of topoisomerase II | Doxorubicin |
| | | | Daunorubicin |
| | | | Epirubicin |
| | | | Idarubicin |
| Epipodophyllotoxin derivatives | Epipodophyllotoxin | Inhibit activity of topoisomerase II | Etoposide |
| | | | Teniposide |
| Anthracenedione derivatives | Anthracenedione | Intercalate DNA | Mitoxantrone |
| | | | Pixantrone |

In a particular embodiment, the agent that interferes with DNA replication is a nitrogen mustard alkylating agent, or any intermediary or active metabolite thereof. Nitrogen mustards are non-specific DNA alkylating agents. Nitrogen mustards form cyclic aminium ions (aziridinium rings) by intramolecular displacement of the chloride by the amine nitrogen. This azidirium group is then capable of alkylating DNA by attacking the N-7 nucleophilic center on the guanine base. Upon displacement of the second chlorine, a second alkylation step occurs that results in the formation of interstrand cross-links (ICLs). These lesions are highly cytotoxic since they block fundamental metabolic processes such as DNA replication and transcription.

The methods of the invention encompass the use of any such non-specific nitrogen mustard DNA alkylating agents. Particularly suitable nitrogen mustard alkylating agents may include for example, and without limitation, cyclophosphamide, palifosfamide, bendamustine, and ifosfamide.

Ifosfamide is a nitrogen mustard alkylating agent. The IUPAC name for ifosfamide is N-3-bis(2-chloroethyl)-1,3,2-oxazaphosphinan-2-amide-2-oxide. Ifosfamide is commonly known as Ifex®. The chemical structure of ifosfamide is:

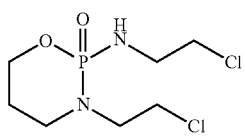 [SMILES: O=P1(NCCCl)OCCCN1CCCl]

Palifosfamide is an active metabolite of ifosfamide that is covalently linked to the amino acid lysine for stability. Palifosfamide irreversibly alkylates and cross-links DNA through GC base pairs, resulting in irreparable 7-atom inter-strand cross-links; inhibition of DNA replication and/or cell death. Palifosfamide is also known as Zymafos®.

Bendamustine is another nitrogen mustard alkylating agent. The IUPAC name for Bendamustine is 4-[5-[Bis(2-chloroethyl)amino]-1-methylbenzimidazol-2-yl]butanoic acid, and it is commonly referred to as Treakisym®, Ribomustin®, Levact® and Treanda®. The chemical structure of bendamustine is:

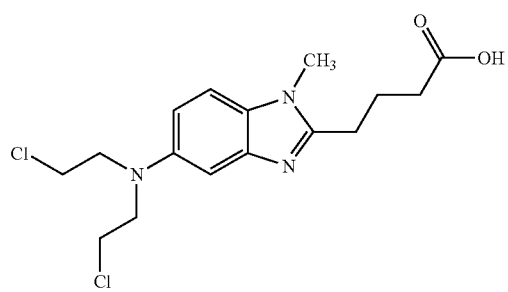 [SMILES: Cn1c(CCCC(=O)O)nc2cc(N(CCCl)CCCl)ccc21]

Also encompassed by the methods of the invention is the use of intermediary and/or active metabolites of DNA alkylating agents, and particularly intermediary and/or active metabolites of the nitrogen mustard DNA alkylating agents described herein. Such metabolites include, without limitation, aldophosphamide, 4-hydroxycyclophosphamide, 4-hydroxyifosfamide, chloracetaldehyde and phosphamide mustard.

In a further embodiment, the agent that interferes with DNA replication may be any suitable pharmaceutically acceptable salt, ester, tautomer, stereoisomer, racemic mixture, solvate, hydrate or prodrug of the alkylating agents, platinum compounds, methylating agents, or nucleoside analogs described herein.

In a particular embodiment, the agent that interferes with DNA replication for use in the methods of the invention is cyclophosphamide.

Cyclophosphamide (CPA)

Cyclophosphamide (N,N-bis(2-chloroethyl)-1,3,2-oxazaphosphinan-2-amine 2-oxide), also known as cytophosphane, is a nitrogen mustard alkylating agent. The chemical structure of cyclophosphamide is:

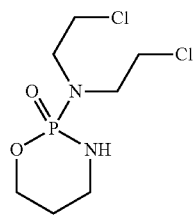 [SMILES: O=P1(N(CCCl)CCCl)NCCCO1]

Cyclophosphamide is also known and referred to under the trade-marks Endoxan®, Cytoxan®, Neosar®, Procytox® and Revimmune®. Other nitrogen mustard alkylating agents in the same class as cyclophosphamide include, without limitation, palifosfamide, bendamustine and ifosfamide.

Cyclophosphamide (CPA) is a prodrug which is typically administered via intravenous infusion, but also can be administered parenterally and orally (de Jonge, Huitema et al. 2005) with little difference in bioavailability (Juma, Rogers et al. 1979). CPA is converted to its active metabolites, 4-hydroxy-CPA and aldophosphamide, by oxidation by P450 enzymes in the liver (Emmenegger, Shaked et al. 2007; 2011). The active metabolites of CPA are lipid soluble and enter cells through passive diffusion. Intracellular 4-OH-CPA spontaneously decomposes into phosphoramide mustard which is the ultimate active metabolite. Phosphoramide mustard catalyzes intra- and interstrand DNA cross-links as well as DNA-protein cross-links that inhibit DNA replication leading to cell death (de Jonge, Huitema et al. 2005). Phosphoramide mustard is eliminated by enzymatic conversion to carboxyphoshpamide by cytoplasmic aldehyde dehydrogenase (ALDH) (Emmenegger, Shaked et al. 2007; 2011). Cells with low levels of ALDH tend to accumulate CPA metabolites and are more sensitive to its effects, and indeed tumor upregulation of ALDH is one mechanism of CPA resistance (Zhang, Tian et al. 2005). Besides ALDH, low intracellular ATP levels have also been associated with CPA selectivity towards particular cells types (Zhao, Cao et al. 2010). At high doses, typically in the range of 1-5 g/m², the effects of CPA are most cytotoxic to rapidly dividing cells indiscriminate of cell type, and CPA is myelosuppressive since most hematogenic cells are rapidly dividing (Bruce, Meeker et al. 1966; Smith and Sladek 1985).

Total systemic clearance of CPA and its metabolites varies between 5-9 hours, and peak plasma levels of the parent also vary considerably between patients (3-11 hours) reflecting genetic differences in metabolism from person to person (Cohen, Jao et al. 1971; Mouridsen, Faber et al. 1974). Repeated administration of CPA is reported to shorten elimination half-life by increasing activity of enzymes involved in metabolism (D'Incalci, Bolis et al. 1979), but whether this leads to increased metabolism of the active metabolite is not known (de Jonge, Huitema et al. 2005), particularly at low doses (Emmenegger, Shaked et al. 2007).

Dose translation from human to murine studies is calculated using the following equation:

$$\frac{\text{Human dose (mg/kg)}}{\text{Animal dose (mg/kg)}} = \frac{\text{Animal } Km}{\text{Human } Km}$$

Where the constant mouse Km value is 3 and human Km value is 37 (Reagan-Shaw, Nihal et al. 2008). Using this calculation, daily metronomic treatment in humans consisting of 50 mg BID, PO is equivalent to 20.56 mg/kg in mouse. The dose of 20 mg/kg PO has been evaluated in pre-clinical models and determined to be biologically equivalent to the human dose (Voelcker, Wagner et al. 1984; Man, Bocci et al. 2002).

In the last two decades low dose CPA has been appreciated for its immune modulatory and anti-angiogenic effects. In contrast to high dose CPA, low doses of CPA, typically 100-300 mg/m², lack widespread cytotoxic activity but do appear to enhance immune-mediated tumor elimination by selectively modulating cells of the immune system and also by reducing angiogenesis within the tumor microenvironment. Alone, low dose CPA therapy has been demonstrated to delay tumor growth in animal models, but is ineffective at complete tumor eradication. The mechanisms of CPA-induced tumor delay are complementary to combination with other forms of immune therapy, such as cancer vaccines. Low dose CPA, typically <300 mg/m², can be delivered as a single bolus injection (sbCPA) or orally over several days as a metronomic therapy (mCPA). Pioneering studies by Robert North in the 1980's (North 1982; Awwad and North 1988) were the first to indicate the CPA selectively depletes immune suppressor cells that were responsible for quelling active immune responses towards tumors. Since then, CPA has also been reported to selectively reduce and impair functionality of CD4+CD25hiFoxP3+ regulatory T cells (Lutsiak, Semnani et al. 2005), inhibit tumor angiogenesis (Browder, Butterfield et al. 2000), increase activation of dendritic cells (Radojcic, Bezak et al. 2009), skew immune response towards Th1 (Schiavoni, Mattei et al. 2000) and restore T and NK effector function (Ghiringhelli, Menard et al. 2007). In mice, the effects of a single bolus low dose administration of CPA are transient, typically reaching nadir within 4 days after administration and returning to normal by 7-10 days (Lutsiak, Semnani et al. 2005; Salem, Al-Khami et al. 2012).

Low dose CPA has been combined with cancer vaccines in pre-clinical models and in clinical trials. Hermans et al. examined the efficacy of low dose CPA treatment in tumor bearing mice that had been prophylactically immunized with a DNA/MVA prime/boost strategy. Briefly, mice were immunized with plasmid DNA encoding the tumor antigen mel3, then boosted with MVA encoding the same antigen 14 days later. Seven days after the MVA boost, mice were challenged with B16-F10 tumors and then treated every 6 days with low dose CPA (175 mg/kg, IP) (Hermans, Chong et al. 2003). They found that mice previously immunized and then treated with low dose CPA had a significant delay in tumor growth, but either treatment alone had no effect. They did not detect an increase in number of antigen-specific CD8+ T cells. A study by Barbon et al. in non-tumor bearing mice demonstrated that 3 daily injections of low dose CPA (20 mg/kg/day IP) given prior to a DNA vaccine encoding the CYP1B1 antigen provided better immune responses than single administration of low or high dose (20 or 200 mg/kg) CPA 2 days prior to vaccine (Barbon, Yang et al. 2010). The daily doses of CPA were given with the last dose occurring 2 days prior to vaccination. In this study, the daily CPA treatments were more effective at reducing total numbers of Tregs with a sparing of effector CD8+ T cells. Wada et al. studied various regimens of low dose CPA (50 mg/kg IV) with a GVAX vaccine in an autologous TRAMP-C2/HA prostate tumor model (Wada, Yoshimura et al. 2009). These tumors develop naturally in mice and express the HA antigen. CPA was given once prior to or once after vaccination to establish the best regimen. Pre-administration of a single low dose bolus was most effective at producing CD8+ T cells. The immunogenicity of the vaccine was further enhanced by giving mice two vaccinations 7 days apart (days 0 and day 7) combined with a single dose of low dose cyclophosphamide prior to each vaccine (CPA given day −1 and day 6). They reported an increase in the number of total circulating CD4 and CD8, and specifically an increase in antigen-specific CD8+ T cells. A study by Salem et al. evaluated different doses of CPA as a single bolus low dose administration 3 days before vaccination (Salem, Kadima et al. 2007). This study used a transgenic model whereby wild-type mice were treated with a single IP injection of CPA 2 days before OT-1 transgenic T cells were adoptively transferred and 3 days before mice were vaccinated with Ovalbumin peptide (100 ug; SIINFEKL, 257-264) s.c. delivered in PBS. The ability of the vaccine to increase the number of circulating antigen specific T cells was measured after pretreatment with PBS, 1 mg CPA or 4 mg CPA. They found that 1 mg CPA (corresponding to a 50 mg/kg dose) did not expand the antigen-specific OT-I T cells more than the PBS-sham treatment, but 4 mg of CPA (corresponding to 200 mg/kg) did. Although both doses are considered "low dose", a single administration did not result in consistent enhancement of the vaccine-induced immune response. Most recently, Peng et al. compared daily CPA (10 mg/kg/day) to sbCPA (50 mg/kg) in combination with a DNA vaccine encoding the HPV16 E7 protein in a TC-1 HPV16 tumor model (Peng, Lyford-Pike et al. 2012). In this model, the mice were vaccinated therapeutically starting 9 days after implantation and repeated once a week for the next two weeks. mCPA was administered continuously for four weeks or administered as a single low dose prior to each vaccination. All CPA treatment were started on day 8, one day before the first vaccination. They found both sbCPA and mCPA combined with vaccine to provide increased tumor protection and that a single administration of CPA prior to each vaccine provide the strongest CD8 responses and the best anti-tumor activity. Finally, Taieb et al. tested low dose CPA with a Mart-1 exosome vaccine in a melanoma model (Taieb, Chaput et al. 2006). Briefly, HLA-A2 transgenic mice were implanted with B16.A2 tumors on day 0, then treated with low dose CPA (100 mg/kg IP) on day 6 and vaccinated on day 12. Mice treated with the combination demonstrated significantly better tumor control than either treatment alone, as well as significant increase in antigen-specific CD8+ T cells and IFN-γ release.

Low dose CPA has also been tested in clinical trials. Ghiringhelli et al. first reported that mCPA (with no vaccination) delivered for one month as 50 mg BID in stage IV cancer patients resulted in significant decrease in circulating Tregs, but total circulating levels of CD4, CD8 and NK cells were not affected (Ghiringhelli, Menard et al. 2007). In addition, they reported that T cells and NK cells in treated patients had increased proliferation capacity, suggesting that mCPA treatment may combine well with vaccine. A phase I/II study (n=14) compared efficacy of a dendritic cell vaccine (monocyte derived dendritic cells loaded with Her2/neu, hTERT and PADRE peptides) with and without single low dose bolus of CPA (sbCPA, 300 mg/m$^2$ delivered intravenously 2 days before vaccine) in 14 ovarian cancer patients (Chu, Boyer et al. 2012). The patients receiving the combination treatment were reported to potentially have better progression free survival and overall survival, but the results were not statistically significant in this study due to small patient population. They did not detect decreases in circulating Tregs in patients treated with CPA, and no enhancement of the T cell response as measured by IFN-γ ELISPOT between the CPA and non-CPA arms were demonstrated. Another single arm phase II study in melanoma patients (n=28) tested the combination of a dendritic cell vaccine (autologous dendritic cells, loaded with peptides derived from KLH, survivin, hTERT, p53 and PADRE, vaccinated intradermally) with orally delivered mCPA but starting after vaccination (50 mg BID, one week on-one week off) (Engell-Noerregaard et al. 2012). In assessing vaccine induced immune responses in this single arm trial (which combined the DC based vaccine with IL-2, and a Cox-2 inhibitor as well as CPA), IFN-γ ELISPOT indicated modest immune responses from baseline to fourth vaccination, with slowly declining responses occurring over time. Importantly, these responses were of low frequency or undetectable directly ex vivo, typical of peptide vaccine therapy alone. Responses in these patients were not directly compared to patients receiving vaccine without treatment with CPA and it is not clear if CPA alone or in combination with IL-2 and a Cox-2 inhibitor contributed to vaccine efficacy, if at all.

In a single arm phase II trial in ovarian cancer patients (n=10), a vaccine containing a p53-SLP (synthetic long peptide), which consisted of ten synthetic overlapping peptides emulsified in Montanide and delivered subcutaneously into patients (at 3 week intervals), was combined with a single low dose bolus of CPA (sbCPA, 300 mg/m$^2$, 2 days before vaccine). This study reported increased IFN-γ ELISPOT responses in patients receiving the combination therapy, when compared to a previous trial testing the vaccine alone (Vermeij, Leffers et al. 2011). Comparing treatment outcome across different trials however is prone to selection bias which could skew the results. A more systematically performed trial in melanoma compared the use of two unique multipeptide vaccines (containing peptides to Tyrosinase, MAGE-A1, MAGE-A3, gp100, MAGE-A10 and/or NY-ESO1) delivered with T helper peptides as a water-in-oil emulsion half subcutaneously and half intradermally with or without sbCPA (300 mg/m$^2$, prior to vaccination). This study carefully examined CD4+ and CD8+ T cell responses post vaccination by ELISPOT, and found that sbCPA provided no detectable improvement when combined with vaccination. Finally, a phase I/II study by Walter et al. in renal cell carcinoma tested combination of a peptide vaccine (IMA901) with sbCPA (300 mg/m$^2$ 3 days before vaccine) (Walter, Weinschenk et al. 2012). The two-arm phase II study (n=68) compared vaccine with and without sbCPA treatment. They reported that immune-responders within the group treated with the sbCPA/vaccine combination had better survival than non-responders in the same group, and also the group treated with vaccine only. Yet, there was no measurable effect of sbCPA treatment on the immunogenicity of the vaccine.

In summary, CPA has been tested in combination with vaccines in clinical trials, both as a single low dose intravenous infusion prior to vaccination, as well as a metronomic low dose oral therapy starting after vaccination. These trials have generated contradictory results and did not demonstrate a definitive and broadly applicable benefit for the use low dose CPA for the purposes of enhancing vaccine activity.

To date and to Applicants knowledge, the benefits of administering a single low dose of CPA or multiple low doses of CPA prior to vaccination have not been directly compared in a clinical trial. We compared the results obtained according to the methods of the present invention comprising repeated CPA administration before vaccination of cancer patients with our multi-peptide based survivin vaccine (tested against vaccine without CPA in the same trial) to results achieved with a single low dose of CPA before vaccination with two different multi peptide based vaccine MELITAC 12.1 and MELITAC12.6 in cancer patients (both tested against vaccine without CPA in the same trial) by Slingluff et al. (2011).

In the absence of CPA pre-treatment, the survivin peptide vaccine and the melanoma vaccines MELITAC 12.1 and MELITAC 12.6 all had similar immunogenicity potentials based on ELISPOT results. Immune responses produced by up to three vaccinations with MELITAC 12.1 and MELITAC 12.6 alone ranged from 0-1095 spots per 100,000 CD8+ T cells for MELITAC 12.1 and 0-700 spots for MELITAC 12.6. In comparison, ELISPOT values from patients receiving up to three vaccinations of DPX-Survivac alone were in the range of 0-291 spots per 100,000 CD8+ T cells after converting values from spots per 1,000,000 PBMC to spots per 100,000 CD8+ T cells. T cell counts in patient PBMCs were determined by flow cytometry and the data presented herein was converted to number of spots per 100,000 CD8+ T cells for direct comparison with results produced by the MELITAC vaccines.

Comparatively, combining MELITAC 12.1 and MELITAC 12.6 with a single low dose of CPA prior to vaccine produced immune responses ranging from 0-1095 and 0-700 for MELITAC 12.1 and MELITAC 12.6, respectively. Thus, the immune responses generated by administering a single low dose of CPA prior to MELITAC 12.1 and MELITAC 12.6 were essentially unchanged as compared to vaccine alone.

In contrast, patients administered multiple doses of CPA prior to vaccination with DPX-Survivac generated ELISPOT responses ranging from 0-8467 spots per 100,000 CD8+ T cells. This significant increase in immune responses after repeated administration of CPA prior to vaccination with DPX-Survivac (0-8467 versus 0-291) demonstrates that pre-treatment with repeated low doses of cyclophosphamide prior to vaccination is more beneficial for enhancing an immune response by a vaccine than administering a single low dose of cyclophosphamide prior to vaccination.

Vaccine Compositions

As used herein, the terms "vaccine", "vaccine composition" or "composition" may be used interchangeably.

Vaccine compositions of the invention, for use together with an agent that interferes with DNA replication, may be of any form suitable for delivery of a survivin antigen to a subject. Vaccine compositions according to the invention can be formulated according to known methods, such as by admixture of the one or more survivin antigens with one or more pharmaceutically acceptable excipients or carriers, preferably those acceptable for administration to humans. Examples of such excipients, carriers and methods of formulation may be found e.g. in Remington's Pharmaceutical Sciences (Maack Publishing Co, Easton, Pa.). To formulate a pharmaceutically acceptable vaccine composition suitable for effective administration, such compositions will typically contain a therapeutically effective amount of a survivin antigen, such as a survivin polypeptide, a survivin peptide or a survivin peptide variant as described herein, or a nucleic acid molecule or vector encoding such survivin antigen.

Vaccine compositions according to the invention may be administered to a subject in a therapeutically effect amount. As used herein, a "therapeutically effective amount" means an amount vaccine or active ingredient (e.g., one or more survivin antigens) effective to treat, prevent, alleviate, or ameliorate cancer or symptoms of cancer; prolong the survival of the subject being treated; and/or stimulate, induce or enhance an immune response in a subject, such as a cytotoxic T cell response. In some embodiments, a therapeutically effective amount of the vaccine is an amount capable of inducing a clinical response in a subject in the treatment of cancer. Determination of a therapeutically effective amount of the vaccine is well within the capability of those skilled in the art, especially in light of the disclosure provided herein. The therapeutically effective amount may vary according to a variety of factors such as the subject's condition, weight, sex and age.

Once one or more appropriate survivin antigens have been selected for inclusion in a vaccine composition according to the invention, the antigens may be delivered by various suitable means which are known in the art. Vaccine compositions for use in the methods described herein can include for example, and without limitation, lipopeptides (e.g., Vitiello, A. et al., J. Clin. Invest. 95:341, 1995), peptide compositions encapsulated in poly(DL-lactide-co-glycolide) ("PLG") microspheres (see, e.g., Eldridge, et al., Molec. Immunol. 28:287-294, 1991: Alonso et al., Vaccine 12:299-306, 1994; Jones et al., Vaccine 13:675-681, 1995), peptide compositions contained in immune stimulating complexes (ISCOMS) (see, e.g., Takahashi et al., Nature 344:873-875, 1990; Hu et al., Clin Exp Immunol. 113:235-243, 1998), multiple antigen peptide systems (MAPs) (see e.g., Tam, J. P., Proc. Natl. Acad. Sci. U.S.A. 85:5409-5413, 1988; Tam, J. P., J. Immunol. Methods 196:17-32, 1996), peptides formulated as multivalent peptides; peptides for use in ballistic delivery systems, typically crystallized peptides, viral delivery vectors (Perkus, M. E. et al., In: Concepts in vaccine development, Kaufmann, S. H. E., ed., p. 379, 1996; Chakrabarti, S. et al., Nature 320:535, 1986; Hu, S. L. et al., Nature 320:537, 1986; Kieny, M.-P. et al., AIDS Bio/Technology 4:790, 1986; Top, F. H. et al., J. Infect. Dis. 124:148, 1971; Chanda, P. K. et al., Virology 175:535, 1990), particles of viral or synthetic origin (e.g., Kofler, N. et al., J. Immunol. Methods. 192:25, 1996; Eldridge, J. H. et al., Sem. Hematol. 30:16, 1993; Falo, L. D., Jr. et al., Nature Med. 7:649, 1995), adjuvants (Warren, H. S., Vogel, F. R., and Chedid, L. A. Annu. Rev. Immunol. 4:369, 1986; Gupta, R. K. et al., Vaccine 11:293, 1993), liposomes (Reddy, R. et al, J. Immunol. 148:1585, 1992; Rock, K. L., Immunol. Today 17:131, 1996), or, naked or particle absorbed cDNA (Ulmer, J. B. et al., Science 259:1745, 1993; Robinson, H. L., Hunt, L. A., and Webster, R. G., Vaccine 11:957, 1993; Shiver, J. W. et al., In: Concepts in vaccine development, Kaufmann, S. H. E., ed., p. 423, 1996; Cease, K. B., and Berzofsky, J. A., Annu. Rev. Immunol. 12:923, 1994 and Eldridge, J. H. et al., Sem. Hematol. 30:16, 1993).

Vaccine compositions of the invention also encompass nucleic acid mediated modalities. For example, DNA or RNA encoding one or more of the survivin antigens as described herein may be administered to the subject. Such approaches are described, for example, in Wolff et al., Science 247:1465 (1990) as well as U.S. Pat. Nos. 5,580, 859; 5,589,466; 5,804,566; 5,739,118; 5,736,524; 5,679, 647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

In further embodiments of the vaccine compositions, the survivin antigens (e.g. survivin peptides) may also be expressed by viral or bacterial vectors. Examples of expression vectors include attenuated viral hosts, such as vaccinia or fowlpox. This approach involves the use of vaccinia virus, for example, as a vector to express nucleotide sequences that encode the survivin peptides as described herein. Upon introduction into an acutely or chronically infected host or into a non-infected host, the recombinant vaccinia virus expresses the antigenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art and are encompassed by the vaccine compositions described herein.

Vaccines in accordance with the invention also encompass compositions containing one or more of the survivin antigens, where the antigen can be present individually or as a construct containing multiple copies of the same or different survivin antigens. For example, the survivin antigen can be present as a single nucleic acid molecule (e.g. vector) encoding several of the same or different survivin antigens. Or, in other embodiments, a homopolymer comprising multiple copies of the same survivin antigen, or a heteropolymer of various different survivin antigens, may be used. Such polymers may have the advantage of providing an increased immunological reaction as they comprise multiple copies of survivin antigens, such that the resultant effect may be an enhanced ability to, induce an immune response with the one or more antigenic determinants of survivin. The composition can comprise a naturally occurring region of one or more survivin antigens or can comprise prepared antigens, e.g., recombinantly or by chemical synthesis.

A vaccine of the invention can also include antigen-presenting cells (APC), such as dendritic cells (DC), as a vehicle to present the one or more suvivin antigens (e.g. survivin peptides). Such vaccine compositions can be created in vitro, following dendritic cell mobilization and harvesting, whereby loading of dendritic cells occurs in vitro. For example, dendritic cells are transfected with DNA or RNA encoding the one of more survivin antigens, or are pulsed with survivin peptide antigens. The dendritic cell can then be administered to a subject to elicit an immune response in vivo.

A vaccine according to the invention may be administered by any suitable means, such as e.g. injection (e.g. intramuscular, intradermal, subcutaneous, intravenous or intraperitoneal), aerosol, oral, nasal, topical, intravaginal, transdermal, transmucosal, or any other suitable routes. The vaccine may be formulated for systemic or localized distribution in the body of the subject. Systemic formulations include those designed for administration by injection, as well as those designed for transdermal, transmucosal or oral administration.

For injection, the vaccines may be formulated in a carrier comprising a continuous phase of a hydrophobic substance as described herein, such as a water-in-oil emulsion or an oil-based carrier. In some embodiments, liposomes may be used together with the carrier. The vaccines may also be formulated as aqueous solutions such as in Hank's solution, Ringer's solution or physiological saline buffer.

As will be apparent from the above, vaccine compositions of the invention are meant to encompass any composition or antigen delivery means (e.g. viral vectors) which are useful in the treatment of cancer, including compositions capable of stimulating an immune response in a subject, such as a specific cytotoxic T cell response upon administration.

To obtain vaccine compositions of the invention, it may be suitable to combine the survivin antigen, which may be a relatively small survivin peptide, with various materials such as adjuvants, excipients, surfactants, immunostimulatory components and/or carriers. Adjuvants may be included in the vaccine composition to enhance the specific immune response. Different carriers may be used depending on the desired route of administration or the desired distribution in the subject, e.g. systemic or localized.

In a particular embodiment, the vaccine for use in the methods of the invention is a composition comprising at least one survivin antigen, liposomes and a carrier comprising a continuous phase of a hydrophobic substance. In a further embodiment, the composition may additionally comprise an adjuvant. In a further embodiment, the composition may additionally comprise a T-helper epitope or antigen.

Thus, in an embodiment, the vaccine composition comprises one or more survivin antigens; a T-helper epitope; an adjuvant; liposomes; and a carrier comprising a continuous phase of a hydrophobic substance. The T-helper epitope may, for example, be a peptide comprising the amino acid sequence AQYIKANSKFIGITEL (SEQ ID NO: 9). The adjuvant may, for example, be a polyI:C polynucleotide.

In a further embodiment, the vaccine for use in the methods of the invention is a composition comprising at least one survivin antigen, together with Immunovaccine, Inc's liposome-based and/or amphipathic compound-based vaccine adjuvanting platform, including, but not limited to, the VacciMax® and DepoVax™ platform technologies (see e.g. U.S. Pat. Nos. 6,793,923 and 7,824,686; WO 2002/038175; WO 2007/041832; WO 2009/039628; WO 2009/043165 and WO 2009/146523). The DepoVax™ platform is a vaccine delivery formulation that provides controlled and prolonged exposure of antigens plus adjuvant to the immune system. The platform is capable of providing a strong, specific and sustained immune response and is capable of single-dose effectiveness.

In a further embodiment, the vaccine of the invention is any suitable composition as described above, comprising one or more survivin peptide antigens having the amino acid sequence: FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); and LPPAWQPFL (SEQ ID NO: 8).

In a further embodiment, the vaccine composition comprises five survivin peptide antigens comprising the amino acid sequences: FTELTLGEF (SEQ ID NO: 2), LMLGEFLKL (SEQ ID NO: 4), RISTFKNWPK (SEQ ID NO: 6), STFKNWPFL (SEQ ID NO: 7), and LPPAWQPFL (SEQ ID NO: 8); a T-helper epitope; an adjuvant; liposomes; and a carrier comprising a continuous phase of a hydrophobic substance. The T-helper epitope may, for example, be a peptide comprising the amino acid sequence AQYIKANSKFIGITEL (SEQ ID NO: 9). The adjuvant may, for example, be a polyI:C polynucleotide. The liposomes may, for example, be comprised of 1,2-Dioleoyl-sn-glycero-3-phosphocholine (DOPC; synthetic phospholipid) and cholesterol. The hydrophobic carrier may, for example, be Montanide® ISA51 VG.

In a particular embodiment, the vaccine of the invention may be Immunovaccine, Inc's candidate anti-cancer immunotherapeutic vaccine DPX-Survivac. DPX-Survivac comprises five synthetic survivin peptide antigens having the amino acid sequences: FTELTLGEF (SEQ ID NO: 2), LMLGEFLKL (SEQ ID NO: 4), RISTFKNWPK (SEQ ID NO: 6), STFKNWPFL (SEQ ID NO: 7), and LPPAWQPFL (SEQ ID NO: 8); a universal T-helper epitope from tetanus toxoid (AQYIKANSKFIGITEL; SEQ ID NO: 9); a polyI:C polynucleotide adjuvant; liposomes consisting of DOPC and cholesterol; and the hydrophobic carrier Montanide® ISA 51 VG. Exemplary amounts of each component (per ml of vaccine) include, without limitation, 1.0 mg of each survivin antigen; 0.5 mg of T-helper epitope (e.g. SEQ ID NO: 9); 0.4 mg of adjuvant (e.g. polyI:C polynucleotide); 120.0 mg of synthetic DOPC phospholipid; 12.0 mg of cholesterol; and 0.7 ml of hydrophobic carrier (e.g. Montanide® ISA51 VG).

The vaccine may optionally further comprise additional components such as, for example, emulsifiers. A more detailed disclosure of exemplary embodiments of the vaccine, and the components thereof, are described as follows.

(i) Survivin Antigens

The vaccine compositions of the invention comprise at least one survivin antigen. The expression "at least one" is used herein interchangeably with the expression "one or more". These expressions, unless explicitly stated otherwise herein, refer to the number of different survivin antigens in the vaccine, and not to the quantity of any particular survivin antigen. In accordance with the ordinary meaning of "at least one" or "one or more", the vaccine composition of the invention contains a minimum of one survivin antigen.

Survivin, also called baculoviral inhibitor of apoptosis repeat-containing 5 (BIRC5), is a protein involved in the negative regulation of apoptosis. It has been classed as a member of the family of inhibitors of apoptosis proteins (IAPs). Survivin is a 16.5 kDa cytoplasmic protein containing a single BIR motif and a highly charged carboxy-terminal coiled region instead of a RING finger. The gene coding for survivin is nearly identical to the sequence of Effector Cell Protease Receptor-1 (EPR-1), but oriented in the opposite direction. The coding sequence for the survivin (homo sapiens) is 429 nucleotides long (SEQ ID NO: 10) including stop codons. The encoded protein survivin (homo sapiens) is 142 amino acids long (SEQ ID NO: 11).

It is postulated that the survivin protein functions to inhibit caspase activation, thereby leading to negative regulation of apoptosis or programmed cell death. Consistent with this function, survivin has been identified as one of the top genes invariably up-regulated in many types of cancer but not in normal tissue (see e.g. Altieri et al., Lab Invest, 79: 1327-1333, 1999; and U.S. Pat. No. 6,245,523). This fact therefore makes survivin an ideal target for cancer therapy as cancer cells are targeted while normal cells are not. Indeed, survivin is highly expressed in many tumor types, including a large portion of human cancer, and has reported prognostic value.

Vaccines of the invention comprise one or more survivin antigens. As used herein, the term "survivin antigen" encompasses any peptide, polypeptide or variant thereof (e.g. survivin peptide variant) derived from a survivin protein or a fragment thereof. The term "survivin antigen" also encompasses a polynucleotide that encodes a survivin peptide, survivin peptide variant or survivin peptide functional equivalent described herein. Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

In an embodiment, the survivin antigen may comprise the full length survivin polypeptide or a nucleic acid encoding the full length survivin polypeptide. Alternatively, the survivin antigen may be a survivin peptide comprising a fragment of any length of the survivin protein. Exemplary embodiments include a survivin peptide that comprises at least 5, 6, 7, 8, 9, 10, 11, 12, 13, 14, 15, 16, 17, 18, 19 or 20 amino acid residues. In specific embodiments, the survivin peptide consists of a heptapeptide, an octapeptide, a nonapeptide, a decapeptide or an undecapeptide, consisting of 7, 8, 9, 10, 11 consecutive amino acid residues of the survivin protein (e.g. SEQ ID NO: 11), respectively. Particular embodiments of the survivin antigen include survivin peptides of about 9 or 10 amino acids.

Survivin antigens of the invention also encompass variants and functional equivalents of survivin peptides. Variants or functional equivalents of a survivin peptide encompass peptides that exhibit amino acid sequences with differences as compared to the specific sequence of the survivin protein, such as one or more amino acid substitutions, deletions or additions, or any combination thereof. The difference may be measured as a reduction in identity as between the survivin protein sequence and the survivin peptide variant or survivin peptide functional equivalent.

The identity between amino acid sequences may be calculated using algorithms well known in the art. Survivin peptide variants or functional equivalents are to be considered as falling within the meaning of a "survivin antigen" of the invention when they are, preferably, over their entire length, at least 70% identical to a peptide sequence of a survivin protein, such as at least 75% identical, at least 80% identical, at least 85% identical, at least 90% identical, or at least 95% identical, including 96%, 97%, 98% or 99% identical with a peptide sequence of a survivin protein. In a particular embodiment, the survivin peptide variant has a sequence that is at least 85%, 90%, 95%, 96%, 97%, 98% or 99% identical to a consecutive amino acid sequence of SEQ ID NO: 11.

The survivin protein from which the survivin antigen can be derived is a survivin protein from any animal species in which the protein is expressed. A particular embodiment is the survivin protein from humans (SEQ ID NO: 11). Based on the sequence of the selected survivin protein, the survivin antigen may be derived by any appropriate chemical or enzymatic treatment of the survivin protein or coding nucleic acid. Alternatively, the survivin antigen may be synthesized by any conventional peptide or nucleic acid synthesis procedure with which the person of ordinary skill in the art is familiar.

The survivin antigen of the invention (peptide or nucleic acid) may have a sequence which is a native sequence of survivin. Alternatively, the survivin antigen may be a peptide or nucleic acid sequence modified by one or more substitutions, deletions or additions, such as e.g. the survivin peptide variants or functional equivalents described herein. Exemplary procedures and modifications of survivin peptides that increase the immunogenicity of the peptides include, for example, those described in WO 2004/067023 involving amino acid substitutions introduced at anchor positions which increase peptide binding to the HLA class I molecule.

In an embodiment, the survivin antigen is any peptide derived from the survivin protein, or any survivin peptide variant thereof, that is capable of binding MHC Class I HLA molecules. Along these lines, the survivin antigen may be any survivin peptide, or survivin peptide variant thereof, that is capable of inducing or potentiating an immune response in a subject.

In an embodiment, the survivin antigen is a peptide antigen comprising an amino acid sequence from the survivin protein (SEQ ID NO: 11) that is capable of eliciting a cytotoxic T-lymphocyte (CTL) response in a subject, or a nucleic acid molecule encoding said peptide.

In an embodiment, the vaccine comprises one or more synthetic survivin peptides, or variants thereof, based on the amino acid sequence of the survivin protein, such as the amino acid sequence set forth in SEQ ID NO: 11.

Survivin peptides, survivin peptide variants and survivin functional equivalents, and their use for diagnostic and therapeutic purposes, specifically in cancer, have been described, for example, in WO 2004/067023 and WO 2006/081826. The novel peptides disclosed in these publications were found to be capable of eliciting cytotoxic T-lymphocyte (CTL) responses in cancer patients. In particular, in WO 2004/067023, it was found that MHC Class I restricted peptides can be derived from the survivin protein, which are capable of binding to MHC Class I HLA molecules and thereby eliciting both ex vivo and in situ CTL immune responses in patients suffering from a wide range of cancer diseases.

In an embodiment, the vaccine of the invention may include any one or more of the survivin peptides, survivin peptide variants or survivin peptide functional equivalents disclosed in WO 2004/067023 and WO 2006/081826.

In another embodiment, the vaccine of the invention may include one or more of a survivin peptide, survivin peptide variant or survivin peptide functional equivalent having the ability to bind any of the MHC Class I molecules selected from HLA-A, HLA-B or HLA-C moelcules.

Exemplary MHC Class I HLA-A molecules to which the survivin peptide, survivin peptide variant, or survivin peptide functional equivalent may bind include, without limitation, HLA-A1, HLA-A2, HLA-A3, HLA-A9, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, and HLA-A69.

Exemplary MHC Class I HLA-B molecules to which the survivin peptide, survivin peptide variant, or survivin peptide functional equivalent may bind include, without limitation, HLA-B5, HLA-B7, HLA-B8, HLA-B12, HLA-B13, HLA-B14, HLA-B15, HLA-B16, HLA-B17, HLA-B18, HLA-B21, HLA-B22, HLA-B27, HLA-B35, HLA-B37, HLA-B38, HLA-B39, HLA-B40, HLA-B41, HLA-B42, HLA-B44, HLA-B45, HLA-B46 and HLA-B47.

Exemplary MHC Class I HLA-C molecules to which the survivin peptide, survivin peptide variant, or survivin peptide functional equivalent may bind include, without limitation, HLA-C1, HLA-C2, HLA-C3, HLA-C4, HLA-05, HLA-C6, HLA-C7 and HLA-C16.

In a particular embodiment, the vaccine of the invention may comprise one or more of the survivin peptide antigens selected from:

| i) | FEELTLGEF | (SEQ ID NO: 1) | [HLA-A1] |
|---|---|---|---|
| ii) | FTELTLGEF | (SEQ ID NO: 2) | [HLA-A1] |
| iii) | LTLGEFLKL | (SEQ ID NO: 3) | [HLA-A2] |
| iv) | LMLGEFLKL | (SEQ ID NO: 4) | [HLA-A2] |
| v) | RISTFKNWPF | (SEQ ID NO: 5) | [HLA-A3] |
| vi) | RISTFKNWPK | (SEQ ID NO: 6) | [HLA-A3] |
| vii) | STFKNWPFL | (SEQ ID NO: 7) | [HLA-A24] |
| viii) | LPPAWQPFL | (SEQ ID NO: 8) | [HLA-B7] |

The above-listed survivin peptides represent, without limitation, exemplary MHC Class I restricted peptides encompassed by the invention. The specific MHC Class I HLA molecule to which each of the survivin peptides is believed to bind is shown on the right in square brackets. A vaccine of the invention may comprise one or more of these survivin peptides, in any suitable combination.

In a further embodiment, the vaccine of the invention comprises any one or more of the five survivin peptides listed below, in any suitable combination:

| i) | FTELTLGEF | (SEQ ID NO: 2) | [HLA-A1] |
|---|---|---|---|
| ii) | LMLGEFLKL | (SEQ ID NO: 4) | [HLA-A2] |
| iii) | RISTFKNWPK | (SEQ ID NO: 6) | [HLA-A3] |
| iv) | STFKNWPFL | (SEQ ID NO: 7) | [HLA-A24] |
| v) | LPPAWQPFL | (SEQ ID NO: 8) | [HLA-B7] |

In a particular embodiment, the composition of the invention comprises all five of the survivin peptide antigens listed above, as found in Immunovaccine Inc's or any combination or one or more of the peptide antigens. In a preferred embodiment, the composition will comprise all five of the survivin peptide antigen, candidate anti-cancer immunotherapeutic vaccine DPX-Survivac.

In addition to the at least one survivin antigen, further embodiments of the vaccine of the invention may comprise one or more additional antigen useful in the treatment of cancer or useful in inducing or potentiating an immune response against cancer. Exemplary embodiments of such additional antigens are described below.

(ii) Additional Antigens

Other antigens that may be useful in the compositions of the invention include, without limitation, antigens that are capable of inducing or potentiating an immune response in a subject that would be beneficial in the treatment of cancer, e.g. a cell-mediated immune response.

Cell-mediated immunity is an immune response that does not involve antibodies but rather involves the activation of macrophages and natural killer cells, the production of antigen-specific cytotoxic T lymphocytes and the release of various cytokines in response to an antigen. Cytotoxic T lymphocytes are a sub-group of T lymphocytes (a type of white blood cell) which are capable of inducing the death of infected somatic or tumor cells; they kill cells that are infected with viruses (or other pathogens), or are otherwise damaged or dysfunctional.

Most cytotoxic T cells express T-cell receptors that can recognise a specific peptide antigen bound to Class I MHC molecules. These CTLs also express CD8 (CD8+ T cells), which is attracted to portions of the Class I MHC molecule. This affinity keeps the CTL and the target cell bound closely together during antigen-specific activation.

Cellular immunity protects the body by, for example, activating antigen-specific cytotoxic T-lymphocytes that are able to lyse body cells displaying epitopes of foreign antigen on their surface, such as virus-infected cells, cells with intracellular bacteria, and cancer cells displaying tumor antigens; activating macrophages and natural killer cells, enabling them to destroy intracellular pathogens; and stimulating cells to secrete a variety of cytokines that influence the function of other cells involved in adaptive immune responses and innate immune responses.

Accordingly, in further embodiments, the vaccine compositions of the invention may comprise an additional antigen to the one or more survivin antigens. For example, the additional antigen may be, without limitation, a peptide, a suitable native, non-native, recombinant or denatured protein or polypeptide, or a fragment thereof, or an epitope that is capable of inducing or potentiating a CTL immune response in a subject.

The additional antigen may also be a polynucleotide that encodes the polypeptide that functions as an antigen. Nucleic acid-based vaccination strategies are known, wherein a vaccine composition that contains a polynucleotide is administered to a subject. The antigenic polypeptide encoded by the polynucleotide is expressed in the subject, such that the antigenic polypeptide is ultimately present in the subject, just as if the vaccine composition itself had contained the polypeptide. For the purposes of the present invention, the additional antigen, where the context dictates, encompasses such polynucleotides that encode the polypeptide which functions as the antigen.

The term "polypeptide" encompasses any chain of amino acids, regardless of length (e.g., at least 6, 8, 10, 12, 14, 16, 18, or 20 amino acids) or post-translational modification (e.g., glycosylation or phosphorylation), and includes, for example, natural proteins, synthetic or recombinant polypeptides and peptides, epitopes, hybrid molecules, variants, homologs, analogs, peptoids, peptidomimetics, etc. A variant or derivative therefore includes deletions, including truncations and fragments; insertions and additions, for example conservative substitutions, site-directed mutants and allelic variants; and modifications, including peptoids having one or more non-amino acyl groups (for example, sugar, lipid, etc.) covalently linked to the peptide and post-translational modifications. As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |

-continued

| Original Residue | Conservative Substitutions |
| --- | --- |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Polypeptides or peptides that have substantial identity to a preferred antigen sequence may be used. Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, 99% identity over a specified region. The term "identity" refers to sequence similarity between two polypeptides molecules. Identity can be determined by comparing each position in the aligned sequences. A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, available at http://clustalw.qenome.ad.ip, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85:2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). For example, the "BLAST 2 Sequences" tool, available through the National Center for Biotechnology Information (through the internet at http://www.ncbi.nlm.nih.gov/BLAST/bl2seq/wblast2.cgi) may be used, selecting the "blastp" program at the following default settings: expect threshold 10; word size 3; matrix BLOSUM 62; gap costs existence 11, extension 1. In another embodiment, the person skilled in the art can readily and properly align any given sequence and deduce sequence identity and/or homology by mere visual inspection.

Polypeptides and peptides used as an additional antigen in the vaccine of the invention can be isolated from natural sources, be synthetic, or be recombinantly generated polypeptides. Peptides and proteins can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K, Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

In some embodiments, the additional antigen may be a purified antigen, e.g., from about 25% to 50% pure, from about 50% to about 75% pure, from about 75% to about 85% pure, from about 85% to about 90% pure, from about 90% to about 95% pure, from about 95% to about 98% pure, from about 98% to about 99% pure, or greater than 99% pure.

As noted above, the additional antigen includes a polynucleotide that encodes the polypeptide that functions as the antigen. As used herein, the term "polynucleotide" encompasses a chain of nucleotides of any length (e.g. 9, 12, 18, 24, 30, 60, 150, 300, 600, 1500 or more nucleotides) or number of strands (e.g. single-stranded or double-stranded). Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

The polynucleotide may be delivered in various forms. In some embodiments, a naked polynucleotide may be used, either in linear form, or inserted into a plasmid, such as an expression plasmid. In other embodiments, a live vector such as a viral or bacterial vector may be used.

One or more regulatory sequences that aid in transcription of DNA into RNA and/or translation of RNA into a polypeptide may be present. In some instances, such as in the case of a polynucleotide that is a messenger RNA (mRNA) molecule, regulatory sequences relating to the transcription process (e.g. a promoter) are not required, and protein expression may be effected in the absence of a promoter. The skilled artisan can include suitable regulatory sequences as the circumstances require.

In some embodiments, the polynucleotide is present in an expression cassette, in which it is operably linked to regulatory sequences that will permit the polynucleotide to be expressed in the subject to which the composition of the invention is administered. The choice of expression cassette depends on the subject to which the composition is administered as well as the features desired for the expressed polypeptide.

Typically, an expression cassette includes a promoter that is functional in the subject and can be constitutive or inducible; a ribosome binding site; a start codon (ATG) if necessary; the polynucleotide encoding the polypeptide of interest; a stop codon; and optionally a 3' terminal region (translation and/or transcription terminator). Additional sequences such as a region encoding a signal peptide may be included. The polynucleotide encoding the polypeptide of interest may be homologous or heterologous to any of the other regulatory sequences in the expression cassette. Sequences to be expressed together with the polypeptide of interest, such as a signal peptide encoding region, are typically located adjacent to the polynucleotide encoding the protein to be expressed and placed in proper reading frame. The open reading frame constituted by the polynucleotide encoding the protein to be expressed solely or together with any other sequence to be expressed (e.g. the signal peptide), is placed under the control of the promoter so that transcription and translation occur in the subject to which the composition is administered.

The amount of an additional antigen used in a single treatment with a vaccine composition as described herein may vary depending on the type of antigen and the size of the subject. One skilled in the art will be able to determine, without undue experimentation, the effective amount of an additional antigen to use in a particular application. The term "effective amount" as used herein means an amount effective, at dosages and for periods of time necessary, to achieve the desired result.

In some embodiments, the additional antigen may be at least one CTL epitope capable of inducing a CTL response. For example, the additional antigen may be a CTL epitope derived from a protein identified as being up-regulated in cancer cells.

In an embodiment, the CTL epitope may be an epitope of a tumor-associated protein, such as for example, a melanoma-associated protein. In some embodiments, the melanoma-associated protein is a tyrosine related protein-2 (TRP-2) or p53, which can be obtained by various methods including recombinant technology or chemical synthesis.

The following genes, without limitation, code for tumor-associated proteins that have peptide sequences that can be incorporated as an additional antigens in the vaccine of the invention: p53, HPV E6 and E7, ART-4, CAMEL, CEA, Cyp-B, HER2/neu, hTERT, hTRT, iCE, MUC1, MUC2, PRAME, P15, RUI, RU2, SART-1, SART-3, WT1, PSA, tyrosinase, TRP-1, TRP-2, gp100, MART-1/Melan A, MAGE-A1, MAGE-A2, MAGE-A3, MAGE-A6, MAGE-A10, MAGE-A12, BALE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a (CAG-3), AFP, β-catenin/m, Caspase-8/m, CDK-4/m, ELF2M, GnT-V, G250, Ras, HSP70-2M, HST-2, KIAA0205, MUM-1, MUM-2, MUM-3, Myosin/m, RAGE, SART-2, survivin, TRP-2/INT2, and 707-AP.

In an embodiment, the vaccine may comprise a mixture of CTL epitopes associated with cancer as antigens for inducing a CTL response. For example, the antigen may comprise at least one or more of a survivin antigen as described herein, such as for example and without limitation, survivin peptide antigens having the following amino acid sequences: FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); and LPPAWQPFL (SEQ ID NO: 8), together with at least one additional antigen of a tumor-associated protein.

(iii) T-Helper Epitope

In some embodiments, the vaccine of the invention comprises at least one T-helper epitope or T-helper antigen.

T-helper epitopes are a sequence of amino acids (natural or non-natural amino acids) that have T-helper activity. T-helper epitopes are recognised by T-helper lymphocytes, which play an important role in establishing and maximising the capabilities of the immune system, and are involved in activating and directing other immune cells, such as for example cytotoxic T lymphocytes.

A T-helper epitope can consist of a continuous or discontinuous epitope. Hence not every amino acid of a T-helper is necessarily part of the epitope. Accordingly, T-helper epitopes, including analogs and segments of T-helper epitopes, are capable of enhancing or stimulating an immune response. Immunodominant T-helper epitopes are broadly reactive in animal and human populations with widely divergent MHC types (Celis et al. (1988) *J. Immunol.* 140:1808-1815; Demotz et al. (1989) *J. Immunol.* 142:394-402; Chong et al. (1992) *Infect. Immun.* 60:4640-4647). The T-helper domain of the subject peptides has from about 10 to about 50 amino acids and preferably from about 10 to about 30 amino acids. When multiple T-helper epitopes are present, then each T-helper epitope acts independently.

In some embodiments, the T-helper epitope may form part of an antigen described herein. In particular, if the antigen is of sufficient size, it may contain an epitope that functions as a T-helper epitope. In other embodiments, the T-helper epitope is a separate molecule from the antigen.

In another embodiment, T-helper epitope analogs may include substitutions, deletions and insertions of from one to about 10 amino acid residues in the T-helper epitope. T-helper segments are contiguous portions of a T-helper epitope that are sufficient to enhance or stimulate an immune response. An example of T-helper segments is a series of overlapping peptides that are derived from a single longer peptide.

In a particular embodiment, the compositions of the invention may comprise as a T-helper epitope or antigen, the modified Tetanus toxin peptide A16L (830 to 844; AQYIKANSKFIGITEL (SEQ ID NO: 9), with an alanine residue added to its amino terminus to enhance stability (Slingluff et al., Clin Cancer Res., 7: 3012-3024, 2001).

Other sources of T-helper epitopes which may be used in the present compositions include, for example, hepatitis B surface antigen helper T cell epitopes, pertussis toxin helper T cell epitopes, measles virus F protein helper T cell epitope, *Chlamydia trachomitis* major outer membrane protein helper T cell epitope, diphtheria toxin helper T cell epitopes, *Plasmodium falciparum* circumsporozoite helper T cell epitopes, *Schistosoma mansoni* triose phosphate isomerase helper T cell epitopes, *Escherichia coli* TraT helper T cell epitopes and immune-enhancing analogs and segments of any of these T-helper epitopes.

In some embodiments, the T-helper epitope may be a universal T-helper epitope. A universal T-helper epitope as used herein refers to a peptide or other immunogenic molecule, or a fragment thereof, that binds to a multiplicity of MHC class II molecules in a manner that activates T-cell function in a class II (CD4+ T cells)-restricted manner. An example of a universal T-helper epitope is PADRE (pan-DR epitope) comprising the peptide sequence AKXVAAWTL-KAAA (SEQ ID NO: 12), wherein X may be cyclohexylalanyl. PADRE specifically has a CD4+ T-helper epitope, that is, it stimulates induction of a PADRE-specific CD4+ T-helper response.

In addition to the modified tetanus toxin peptide A16L mentioned earlier, Tetanus toxoid has other T-helper epitopes that work in the similar manner as PADRE. Tetanus and diphtheria toxins have universal epitopes for human CD4+ cells (Diethelm-Okita, B. M. et al., *J. Infect. Diseases,* 181:1001-1009, 2000). In another embodiment, the T-helper epitope may be a tetanus toxoid peptide such as F21E comprising the peptide sequence FNNFTVSFWLRVPK-VSASHLE (amino acids 947-967; SEQ ID NO: 13).

In certain embodiments, the T-helper epitope is fused to at least one of the one or more survivin antigens in the vaccine of the invention or to the additional antigen which may be included in the vaccine (e.g. a fusion peptide).

(iv) Adjuvants

In some embodiments, the vaccine of the invention comprises one or more pharmaceutically acceptable adjuvants. A large number of adjuvants have been described and are known to those skilled in the art. See, for example, Remington's Pharmaceutical Sciences (Remington's Pharmaceutical Sciences, Mack Publishing Company, Easton, Pa., USA 1985) and The United States Pharmacopoeia: The National Formulary (USP 24 NF19) published in 1999.

Exemplary adjuvants include, without limitation, alum, other compounds of aluminum, *Bacillus* of Calmette and Guerin (BCG), TiterMax™, Ribi™, Freund's Complete Adjuvant (FCA), CpG-containing oligodeoxynucleotides (CpG ODN), lipopeptides and polyI:C polynucleotides. An exemplary CpG ODN is 5 '-TCCATGACGTTCCT GACGTT-3' (SEQ ID NO: 14). The skilled person can readily select other appropriate CpG ODNs on the basis of the target species and efficacy. An exemplary lipopeptide includes, without limitation, Pam3Cys-SKKK (EMC Microcollections, Germany) or variants, homologs and analogs thereof. The Pam2 family of lipopeptides has been shown to be an effective alternative to the Pam3 family of lipopeptides.

In a particular embodiment, the vaccine comprises a polyI:C polynucleotide as an adjuvant, such as for example and without limitation, a 26 mer deoxy inosine/cytosine synthetic polynucleotide.

As used herein, a "polyI:C" or "polyI:C polynucleotide" is a double-stranded polynucleotide molecule (RNA or DNA or a combination of DNA and RNA), each strand of which contains at least 6 contiguous inosinic or cytidylic acid residues, or 6 contiguous residues selected from inosinic acid and cytidylic acid in any order (e.g. IICIIC, ICICIC or IIICCC), and which is capable of inducing or enhancing the production of at least one inflammatory cytokine, such as interferon, in a mammalian subject. PolyI:C polynucleotides will typically have a length of about 8, 10, 12, 14, 16, 18, 20, 22, 24, 25, 28, 30, 35, 40, 45, 50, 55, 60, 65, 70, 75, 80, 85, 90, 95, 100, 150, 200, 250, 300, 500, 1000 or more residues. The upper limit is not believed to be essential. Preferred polyI:C polynucleotides may have a minimum length of about 6, 8, 10, 12, 14, 16, 18, 20, 22, 24, 26, 28, or 30 nucleotides and a maximum length of about 1000, 500, 300, 200, 100, 90, 80, 70, 60, 50, 45 or 40 nucleotides.

Each strand of a polyI:C polynucleotide may be a homopolymer of inosinic or cytidylic acid residues, or each strand may be a heteropolymer containing both inosinic and cytidylic acid residues. In either case, the polymer may be interrupted by one or more non-inosinic or non-cytidylic acid residues (e.g. uridine), provided there is at least one contiguous region of 6 I, 6 C or 6 I/C residues as described above. Typically, each strand of a polyI:C polynucleotide will contain no more than 1 non-I/C residue per 6 I/C residues, more preferably, no more than 1 non-I/C residue per every 8, 10, 12, 14, 16, 18, 20, 22, 24, 26, 28 or 30 I/C residues.

The inosinic acid or cytidylic acid (or other) residues in the polyI:C polynucleotide may be derivatized or modified as is known in the art, provided the ability of the polyI:C polynucleotide to promote the production of an inflammatory cytokine, such as interferon, is retained. Non-limiting examples of derivatives or modifications include e.g. azido modifications, fluoro modifications, or the use of thioester (or similar) linkages instead of natural phosphodiester linkages to enhance stability in vivo. The polyI:C polynucleotide may also be modified to e.g. enhance its resistance to degradation in vivo by e.g. complexing the molecule with positively charged poly-lysine and carboxymethylcellulose, or with a positively charged synthetic peptide.

The polyI:C polynucleotide will typically be included in the compositions of the invention in an amount from about 0.001 mg to 1 mg per unit dose of the composition. In certain embodiments, the amount of polyI:C polynucleotide will be about 0.04 mg/mL of the vaccine composition.

Other suitable adjuvants of the vaccine are those that activate or increase the activity of TLR2. As used herein, an adjuvant which "activates" or "increases the activity" of a TLR includes any adjuvant, in some embodiments a lipid-based adjuvant, which acts as a TLR agonist. Further, activating or increasing the activity of TLR2 encompasses its activation in any monomeric, homodimeric or heterodimeric form, and particularly includes the activation of TLR2 as a heterodimer with TLR1 or TLR6 (i.e. TLR1/2 or TLR2/6).

An exemplary embodiment of an adjuvant that activates or increases the activity of TLR2 is a lipid-based adjuvant that comprises at least one lipid moiety or lipid component.

As used herein, the expression "lipid moiety" or "lipid component" refers to any fatty acid (e.g. fatty acyls) or derivative thereof, including for example triglycerides, diglycerides, and monoglycerides. Exemplary fatty acids include, without limitation, palmitoyl, myristoyl, stearoyl and decanoyl groups or any C2 to C30 saturated or unsaturated fatty acyl group, preferably any C14 to C22 saturated or unsaturated fatty acyl group, and more preferably a C16 saturated or unsaturated fatty acyl group. Thus, as referred to herein, the expression "lipid-based adjuvant" encompasses any adjuvant comprising a fatty acyl group or derivative thereof.

Lipid-based adjuvants contain at a minimum at least one lipid moiety, or a synthetic/semi-synthetic lipid moiety analogue, which can be coupled onto an amino acid, an oligopeptide or other molecules (e.g. a carbohydrate, a glycan, a polysaccharide, biotin, Rhodamine, etc.). Thus, without limitation, the lipid-based adjuvant may be, for example, a lipoamino acid, a lipopeptide, a lipoglycan, a lipopolysaccharide or a lipoteichoic acid. Moreover, a lipid moiety or a structure containing a lipid moiety can be coupled covalently or non-covalently to an antigen to create antigenic compounds with built-in adjuvanting properties. For example, and without limitation, the lipid-based moiety may comprise a cation (e.g. nickel) to provide a positive charge for non-covalent coupling.

In some embodiments, the lipid moiety or lipid component may be naturally occurring, such as for example a cell-wall component (e.g. lipoprotein) from a Gram-positive or Gram-negative bacteria, *Rhodopseudomonas viridis*, or *mycoplasma*. In other embodiments, the lipid moiety or lipid component may be synthetic or semi-synthetic.

The lipid-based adjuvant may comprise palmitic acid (PAM) as at least one of the lipid moieties or components of the adjuvant. Such lipid-based adjuvants are referred to herein as a "palmitic acid adjuvant". Palmitic acid is a low molecular weight lipid found in the immunologically reactive Braun's lipoprotein of *Escherichia coli*. Other common chemical names for palmitic acid include, for example, hexadecanoic acid in IUPAC nomenclature and 1-Pentadecanecarboxylic acid. The molecular formula of palmitic acid is $CH_3(CH_2)_{14}CO_2H$. As will be understood to those skilled in the art, it is possible that the lipid chain of palmitic acid may be altered. Exemplary compounds which may be used herein as palmitic acid adjuvants, and methods for their synthesis, are described for example in United States Patent Publications US 2008/0233143; US 2010/0129385; and US 2011/0200632.

As described above for lipid moieties generally, a palmitic acid adjuvant contains at a minimum at least one palmitic acid moiety, which can be coupled onto an amino acid, an oligopeptide or other molecules. A palmitic acid moiety or a structure containing palmitic acid can be coupled covalently or non-covalently to an antigen to create antigenic compounds with built-in adjuvanting properties. The palmitic acid moiety or a chemical structure containing palmitic acid can be conjugated to a cysteine peptide (Cys) to allow for various structural configurations of the adjuvant, including linear and branched structures. The cysteine residue has been commonly extended by polar residues such as Serine (Ser) and/or lysine (Lys) at the C terminus to create adjuvant compounds with improved solubility. Palmitic acid containing adjuvant compounds could be admixed with an antigen, associated with antigen through non-covalent interactions, or alternatively covalently linked to an antigen, either directly or with the use of a linker/spacer, to generate enhanced immune responses. Most commonly, two palmitic acid moieties are attached to a glyceryl backbone and a cysteine residue to create dipalmitoyl-S-glyceryl-cysteine ($PAM_2Cys$) or tripalmitoyl-S-glyceryl-cysteine ($PAM_3Cys$), which can also be used in multiple configurations as described above.

Therefore, in an embodiment, the adjuvant of the composition may comprise a palmitic acid moiety or component. The palmitic acid moiety may be modified or manipulated to improve its stability in vitro or in vivo, enhance its binding to receptors (such as for example toll-like receptors as described below) or enhance its biological activity.

In a particular embodiment, the palmitic acid adjuvant may comprise $PAM_2Cys$ or $PAM_3Cys$. In another particular embodiment, the palmitic acid adjuvant may be Pam-2-Cys-Ser-(Lys)4 or Pam-3-Cys-Ser-(Lys)4. Such palmitic acid adjuvants are available, for example, as research reagents from EMC Microcollections GmbH (Germany) and InvivoGen (San Diego, Calif., USA). Also available from EMC Microcollections are various analogs of Pam-2-Cys-Ser-(Lys)4 and Pam-3-Cys-Ser-(Lys)4, including labelled analogs.

The composition of the invention may comprise an adjuvant as described above in combination with at least one other suitable adjuvant. Exemplary embodiments of the at least one other adjuvant encompasses, but is by no means limited to, organic and inorganic compounds, polymers, proteins, peptides, sugars from synthetic, non-biological or biological sources (including but not limited to virosomes, virus-like particles, viruses and bacteria of their components).

Further examples of compatible adjuvants may include, without limitation, chemokines, Toll like receptor agonists, colony stimulating factors, cytokines, 1018 ISS, aluminum salts, Amplivax, AS04, AS15, ABM2, Adjumer, Algammulin, AS01B, AS02 (SBASA), ASO2A, BCG, Calcitriol, Chitosan, Cholera toxin, CP-870,893, CpG, polyIC, CyaA, Dimethyldioctadecylammonium bromide (DDA), Dibutyl phthalate (DBP), dSLIM, Gamma inulin, GM-CSF, GMDP, Glycerol, IC30, IC31, Imiquimod, ImuFact IMP321, IS Patch, ISCOM, ISCOMATRIX, JuvImmune, LipoVac, LPS, lipid core protein, MF59, monophosphoryl lipid A, Montanide® IMS1312, Montanide® based adjuvants, OK-432, OM-174, OM-197-MP-EC, ONTAK, PepTel vector system, other palmitoyl based molecules, PLG microparticles, resiquimod, squalene, SLR172, YF-17 DBCG, QS21, QuilA, P1005, Poloxamer, Saponin, synthetic polynucleotides, Zymosan, pertussis toxin.

Accordingly, the composition may comprise one or more pharmaceutically acceptable adjuvants. In some embodiments, at least one of the one or more survivin antigens or the additional antigen may be coupled to at least one of the adjuvants.

The amount of adjuvant used depends on the amount of antigen and on the type of adjuvant. One skilled in the art can readily determine the amount of adjuvant needed in a particular application by empirical testing.

(v) Liposomes

In some embodiments, the vaccine of the invention comprises liposomes. In a particular embodiment, liposomes are included when the vaccine compositions comprise a carrier comprising a continuous phase of a hydrophobic substance as described herein.

Liposomes represent a particular embodiment of an adjuvanting system encompassed by the present invention. However, the vaccines of the invention may not include liposomes. Rather, in other embodiments of the vaccines, the one or more survivin antigens may be combined with any suitable adjuvant for delivery of the survivin antigen to a subject.

Liposomes are completely closed lipid bilayer membranes containing an entrapped aqueous volume. Liposomes may be unilamellar vesicles (possessing a single bilayer membrane) or multilamellar vesicles characterized by multimembrane bilayers, each bilayer may or may not be separated from the next by an aqueous layer. A general discussion of liposomes can be found in Gregoriadis G. *Immunol. Today,* 11:89-97, 1990; and Frezard, F., *Braz. J. Med. Bio. Res.,* 32:181-189, 1999. As used herein and in the claims, the term "liposomes" is intended to encompass all such vesicular structures as described above, including, without limitation, those described in the art as "niosomes", "transfersomes" and "virosomes".

Although any liposomes may be used in this invention, including liposomes made from archaebacterial lipids, particularly useful liposomes use phospholipids and unesterified cholesterol in the liposome formulation. The cholesterol is used to stabilize the liposomes and any other compound that stabilizes liposomes may replace the cholesterol. Other liposome stabilizing compounds are known to those skilled in the art. For example, saturated phospholipids produce liposomes with higher transition temperatures indicating increased stability.

Phospholipids that are preferably used in the preparation of liposomes are those with at least one head group selected from the group consisting of phosphoglycerol, phosphoethanolamine, phosphoserine, phosphocholine (e.g. DOPC; 1,2-Dioleoyl-sn-glycero-3-phosphocholine) and phosphoinositol. More preferred are liposomes that comprise lipids which are 94-100% phosphatidylcholine. Such lipids are available commercially in the lecithin Phospholipon® 90 G. When unesterified cholesterol is also used in liposome formulation, the cholesterol is used in an amount equivalent to about 10% of the weight of phospholipid. If a compound other than cholesterol is used to stabilize the liposomes, one skilled in the art can readily determine the amount needed in the composition.

Liposome compositions may be obtained, for example, by using natural lipids, synthetic lipids, sphingolipids, ether lipids, sterols, cardiolipin, cationic lipids and lipids modified with poly (ethylene glycol) and other polymers. Synthetic lipids may include the following fatty acid constituents; lauroyl, myristoyl, palmitoyl, stearoyl, arachidoyl, oleoyl, linoleoyl, erucoyl, or combinations of these fatty acids.

(vi) Carriers

In some embodiments, the vaccine of the invention comprises a pharmaceutically acceptable carrier, excipient or diluent. As used herein, a pharmaceutically acceptable carrier refers to any substance suitable for delivering a vaccine composition of the invention, and which is useful in the method of the present invention.

Carriers that can be used with vaccines of the invention are well known in the art, and include, but are by no means limited to, e.g., water, phosphate buffered saline, Ringer's solution, dextrose solution, serum-containing solutions, Hank's solution, other aqueous physiologically balanced solutions, oil-in-water emulsions, oils, water-in-oil emulsions, esters, poly(ethylene-vinyl acetate), copolymers of lactic acid and glycolic acid, polylactic acid), gelatin, collagen matrices, polysaccharides, poly(D,L lactide), poly (malic acid), poly(caprolactone), celluloses, albumin, starch, casein, dextran, polyesters, ethanol, mathacrylate, polyurethane, polyethylene, vinyl polymers, glycols, thyroglobulin, albumins such as human serum albumin, tetanus toxoid, polyamino acids such as poly L-lysine, poly L-glutamic acid, influenza, hepatitis B virus core protein, mixtures thereof and the like. See, for example, Remington: The Science and Practice of Pharmacy, 2000, Gennaro, A R ed., Eaton, Pa.: Mack Publishing Co.

In a particular embodiment, the carrier of the vaccine composition is a carrier that comprises a continuous phase of a hydrophobic substance, preferably a liquid hydrophobic substance. The continuous phase may be an essentially pure hydrophobic substance or a mixture of hydrophobic substances. In addition, the carrier may be an emulsion of water in a hydrophobic substance or an emulsion of water in a mixture of hydrophobic substances, provided the hydrophobic substance constitutes the continuous phase. Further, in another embodiment, the carrier may function as an adjuvant.

Hydrophobic substances that are useful in the compositions as described herein are those that are pharmaceutically and/or immunologically acceptable. The carrier is preferably a liquid but certain hydrophobic substances that are not liquids at atmospheric temperature may be liquefied, for example by warming, and are also useful in this invention. In one embodiment, the hydrophobic carrier may be a Phosphate Buffered Saline/Freund's Incomplete Adjuvant (PBS/FIA) emulsion.

Oil or water-in-oil emulsions are particularly suitable carriers for use in the vaccine composition of the invention. Oils should be pharmaceutically and/or immunologically acceptable. Suitable oils include, for example, mineral oils (especially light or low viscosity mineral oil such as Drakeol® 6VR), vegetable oils (e.g., soybean oil), nut oils (e.g., peanut oil), or mixtures thereof. Thus, in a particular embodiment the carrier is a hydrophobic substance such as vegetable oil, nut oil or mineral oil. Animal fats and artificial hydrophobic polymeric materials, particularly those that are liquid at atmospheric temperature or that can be liquefied relatively easily, may also be used.

To enhance immunogenicity of cancer vaccines, Immunovaccine Inc. has developed an adjuvanting vaccine platform designed to facilitate a strong and robust immune response to peptide antigens. DepoVax™ (DPX) is a liposome-in-oil formulation, including a TLR-adjuvant and universal T-helper peptide, that can be formulated with any epitope, or mixture of epitopes, to induce a cytotoxic T lymphocyte-mediated immune response (Karkada et al., *J Immunother* 33(3):250-261, 2010) and/or a humoral immune response. DPX forms a strong depot at the site of immunization which prolongs antigen exposure to the immune system.

It has been shown that a single vaccination with peptides in DPX results in equivalent or better immune responses than multiple vaccinations with peptides in other conventional formulations, such as Montanide ISA51 VG emulsions, similar to VacciMax which was a first generation emulsion-based vaccine platform (Daftarian et al., *J Transl Med* 5: 26, 2007; Mansour et al., *J Transl Med* 5: 20, 2007). A DepoVax™ based peptide-vaccine called DPX-0907 has recently completed a phase I clinical trial in breast, ovarian and prostate cancer patients demonstrating safety and immunogenicity in these advanced patients (Berinstein et al., *J Transl Med* 10(1): 156, 2012).

Thus, in a particular embodiment, the carrier of the vaccine of the invention may be Immunovaccine, Inc's liposomal-based adjuvanting system. Unlike water-in-oil emulsion based vaccines, which rely on oil entrapping water droplets containing antigen and adjuvant, DepoVax™ based formulations rely on liposomes to facilitate the incorporation of antigens and adjuvants directly into the oil, without the need for emulsification. Advantages of this approach include: (1) enhancing the solubility of hydrophilic antigens/adjuvant in oil diluents which otherwise would normally have maximum solubility in aqueous based diluents, and (2) the elimination of cumbersome emulsification procedures prior to vaccine administration.

In a preferred embodiment, the carrier is mineral oil or is a mannide oleate in mineral oil solution, such as that commercially available as Montanide® ISA 51 (SEPPIC, France).

In certain embodiments, the compositions may be substantially free of water (e.g., "water-free"). It is possible that the hydrophobic carrier of these "water-free" compositions may still contain small quantities of water, provided that the water is present in the non-continuous phase of the carrier. For example, individual components of the composition may have bound water that may not be completely removed by processes such as lyophilization or evaporation and certain hydrophobic carriers may contain small amounts of water dissolved therein. Generally, compositions of the invention that are "water-free" contain, for example, less than about 10%, 9%, 8%, 7%, 6%, 5%, 4%, 3%, 2%, 1%, 0.5%, 0.1%, 0.05% or 0.01% water on a weight/weight basis of the total weight of the carrier component of the composition.

Methods of Preparing Exemplary Vaccine Compositions

In a particular embodiment, the vaccine composition of the invention is one that comprises at least one survivin antigen, liposomes and a carrier comprising a continuous phase of a hydrophobic substance.

Methods for making liposomes are well known in the art. See e.g. Gregoriadis (1990) and Frezard (1999) both cited previously. Any suitable method for making liposomes may be used in the practice of the invention, or liposomes may be obtained from a commercial source. Liposomes are typically prepared by hydrating the liposome components that will form the lipid bilayer (e.g. phospholipids and cholesterol) with an aqueous solution, which may be pure water or a solution of one or more components dissolved in water, e.g. phosphate-buffered saline (PBS), phosphate-free saline, or any other physiologically compatible aqueous solution.

In an embodiment, a liposome component or mixture of liposome components, such as a phospholipid (e.g. Phospholipon® 90G) or DOPC and cholesterol, may be solubilized in an organic solvent, such as a mixture of chloroform and methanol, followed by filtering (e.g. a PTFE 0.2 μm filter) and drying, e.g. by rotary evaporation, to remove the solvents.

Hydration of the resulting lipid mixture may be effected by e.g. injecting the lipid mixture into an aqueous solution or sonicating the lipid mixture and an aqueous solution. During formation of liposomes, the liposome components form single bilayers (unilamellar) or multiple bilayers (multilamellar) surrounding a volume of the aqueous solution with which the liposome components are hydrated.

In some embodiments, the liposomes are then dehydrated, such as by freeze-drying or lyophilization.

The liposomes are combined with an appropriate carrier, such as a carrier comprising a continuous hydrophobic phase. This can be done in a variety of ways.

If the carrier is composed solely of a hydrophobic substance or a mixture of hydrophobic substances (e.g. use of a 100% mineral oil carrier), the liposomes may simply be mixed with the hydrophobic substance, or if there are multiple hydrophobic substances, mixed with any one or a combination of them.

If instead the carrier comprising a continuous phase of a hydrophobic substance contains a discontinuous aqueous phase, the carrier will typically take the form of an emulsion of the aqueous phase in the hydrophobic phase, such as a water-in-oil emulsion. Such compositions may contain an emulsifier to stabilize the emulsion and to promote an even distribution of the liposomes. In this regard, emulsifiers may be useful even if a water-free carrier is used, for the purpose of promoting an even distribution of the liposomes in the carrier. Typical emulsifiers include mannide oleate (Arlacel™ A), lecithin (e.g. S100 lecithin), a phospholipid, Tween™ 80, and Spans™ 20, 80, 83 and 85. Typically, the volume ratio (v/v) of hydrophobic substance to emulsifier is in the range of about 5:1 to about 15:1 with a ratio of about 10:1 being preferred.

The liposomes may be added to the finished emulsion, or they may be present in either the aqueous phase or the hydrophobic phase prior to emulsification.

The survivin antigen(s) or an additional antigen as described herein may be introduced at various different stages of the formulation process. More than one type of antigen may be incorporated into the composition. As used in this section, the term "antigen" is used generally and can refer to a survivin antigen as described herein, one or more survivin antigens, an additional antigen as described herein or one or more additional antigens, or any combination thereof. The term is used generally to describe how any antigen may be formulated in the vaccine compositions of the invention. The term "antigen" encompasses both the singular form "antigen" and the plural "antigens". It is not necessary that all antigens be introduced into the vaccine composition in the same way.

In some embodiments, the antigen is present in the aqueous solution used to hydrate the components that are used to form the lipid bilayers of the liposomes (e.g. phospholipid(s) and cholesterol). In this case, the antigen will be encapsulated in the liposome, present in its aqueous interior. If the resulting liposomes are not washed or dried, such that there is residual aqueous solution present that is ultimately mixed with the carrier comprising a continuous phase of a hydrophobic substance, it is possible that additional antigen may be present outside the liposomes in the final product. In a related technique, the antigen may be mixed with the components used to form the lipid bilayers of the liposomes, prior to hydration with the aqueous solution. The antigen may also be added to pre-formed liposomes, in which case the antigen may be actively loaded into the liposomes, or bound to the surface of the liposomes or the antigen may remain external to the liposomes. In such embodiments, prior to the addition of antigen, the pre-formed liposomes may be empty liposomes (e.g. not containing encapsulated antigen or lipid-based adjuvant) or the pre-formed liposomes may contain lipid-based adjuvant incorporated into or associated with the liposomes. These steps may preferably occur prior to mixing with the carrier comprising a continuous phase of a hydrophobic substance.

In an alternative approach, the antigen may instead be mixed with the carrier comprising a continuous phase of a hydrophobic substance, before, during, or after the carrier is combined with the liposomes. If the carrier is an emulsion, the antigen may be mixed with either or both of the aqueous phase or hydrophobic phase prior to emulsification. Alternatively, the antigen may be mixed with the carrier after emulsification.

The technique of combining the antigen with the carrier may be used together with encapsulation of the antigen in the liposomes as described above, such that antigen is present both within the liposomes and in the carrier comprising a continuous phase of a hydrophobic substance.

The above-described procedures for introducing the antigen into the composition apply also to the T-helper epitope and/or the adjuvant of the compositions as described herein, in embodiments where they are included. That is, the T-helper epitope and/or adjuvant may be introduced into e.g. one or more of: (1) the aqueous solution used to hydrate the components that are used to form the lipid bilayers of the liposomes; (2) the aqueous solution after formation of the lipid bilayers of the liposomes; (3) the components used to form the lipid bilayers of the liposomes; or (4) the carrier comprising a continuous phase of a hydrophobic substance, before, during, or after the carrier is combined with the liposomes. If the carrier is an emulsion, the T-helper epitope and/or adjuvant may be mixed with either or both of the aqueous phase or hydrophobic phase before, during or after emulsification.

The technique of combining the T-helper epitope and/or adjuvant with the carrier may be used together with encapsulation of these components in the liposomes, or with addition of these components to the liposomes, such that T-helper epitope and/or adjuvant is present inside and/or outside the liposomes and in the carrier comprising a continuous phase of a hydrophobic substance.

The T-helper epitope and/or adjuvant can be incorporated in the composition together with the antigen at the same processing step, or separately, at a different processing step. For instance, the antigen, T-helper epitope and adjuvant may all be present in the aqueous solution used to hydrate the lipid bilayer-forming liposome components, such that all three components become encapsulated in the liposomes. Alternatively, the antigen and the T-helper epitope may be encapsulated in the liposomes, and the adjuvant mixed with the carrier comprising a continuous phase of a hydrophobic substance. In a further embodiment, the T-helper epitope and/or adjuvant may be incorporated into the composition after the antigen encapsulation step by passing the liposome-antigen preparation through a manual mini-extruder and then mixing the obtained liposome-antigen preparation with the lipid-based adjuvant in, for example, phosphate buffer. The T-helper epitope and/or adjuvant may also be incorporated into the composition, either alone or together with antigen, after the liposomes have been formed, such that the T-helper epitope and adjuvant may be associated or remain external to the liposomes. The T-helper epitope and/or adjuvant may also be incorporated into or associated with liposomes prior to addition of antigen, with the antigen remaining outside the pre-formed liposomes or loaded into/associated with the liposomes by further processing. In such embodiments, the resulting preparation may be lyophilized and then reconstituted in the carrier comprising a continuous phase of a hydrophobic substance. It will be appreciated that many such combinations are possible.

In a particular embodiment, the vaccine of the invention is DPX-Survivac. An exemplary method to prepare DPX-Survivac follows. However, it will be appreciated that alternate embodiments are also encompassed herein, such as those described above where the antigen, adjuvant and T-helper epitope may be introduced at any stage in the formulation of the vaccine, in any order and may ultimately be found inside, outside or both inside and outside the liposomes.

To prepare DPX-Survivac, in an exemplary method, a complex is formed with the five survivin antigens (SEQ ID Nos: 2, 4, 6, 7 and 8); adjuvant (polyI:C polynucleotide) and liposomes (DOPC and cholesterol) in an aqueous buffer by a process of mixing and hydrating lipid components in the presence of the survivin antigens and adjuvant, extruded to achieve a particle size that can be sterile filtered, then filled into vials and lyophilized to a dry cake. The dry cake is then re-suspended in the hydrophobic carrier Montanide ISA51 VG before injection. This exemplary method of preparation may be used with any combination of survivin antigens, any suitable adjuvant and any suitable T-helper epitope.

If the composition contains one or more further adjuvants, such additional adjuvants can be incorporated in the composition in similar fashion as described above for the adjuvant or by combining several of such methods as may be suitable for the additional adjuvant(s).

Stabilizers such as sugars, anti-oxidants, or preservatives that maintain the biological activity or improve chemical stability to prolong the shelf life of antigen, adjuvant, the liposomes or the continuous hydrophobic carrier, may be added to such compositions.

In some embodiments, an antigen/adjuvant mixture may be used, in which case the antigen and adjuvant are incorporated into the composition at the same time. An "antigen/adjuvant mixture" refers to an embodiment in which the antigen and adjuvant are in the same diluent at least prior to incorporation into the composition. The antigen and adjuvant in an antigen/adjuvant mixture may, but need not necessarily be chemically linked, such as by covalent bonding.

In some embodiments, the carrier comprising a continuous phase of a hydrophobic substance may itself have adjuvanting-activity. Incomplete Freund's adjuvant and Montanide® ISA 51 VG, are examples of a hydrophobic carrier with adjuvanting effect. As used herein and in the claims, when the term "adjuvant" is used, this is intended to indicate the presence of an adjuvant in addition to any adjuvanting activity provided by the carrier comprising a continuous phase of a hydrophobic substance.

Mode of Administration

Methods of the invention comprise the combined administration of an agent that interferes with DNA replication and a vaccine comprising at least one survivin antigen.

For improving the efficacy of the vaccine, embodiments of the methods of the invention comprise the administration of at least two doses of the agent that interferes with DNA replication before the first administration of the vaccine. In conjunction with these embodiments, the agent may additionally be administered to the subject at any other time before, during or after the course of treatment with the vaccine, so long as at least two doses are administrated prior to a first administration of the vaccine.

As used herein, the terms "combination", "co-administration", or "combined administration" or the like are meant to encompass administration of the agent that interferes with DNA replication and the vaccine to a single patient, and are intended to include instances where the agent and vaccine are not necessarily administered by the same route of administration or at the same time. For example, the agent that interferes with DNA replication and the vaccine may be for separate, sequential or alternating administration.

As used herein, the expression "at least two doses" is intended to encompass any number of doses that is greater than a single dose. In an embodiment, the at least two doses includes between 2-50 doses, more particularly between 2-28 doses, and more particularly between 2-14 doses. In an embodiment, the at least two doses is 2, 3, 4, 5, 6, 7, 8, 9, 10, 11, 12, 13 or 14 doses. The at least two doses may be separated by any suitable amount of time. In a particular embodiment, the at least two doses comprises 2 doses daily for a period of one week, totalling 14 doses.

The agent that interferes with DNA replication is typically administered in an amount sufficient to provide an immune-modulating effect. As used herein, the expression "immune-modulating effect" refers to the ability of the agent that interferes with DNA replication to alter (modulate) one or more aspects of the immune system and/or cells of the immune system. In an embodiment, the "amount sufficient to provide an immune-modulating effect" is an amount of the agent that is capable of selectively affecting DNA replication in cells the immune system. For example, the amount of agent may be an amount sufficient to selectively target rapidly dividing cells of the immune system to cause programmed cell death. This amount may also be described as a dose that is "non-chemotherapeutic", as defined herein.

The "amount sufficient to provide an immune-modulating effect" may interchangeably be referred to herein as a "low dose" amount. Thus, the methods of the invention preferably involve the use of a low dose of an agent that interferes with DNA replication in combination with the vaccine. As relates to a particular embodiment of the invention where the agent that interferes with DNA replication is the alkylating agent cyclophosphamide, the expression "low dose" typically refers to a dose of cyclophosphamide that is less than 300 mg/m$^2$, such as for example 100-300 mg/m$^2$. In terms of daily administration, a "low dose" of cyclophosphamide is typically between about 25-300 mg/day, and preferably 50-150 mg/day. Particularly suitable is a daily dosage amount of 100 mg of cyclophosphamide. Also particularly suitable is administering about 50 mg of cyclophosphamide per dose. The "low dose" amounts of other agents that interfere with DNA replication, as encompassed herein, would be known to those skilled in the art, or could be determined by routine skill.

The methods of the invention involve administering at least two doses of an agent that interferes with DNA replication, and then subsequently administering a vaccine of the invention. By "subsequently administering", it is meant that the administration of the agent that interferes with DNA replication starts before the first administration of the vaccine (e.g. at least two doses of agent are given to the subject before the vaccine). However, as described herein, the administering of the subject with the agent that interferes with DNA replication may continue after administration with the vaccine begins. In alternate embodiments, the administration of the agent that interferes with DNA replication stops before the first administration of the vaccine.

In the methods of the invention, the first dose of an agent that interferes with DNA replication precedes any treatment of the subject with the vaccine. In an embodiment, the minimum amount of time separating the first administration of the agent that interferes with DNA replication and the first administration of the vaccine may be any amount of time sufficient to provide an immune-modulating effect. As the skilled person will appreciate, the amount of time sufficient to provide an immune-modulating effect may be dependent on many variables and may not be the same for individual patients.

In some embodiments, the first dose of an agent that interferes with DNA replication is administered at least 12 hours before the first administration of the vaccine, and preferably at least two, four or six days before the first vaccination. In a further embodiment, the first dose of the agent that interferes with DNA replication may be provided about 1, 2, 3, 4, 5, 6, 7, 8, 9, 10, 11, 12, 13 or 14 days, or more, before the first administration of the vaccine. In a particular embodiment, the first administration of the agent that interferes with DNA replication occurs 1-4 days prior to the first administration of the vaccine. Particularly suitable is a first administration of the agent that interferes with DNA replication about one week before the first administration of the vaccine.

After the first dose with the agent that interferes with DNA replication, subsequent doses may be administered at any desired interval of time between doses, so long as at least two doses of the agent are administered before the first administration of the vaccine. The dosing with the agent that interferes with DNA replication may be stopped before, during or after the course of treatment with the vaccine.

In an embodiment, the first dose is followed by one or more maintenance doses. As used herein, the term "maintenance dose" is meant to encompass a dose of the agent that interferes with DNA replication that is given at such an interval and/or amount so as to maintain a sufficient amount of the agent, and/or its active metabolites, in the body of the subject (e.g. avoid total systemic clearance thereof of the agent and/or its active metabolites). By providing a maintenance dose, it may be possible to prolong and/or maintain the immune-modulating effect of the agent that interferes with DNA replication for an extended period of time before, during and/or after the course of administration with the vaccine.

In an embodiment, for maintaining the immune-modulating effect, the agent that interferes with DNA replication may be administered 1, 2, 3, 4 or 5 times daily, or more, so long as low dose administration is maintained (e.g. the multiple smaller doses add up to the desired daily low dose). A single dose (i.e. administration) of the agent that interferes with DNA replication may be given at a single point in time, such as for example a pill that is swallowed. Alternatively, a single dose of the agent that interferes with DNA replication may be given over a short continuous period, such as for example by drip intravenous.

For embodiments of the invention where the agent that interferes with DNA replication is cyclophosphamide, it may be appropriate to provide a maintenance dose, for example, every 6-18 hours. The skilled person in the art would know or could determine, by routine skill, the appropriate interval for maintenance doses of cyclophosphamide, as well as for other agents that interfere with DNA replication as encompassed herein.

In a particular embodiment, the agent that interferes with DNA replication is administered for a period of at least two consecutive days prior to the first administration of the vaccine. On these days, the agent that interferes with DNA replication may be administered to the subject at least 1, 2, 3 or 4 times daily, or any desired number of times to provide the daily low dose amount of the agent.

In another embodiment, the agent that interferes with DNA replication is administered for a period of about one week prior to the first administration of the vaccine. Multiple doses may be provided during this one week period. In exemplary embodiments, the agent that interferes with DNA replication may be administered on every day, on every second day, or at any suitable interval for providing the described maintenance dose. For example, a particular embodiment of the method of the invention comprises administering the agent twice daily for a period of about one week prior to administering the vaccine.

In the methods of the invention, there may be a break in treatment with the agent that interferes with DNA replication before the first administration of the vaccine. In such embodiments, administration of the agent that interferes with DNA replication may be permanently or temporarily stopped before the first administration of the vaccine. The period of time between the last dose of the agent that interferes with DNA replication and the first dose of the vaccine may be any suitable period of time so long as the subject still obtains an immune-modulating benefit from the agent. For example, and without limitation, the administration of the agent that interferes with DNA replication may be stopped at the same time that the first dose of vaccine is administered or at any time up to about one week before the first dose of the vaccine. For example, and without limitation, administration of the agent that interferes with DNA replication may be stopped at about 6, 12, 18, 24, 36, 48, 60 or 72 hours, or more, before the first dose of the vaccine. In a particular embodiment, administration of the agent that interferes with DNA replication is stopped about 2, 4 or 7 days before the first dose of the vaccine.

In an alternate embodiment, treatment of the subject with the agent that interferes with DNA replication continues throughout the course of treatment with the vaccine, with or without intermittent breaks in the administration of the agent. In further embodiments, treatment with the agent that interferes with DNA replication may continue after vaccination ceases.

Thus, in an embodiment, the agent that interferes with DNA replication may be administered during the period before each administration with the vaccine. Alternatively, the agent that interferes with DNA replication may only be administered during the period before the first administration with the vaccine.

As described herein, treatment with the agent that interferes with DNA replication may be continued after the first administration with the vaccine. In an embodiment, administration of the agent that interferes with DNA replication is continued on a daily basis, with or without intermittent breaks, throughout the course of treatment with the vaccine. Therefore, in some embodiments, the agent will be administered prior to and during the treatment with the vaccine. In such instances, once administration of the vaccine begins, it is possible for the agent that interferes with DNA replication to be administered at the same time as the vaccine, immediately sequentially, or at different times in the day. When the agent that interferes with DNA replication is administered at the same time as the vaccine, it may be included in the vaccine composition of the invention as a single composition or administered in a separate composition.

Alternatively, administration of the agent that interferes with DNA replication may be suspended during the days when the vaccine is administered. Therefore, regimens of the present invention may include taking a break in the administration of the agent that interferes with DNA replication during the course of administration of the vaccine.

The embodiments described herein for administering the agent that interferes with DNA replication prior to the first administration of the vaccine apply also to the administration of the agent after the first administration of the vaccine (e.g. before each subsequent administration of the vaccine).

As a particularly suitable embodiment, the method of the invention comprises metronomic treatment of the subject with the agent that interferes with DNA replication. For purposes of the present invention, "metronomic treatment", "metronomic regimen" or "metronomic dosing" or the like, is meant to refer to a frequent administration of a lower than normal dose amount of the agent that interferes with DNA replication. As used herein, the term "normal dose amount" may refer, for example and without limitation, to either: (i) the established maximum tolerated dose (MTD) or standard dose via a traditional dosing schedule, or (ii) in instances where a low dose single bolus amount has been established for a particular agent that interferes with DNA replication, than to that low dose amount.

In metronomic dosing, the same, lower, or higher cumulative dose over a certain time period as would be administered via a traditional dosing schedule may ultimately be administered. In a particularly suitable embodiment, this is achieved by extending the time frame during which the dosing is conducted and/or increasing the frequency of administrations, while decreasing the amount administered as compared to the normal dose amount. For example, where a low dose amount of 300 mg/m$^2$ of an agent that interferes with DNA replication is typically administered (e.g. by single bolus injection), a metronomic regimen may comprise administering the same amount over a period of several days by administering frequent low doses. By this approach, metronomic dosing may be used, for example, to provide the maintenance doses as described herein.

In an embodiment of the methods of the present invention, metronomic treatment with the agent that interferes with DNA replication is intended to encompass a daily low dose administration of the agent over a certain period of time, such as for example a period of 2, 3, 4, 5, 6 or 7, or more, consecutive days. During these days of metronomic dosing, the agent that interferes with DNA replication may be provided at frequent regular intervals or varying intervals. For example, in an embodiment, a dose of the agent that interferes with DNA replication may be administered every 1, 2, 3, 4, 6, 8, 12 or 24 hours. In another embodiment, a dose of the agent that interferes with DNA replication may be administered every 2, 3, or 4 days.

In some embodiments of the methods of the present invention, there may be breaks or gaps in the periods of metronomic treatment with the agent that interferes with DNA replication. In this manner, metronomic treatment with the agent that interferes with DNA replication may occur in a cyclic fashion, alternating between on and off periods of administration. Particularly suitable are intervals where the agent that interferes with DNA replication is administered to the subject daily on alternating weekly intervals. For instance, a one week period of administration of the agent that interferes with DNA replication is followed by a one week suspension of treatment, and the cycle repeats.

In an embodiment therefore, the methods of the invention comprise administering the agent that interferes with DNA replication to the subject daily for a period of one week every second week. In a particular aspect of this embodiment, the administration of the agent that interferes with DNA replication begins about one week before the first administration of the vaccine.

As relates to the vaccine of the invention, in some embodiments it may be particularly suitable to administer the vaccine to the subject at an interval of once every week, once every two weeks or once every three weeks, preferably once every three weeks. The frequency and duration of the administration of the vaccine may however be adjusted as desired for any given subject, and may be more or less frequent than once every week, once every two weeks or once every three weeks. The interval between the administrations may also not be constant during the course of treatment with the vaccine. In the methods of the invention, the vaccine may be administered to the subject 1, 2, 3, 4, 5, 6, 7, 8, 9, 10 or more times. It will be understood that treatment with the vaccine may be continued for an indefinite period depending on how the treatment of the cancer in the subject is progressing.

In an embodiment of the methods of the invention, the agent that interferes with DNA replication may be administered as a priming agent during the intermittent period before the each administration of the vaccine.

In a particular embodiment, a method of the invention comprising the combination of an agent that interferes with DNA replication and a survivin vaccine will involve the vaccine being administered to the subject at an interval of once every three weeks (e.g. Day 0, 21, 42, 63, 84, etc) with the first administration the agent that interferes with DNA replication beginning about one week before (e.g. Day −7) the first vaccine administration and the continuing daily (e.g. metronomic) on alternating weekly intervals. A treatment regime such as this is shown in FIG. 1.

As the skilled person will appreciate, the frequency and duration of the administration of the agent that interferes with DNA replication and the vaccine may be adjusted as desired for any given subject. Factors that may be taken into account include, e.g.: the nature of the one or more survivin antigens in the vaccine; the type of cancer; the age, physical condition, body weight, sex and diet of the subject; and other clinical factors.

The agent that interferes with DNA replication may be administered by any suitable delivery means and any suitable route of administration. In an embodiment, the agent that interferes with DNA replication is administered orally, such as in the form of a pill, tablet or capsule. In an alternate embodiment, the agent is administered by injection (e.g. intravenous). In a particular embodiment of the methods of the invention, the agent is cyclophosphamide and it is administered orally.

The vaccine of the invention as described herein may be formulated in a form that is suitable for oral, nasal, rectal or parenteral administration. Parenteral administration includes intravenous, intraperitoneal, intradermal, subcutaneous, intramuscular, transepithelial, intrapulmonary, intrathecal, and topical modes of administration. In embodiments where the vaccine is formulated as a composition comprising the one or more survivin antigens, liposomes and a carrier comprising a continuous phase of a hydrophobic substance, a particularly suitable route of administration may be injection (e.g. intradermal, intramuscular or subcutaneous) so as to achieve a depot effect at the site of injection. The vaccine and the agent that interferes with DNA replication are not necessarily administered by the same route of administration or at the same time.

In a particular embodiment of the methods of the invention, the agent that interferes with DNA replication is an alkylating agent, such as for example cyclophosphamide.

Treatment Indications

As described herein, the methods of the present invention relate to the treatment of cancer. Cancers that may be capable of being treated and/or prevented by the methods of the invention may include, for example, any cancer that expresses survivin or that over-expresses survivin as compared to normal cells.

In an embodiment, cancers that may be capable of being treated by the methods of the invention include, without limitation, carcinoma, adenocarcinoma, lymphoma, leukemia, sarcoma, blastoma, myeloma, and germ cell tumors. In an embodiment, the cancer is in the form of a solid tumor. Without limitation, particularly suitable embodiments include glioblastoma, multiple myeloma, ovarian cancer, fallopian tube cancer, or peritoneal cancer.

In some embodiments, the subject may have undergone surgery to remove a large bulk of the tumor, and the methods of the invention may be applied before and/or after excision of the bulk of the tumour. In other embodiments, the subject may have been given radiation therapy, chemotherapy or some other non-surgical treatment to control or kill cancerous or malignant cells, and the methods of the invention may be applied prior to or subsequent to these therapies. In certain embodiments, the cancer is at an advanced stage.

As used herein, the terms "tumor", "tumor cells", "cancer" and "cancer cells", (used interchangeably) refer to cells that exhibit abnormal growth, characterized by a significant loss of control of cell proliferation or cells that have been immortalized. The term "cancer" or "tumor" includes metastatic as well as non-metastatic cancer or tumors. A cancer may be diagnosed using criteria generally accepted in the art, including the presence of a malignant tumor.

"Treating" or "treatment of", or "preventing" or "prevention of", as referred to herein refers to an approach for obtaining beneficial or desired results, including clinical results. Beneficial or desired clinical results can include, but are not limited to, alleviation or amelioration of one or more symptoms or conditions, diminishment of extent of disease, stabilisation of the state of disease, prevention of development of disease, prevention of spread of disease, delay or slowing of disease progression, delay or slowing of disease onset, conferring protective immunity against a disease-causing agent and amelioration or palliation of the disease state. "Treating" or "preventing" can also mean prolonging survival of a patient beyond that expected in the absence of treatment and can also mean inhibiting the progression of disease temporarily, although more preferably, it involves preventing the occurrence of disease such as by preventing infection in a subject. "Treating" or "preventing" may also refer to a reduction in the size of the tumor mass.

In treating and/or preventing cancer, the methods of the invention may be used to "improve the efficacy of the vaccine", as this expression is described herein. This may involve improving the efficacy of the vaccine in inducing either or both of a cell-mediated immune response or a humoral immune response. This may also involve reducing tumor-induced immune suppression.

As used herein, "inducing" or "to induce" an immune response is to elicit, improve and/or potentiate an immune response. Inducing an immune response encompasses instances where the immune response is enhanced, elevated, improved or strengthened to the benefit of the subject relative to the prior immune response status, for example, before the application of the method of the invention.

As used herein, the term "cell-mediated immune response" refers to an increase in the amount of antigen-specific cytotoxic T-lymphocytes, macrophages, natural killer cells, or cytokines in the body of a subject in response to introduction of the antigen into the body of the subject.

Cell-mediated immunity is an immune response that does not involve antibodies but rather involves the activation of macrophages and natural killer cells, the production of antigen-specific cytotoxic T lymphocytes and the release of various cytokines in response to an antigen. Cytotoxic T lymphocytes are a sub-group of T lymphocytes (a type of white blood cell) which are capable of inducing the death of infected somatic or tumor cells; they kill cells that are infected with viruses (or other pathogens), or are otherwise damaged or dysfunctional.

Most cytotoxic T cells express T-cell receptors that can recognise a specific peptide antigen bound to Class I MHC molecules. These CTLs also express CD8 (CD8+ T cells), which is attracted to portions of the Class I MHC molecule. This affinity keeps the CTL and the target cell bound closely together during antigen-specific activation.

Cellular immunity protects the body by, for example, activating antigen-specific cytotoxic T-lymphocytes (e.g. antigen-specific CD8+ T cells) that are able to lyse body cells displaying epitopes of foreign antigen on their surface, such as virus-infected cells, cells with intracellular bacteria, and cancer cells displaying tumor antigens; activating macrophages and natural killer cells, enabling them to destroy intracellular pathogens; and stimulating cells to secrete a variety of cytokines that influence the function of other cells involved in adaptive immune responses and innate immune responses.

Cellular immunity is an important component of adaptive immune response and following recognition of antigen by cells through their interaction with antigen-presenting cells such as dendritic cells, B lymphocytes and to a lesser extent, macrophages, protects the body by various mechanisms such as:
1. activating antigen-specific cytotoxic T-lymphocytes that are able to induce apoptosis in body cells displaying epitopes of foreign antigen on their surface, such as virus-infected cells, cells with intracellular bacteria, and cancer cells displaying tumor antigens;
2. activating macrophages and natural killer cells, enabling them to destroy intracellular pathogens; and
3. stimulating cells to secrete a variety of cytokines that influence the function of other cells involved in adaptive immune responses and innate immune responses.

Cell-mediated immunity is most effective in removing virus-infected cells, but also participates in defending against fungi, protozoans, cancers, and intracellular bacteria. It also plays a major role in transplant rejection.

Since cell mediated immunity involves the participation of various cell types and is mediated by different mechanisms, several methods could be used to demonstrate the induction or improved efficacy of immunity following application of the methods of the invention. These could be broadly classified into detection of: i) specific antigen presenting cells; ii) specific effector cells and their functions and iii) release of soluble mediators such as cytokines.

i) Antigen presenting cells: Dendritic cells and B-cells (and to a lesser extent macrophages) are equipped with special immuno-stimulatory receptors that allow for enhanced activation of T cells, and are termed professional antigen presenting cells (APC). These immuno-stimulatory molecules (also called as co-stimulatory molecules) are up-regulated on these cells following infection or vaccination, during the process of antigen presentation to effector cells such as CD4+ and CD8+ cytotoxic T cells. Such co-stimulatory molecules (such as CD80, CD86, MHC class I or MHC class II) can be detected by using flow cytometry with fluorochrome-conjugated antibodies directed against these molecules along with antibodies that specifically identify APC (such as CD11c for dendritic cells).

ii) Cytotoxic T cells: (also known as Tc, killer T cell, or cytotoxic T-lymphocyte (CTL)) are a sub-group of T cells which induce the death of cells that are infected with viruses (and other pathogens), or expressing tumor antigens. These CTLs directly attack other cells carrying certain foreign or abnormal molecules on their surface. The ability of such cellular cytotoxicity can be detected using in vitro cytolytic assays (chromium release assay). Thus, induction of adaptive cellular immunity can be demonstrated by the presence of such cytotoxic T cells, wherein, when antigen loaded target cells are lysed by specific CTLs that are generated in vivo following vaccination or infection.

Naive cytotoxic T cells are activated when their T-cell receptor (TCR) strongly interacts with a peptide-bound MHC class I molecule. This affinity depends on the type and orientation of the antigen/MHC complex, and is what keeps the CTL and infected cell bound together. Once activated the CTL undergoes a process called clonal expansion in which it gains functionality, and divides rapidly, to produce an army of "armed"-effector cells. Activated CTL will then travel throughout the body in search of cells bearing that unique MHC Class I+peptide. This could be used to identify such CTLs in vitro by using peptide-MHC Class I tetramers in flow cytometric assays.

When exposed to these infected or dysfunctional somatic cells, effector CTL release perforin and granulysin: cytotoxins which form pores in the target cell's plasma membrane, allowing ions and water to flow into the infected cell, and causing it to burst or lyse. CTL release granzyme, a serine protease that enters cells via pores to induce apoptosis (cell death). Release of these molecules from CTL can be used as a measure of successful induction of cellular immune response following vaccination. This can be done by enzyme linked immunosorbant assay (ELISA) or enzyme linked immunospot assay (ELISPOT) where CTLs can be quantitatively measured. Since CTLs are also capable of producing important cytokines such as IFN-γ, quantitative measurement of IFN-γ-producing CD8 cells can be achieved by ELISPOT and by flowcytometric measurement of intracellular IFN-γ in these cells.

CD4+ "helper" T-cells: CD4+ lymphocytes, or helper T cells, are immune response mediators, and play an important role in establishing and maximizing the capabilities of the adaptive immune response. These cells have no cytotoxic or phagocytic activity; and cannot kill infected cells or clear pathogens, but, in essence "manage" the immune response, by directing other cells to perform these tasks. Two types of effector CD4+ T-helper cell responses can be induced by a professional APC, designated Th1 and Th2, each designed to eliminate different types of pathogens.

Helper T cells express T-cell receptors (TCR) that recognize antigen bound to Class II MHC molecules. The activation of a naive helper T-cell causes it to release cytokines, which influences the activity of many cell types, including the APC that activated it. Helper T-cells require a much milder activation stimulus than cytotoxic T-cells. Helper T-cells can provide extra signals that "help" activate cytotoxic cells. Two types of effector CD4+ T-helper cell responses can be induced by a professional APC, designated Th1 and Th2, each designed to eliminate different types of pathogens. The two Th cell populations differ in the pattern of the effector proteins (cytokines) produced. In general, Th1 cells assist the cellular immune response by activation of macrophages and cytotoxic T-cells; whereas Th2 cells promote the humoral immune response by stimulation of B-cells for conversion into plasma cells and by formation of antibodies. For example, a response regulated by Th1 cells may induce IgG2a and IgG2b in mouse (IgGI and IgG3 in humans) and favor a cell mediated immune response to an antigen. If the IgG response to an antigen is regulated by Th2 type cells, it may predominantly enhance the production of IgGI in mouse (IgG2 in humans). The measure of cytokines associated with Th1 or Th2 responses will give a measure of successful vaccination. This can be achieved by specific ELISA designed for Th1-cytokines such as IFN-γ, IL-2, IL-12, TNF-α and others, or Th2-cytokines such as IL-4, IL-5, IL10 among others.

iii) Measurement of cytokines: released from regional lymph nodes gives a good indication of successful immunization. As a result of antigen presentation and maturation of APC and immune effector cells such as CD4+ and CD8+ T cells, several cytokines are released by lymph node cells. By culturing these LNC in vitro in the presence of antigen, antigen-specific immune response can be detected by measuring release if certain important cytokines such as IFN-γ, IL-2, IL-12, TNF-α and GM-CSF. This could be done by ELISA using culture supernatants and recombinant cytokines as standards.

Successful immunization may be determined in a number of ways known to the skilled person including, but not limited to, hemagglutination inhibition (HAIJ and serum neutralization inhibition assays to detect functional antibodies; challenge studies, in which vaccinated subjects are challenged with the associated pathogen to determine the efficacy of the vaccination; and the use of fluorescence activated cell sorting (FACS) to determine the population of cells that express a specific cell surface marker, e.g. in the identification of activated or memory lymphocytes. A skilled person may also determine if the methods of the invention improved the efficacy of a cell mediated immune response using other known methods. See, for example, Current Protocols in Immunology Coligan et al., ed. (Wiley Interscience, 2007).

In some embodiments, the methods of the invention may also be used to treat cancer by inducing a humoral immune response or by improving the efficacy of the vaccine in inducing a humoral immune response. Such embodiments may have particular application in instances where the vaccine of the invention includes an additional antigen as described herein, other than a survivin antigen. These methods may involve the treatment of cancer by inducing both a cell-mediated immune response and a humoral immune response.

A humoral immune response, as opposed to cell-mediated immunity, is mediated by secreted antibodies which are produced in the cells of the B lymphocyte lineage (B cells). Such secreted antibodies bind to antigens, such as for example those on the surfaces of foreign substances and/or pathogens (e.g. viruses, bacteria, etc.) and flag them for destruction.

An "antibody" is a protein comprising one or more polypeptides substantially or partially encoded by immunoglobulin genes or fragments of immunoglobulin genes. The recognized immunoglobulin genes include the κ, λ, α, γ, δ, ε and μ constant region genes, as well as myriad immunoglobulin variable region genes. Light chains are classified as either κ or λ. Heavy chains are classified as γ, μ, α, δ, or ε, which in turn define the immunoglobulin classes, IgG, IgM, IgA, IgD and IgE, respectively. A typical immunoglobulin (antibody) structural unit comprises a protein containing four polypeptides. Each antibody structural unit is composed of two identical pairs of polypeptide chains, each having one "light" and one "heavy" chain. The N-terminus of each chain defines a variable region primarily responsible for antigen recognition. Antibody structural units (e.g. of the IgA and IgM classes) may also assemble into oligomeric forms with each other and additional polypeptide chains, for example as IgM pentamers in association with the J-chain polypeptide.

Antibodies are the antigen-specific glycoprotein products of a subset of white blood cells called B lymphocytes (B cells). Engagement of antigen with antibody expressed on the surface of B cells can induce an antibody response comprising stimulation of B cells to become activated, to undergo mitosis and to terminally differentiate into plasma cells, which are specialized for synthesis and secretion of antigen-specific antibody.

B cells are the sole producers of antibodies during an immune response and are thus a key element to effective humoral immunity. In addition to producing large amounts of antibodies, B cells also act as antigen-presenting cells and can present antigen to T cells, such as T-helper CD4 or cytotoxic CD8, thus propagating the immune response. B cells, as well as T cells, are part of the adaptive immune response which may assist in vaccine efficacy. During an active immune response, induced either by vaccination or natural infection, antigen-specific B cells are activated and clonally expand. During expansion, B cells evolve to have higher affinity for the epitope. Proliferation of B cells can be induced indirectly by activated T-helper cells, and also directly through stimulation of receptors, such as the toll-like receptors (TLRs).

Antigen presenting cells, such as dendritic cells and B cells, are drawn to vaccination sites and can interact with antigens and adjuvants contained in the vaccine. The adjuvant stimulates the cells to become activated and the antigen provides the blueprint for the target. Different types of adjuvants provide different stimulation signals to cells. For example, polyI:C polynucleotide (a TLR3 agonist) can activate dendritic cells, but not B cells. Adjuvants such as Pam3Cys, Pam2Cys and FSL-1 are especially adept at activating and initiating proliferation of B cells, which is expected to facilitate the production of an antibody response (Moyle et al., *Curr Med Chem*, 2008; So., *J Immunol*, 2012).

As used herein, the term "antibody response" refers to an increase in the amount of antigen-specific antibodies in the body of a subject in response to introduction of the antigen into the body of the subject.

One method of evaluating an antibody response is to measure the titers of antibodies reactive with a particular antigen. This may be performed using a variety of methods known in the art such as enzyme-linked immunosorbent assay (ELISA) of antibody-containing substances obtained from animals. For example, the titers of serum antibodies which bind to a particular antigen may be determined in a subject both before and after exposure to the antigen. A statistically significant increase in the titer of antigen-specific antibodies following exposure to the antigen would indicate the subject had mounted an antibody response to the antigen.

Other assays that may be used to detect the presence of an antigen-specific antibody include, without limitation, immunological assays (e.g. radioimmunoassay (RIA)), immunoprecipitation assays, and protein blot (e.g. Western blot) assays; and neutralization assays (e.g., neutralization of viral infectivity in an in vitro or in vivo assay).

The methods of the invention, by improving the efficacy of the vaccine in inducing a humoral immune response, may be capable of treating and/or preventing cancer.

A humoral immune response is the main mechanism for effective infectious disease vaccines. However, a humoral immune response can also be useful for combating cancer. Complementing a cancer vaccine, that is designed to produce a cytotoxic CD8+ T cell response that can recognize and destroy cancer cells, a B cell mediated response may target cancer cells through other mechanisms which may in some instances cooperate with a cytotoxic CD8+ T cell for maximum benefit. Examples of mechanisms of B cell mediated (e.g. humoral immune response mediated) anti-tumor responses include, without limitation: 1) Antibodies produced by B cells that bind to surface antigens found on tumor cells or other cells that influence tumorigenesis. Such antibodies can, for example. induce killing of target cells through antibody-dependant cell-mediated cytotoxicity (ADCC) or complement fixation, potentially resulting in the release of additional antigens that can be recognized by the immune system; 2) Antibodies that bind to receptors on tumor cells to block their stimulation and in effect neutralize their effects; 3) Antibodies that bind to factors released by or associated with tumor or tumor-associated cells to modulate a signaling or cellular pathway that supports cancer; and 4) Antibodies that bind to intracellular targets and mediate anti-tumor activity through a currently unknown mechanism.

The subject to be treated by the methods of the invention may be any vertebrate, preferably a mammal, more preferably a human.

Kits and Reagents

For practicing the methods of the present invention, the compositions as described herein may optionally be provided to a user as a kit. For example, a kit of the invention contains one or more components of the compositions of the invention. The kit can further comprise one or more additional reagents, packaging material, containers for holding the components of the kit, and an instruction set or user manual detailing preferred methods of using the kit components.

In a particular embodiment, the vaccine of the invention (e.g. DPX-Survivac) is supplied as a kit containing two containers. Container 1, for example, may comprise the lyophilized adjuvant system (e.g. liposomes), survivin antigens and adjuvant. Container 2, for example, may contain the oil component (Montanide® ISA51 VG) alone. An appropriate volume (0.1 or 0.5 mL) of the reconstituted vaccine may be injected subcutaneously.

In a embodiment, the kit may additionally contain an agent that interferes with DNA replication. The agent that interferes with DNA replication may be included in the kit with a third container, or the agent may be included in container 1 or container 2, as described above. In a particular embodiment, the agent that interferes with DNA replication that is included in the kit is an alkylating agent, such as for example, cyclophosphamide.

Embodiments of the Invention

Particular embodiments of the invention include, without limitation, the following:

(1) A method for improving the efficacy of a vaccine in the treatment of cancer in a subject, said method comprising, consisting of or consisting essentially of:

(i) administering to the subject at least two doses of an agent that interferes with DNA replication in an amount sufficient to provide an immune-modulating effect; and (ii) subsequently administering to the subject a therapeutically effective amount of the vaccine, wherein the vaccine comprises at least one survivin antigen.

(2) The method according to paragraph (1) comprising administering a first dose of the agent to the subject at least two days prior to administering the vaccine, and preferably at least four days prior to administering the vaccine.

(3) The method according to paragraph (1) comprising administering a first dose of the agent to the subject about one week prior to administering the vaccine.

(4) The method according to any one of paragraphs (1) to (3) comprising administering the agent for a period of at least two consecutive days.

(5) The method according to any one of paragraphs (1) to (4) comprising administering to the subject a first dose of the agent, followed by one or more maintenance doses of the agent.

(6) The method according to any one of paragraphs (1) to (5) comprising administering the agent to the subject at least 1, 2, 3 or 4 times daily prior to administering the vaccine.

(7) The method according to any one of paragraphs (1) to (6) comprising administering the agent twice daily for a period of about one week prior to administering the vaccine.

(8) The method according to any one of paragraphs (1) to (7), wherein the administering of the subject with the agent is stopped prior to administering the vaccine.

(9) The method according to any one of paragraphs (1) to (7), wherein the administering of the subject with the agent continues during the course of administering the vaccine.

(10) The method according to any one of paragraphs (1) to (9) comprising administering the vaccine to the subject about once every three weeks.

(11) The method according to any one of paragraphs (1) to (10) comprising administering the vaccine to the subject 2, 3, 4 or more times.

(12) The method according to any one of paragraphs (1) to (11) comprising administering the agent that interferes with DNA replication to the subject in a metronomic regimen.

(13) The method according to paragraph (12), wherein the metronomic regimen comprises administering the agent to the subject daily for a period of about one week every second week.

(14) The method according to paragraph (13) comprising administering the agent to the subject beginning about one week before administering a first dose of the vaccine, and comprising administering the vaccine to the subject about once every three weeks.

(15) The method according to any one of paragraphs (1) to (14), wherein the survivin antigen is a peptide antigen or a nucleic acid encoding an antigen.

(16) The method according to any one of paragraphs (1) to (15), wherein the survivin antigen is a peptide antigen comprising, consisting of or consisting essentially of an amino acid sequence from the survivin protein (SEQ ID NO: 11) that is capable of eliciting a cytotoxic T-lymphocyte (CTL) response in the subject, or a nucleic acid molecule encoding said peptide antigen.

(17) The method according to any one of paragraphs (1) to (16), wherein the survivin antigen is a peptide antigen comprising, consisting of or consisting essentially of the amino acid sequence FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); and LPPAWQPFL (SEQ ID NO: 8), or any combination thereof; or a nucleic acid molecule encoding said peptide antigen.

(18) The method according to any one of paragraphs (1) to (14), wherein the at least one survivin antigen comprises, consists of or consists essentially of a mixture of five peptide antigens comprising the amino acid sequence FTELTLGEF (SEQ ID NO: 2); LMLGEFLKL (SEQ ID NO: 4); RISTFKNWPK (SEQ ID NO: 6); STFKNWPFL (SEQ ID NO: 7) or LPPAWQPFL (SEQ ID NO: 8).

(19) The method according to any one of paragraphs (1) to (18), wherein the agent that interferes with DNA replication is capable of selectively targeting rapidly dividing cells of the immune system and causing programmed cell death.

(20) The method according to any one of paragraphs (1) to (19), wherein the agent that interferes with DNA replication is an alkylating agent.

(21) The method according to paragraph 20, wherein the alkylating agent is a nitrogen mustard alkylating agent.

(22) The method according to paragraph (21), wherein the nitrogen mustard alkylating agent is cyclophosphamide.

(23) The method according to paragraph (22), wherein the amount sufficient to provide an immune-modulating effect is about 25-300 mg/day, preferably about 50-100 mg/day, and more preferably about 100 mg/day of cyclophosphamide.

(24) The method according to paragraphs (22) or (23), wherein the amount sufficient to provide an immune-modulating effect is about 50 mg of cyclophosphamide per dose.

(25) The method according to any one of paragraphs (22) to (24) comprising orally administering the cyclophosphamide to the subject.

(26) The method according to any one of paragraphs (1) to (25) comprising administering the vaccine to the subject by injection, such as by subcutaneous injection.

(27) The method according to any one of paragraphs (1) to (26), wherein the vaccine is a composition comprising, consisting of or consisting essentially of the at least one survivin antigen, liposomes, and a carrier comprising a continuous phase of a hydrophobic substance.

(28) The method according to paragraph (27), wherein the composition further comprises a T-helper epitope.

(29) The method according to paragraph (28), wherein the T-helper epitope is a peptide comprising, consisting of or consisting essentially of the amino acid sequence AQYIKANSKFIGITEL (SEQ ID NO: 9).

(30) The method according to any one of paragraphs (27) to (29), wherein the composition further comprises an adjuvant.

(31) The method according to paragraph (30), wherein the adjuvant is a polyI:C polynucleotide.

(32) The method according to any one of paragraphs (27) to (31), wherein the carrier is a hydrophobic substance such as a vegetable oil, nut oil or mineral oil.

(33) The method according to any one of paragraphs (27) to (31), wherein the carrier is mineral oil or is a mannide oleate in mineral oil solution, for example Montanide® ISA 51.

(34) The method according to any one of paragraphs (1) to (33), wherein the agent improves the efficacy of the vaccine by directly enhancing the immune response against the antigen, such as by increasing the activity or number of antigen-specific $CD8^+$ T cells.

(35) The method according to paragraph (34), wherein increasing the activity or number of antigen-specific CD8+ T cells involves an enrichment of antigen-specific $CD8^+$ T cells due to a relative decrease in total CD8+ T cells.

(36) The method according to any one of paragraphs (1) to (33), wherein the agent improves the efficacy of the vaccine by reducing the number or activity of suppressive immune cells, for example $CD4^+FoxP3^+$ regulatory T cells (Tregs), myeloid-derived suppressor cells (MDSCs), and/or $CD19^+CD1d^+CD5^+$ B cells (Bregs).

(37) The method according to any one of paragraphs (1) to (36), wherein the cancer is a subcutaneous solid tumor.

(38) The method according to any one of paragraphs (1) to (36), wherein the cancer is ovarian cancer, fallopian tube cancer or peritoneal cancer.

(39) The method according to any one of paragraphs (1) to (38), wherein the subject is a human.

(40) Use of an agent that interferes with DNA replication in combination with a vaccine comprising, consisting of or consisting essentially of at least one survivin antigen for improving the efficacy of the vaccine in the treatment of cancer, wherein at least two doses of the agent are for administration prior to the vaccine.

(41) Combination of an agent that interferes with DNA replication and a vaccine comprising, consisting of or consisting essentially of at least one survivin antigen for use in a method according to any one of paragraphs (1) to (39).

(42) Composition as described herein for use in a method according to any one of paragraphs (1) to (39).

The invention is further illustrated by the following non-limiting examples.

EXAMPLES

Example 1

A phase I study conducted in the United States (IND #14731) and Canada (CTA-A #155301) examined the safety and immune potency of DPX-Survivac in combination with cyclophosphamide in ovarian cancer patients.

DPX-Survivac is a candidate anti-cancer immunotherapeutic vaccine that contains one decapeptide and four nonapeptides derived from the protein sequence of survivin, with different HLA restrictions (HLA-A1, A2, A3, A24 and B7). Specifically, DPX-Survivac comprises five synthetic survivin peptide antigens having the amino acid sequences: FTELTLGEF (SEQ ID NO: 2), LMLGEFLKL (SEQ ID NO: 4), RISTFKNWPK (SEQ ID NO: 6), STFKNWPFL (SEQ ID NO: 7), and LPPAWQPFL (SEQ ID NO: 8); a universal T-helper epitope from tetanus toxoid (AQYIKANSKFIGITEL; SEQ ID NO: 9; a polyI:C polynucleotide adjuvant; liposomes consisting of DOPC and cholesterol; and the hydrophobic carrier Montanide® ISA 51 VG. The DPX-Survivac vaccine is designed to target survivin.

In the clinical study, 18 of 19 advanced ovarian cancer patients treated with platinum chemotherapy and showing no disease progression completed their vaccine therapy. Cohort A (6 pts) received three 0.5 mL vaccine injections 3 weeks apart; Cohort B and Cohort C (6 pts each) received three 0.1 mL or 0.5 mL vaccine injections, respectively, in combination with metronomic low dose oral cyclophosphamide. The clinical trial was conducted in accordance with the schedule shown in FIG. 1.

Adverse events were assessed using CTCAE v4.0. Blood was collected to study immune function and vaccine-induced T cell immunity (analyses performed by (i) ELISPOT, (ii) tetramer analysis and (iii) multi-parametric Intracellular cytokine staining). Repeated measures of immunity by ELISPOT at baseline and after 1, 2 and 3 injections were analyzed statistically using a general linear model.

(i) IFN-γ ELISPOT Assay for Detecting Functional Antigen-Specific PBMC

Frozen PBMC samples taken from clinical trial subjects were tested in the IFN-γ ELISPOT assay for the recall response to the specified test antigens. Thawed PBMC was stimulated with a pool of five survivin peptides and with the corresponding peptide(s) depending on the HLA-type of the subject. The responses to the antigens, negative control (cells in medium alone) and the positive control (PHA) were tested in duplicate wells. The antigens were tested at a concentration of 50 and 5 µg/ml to test dose dependency in addition to antigen-specificity. The PBMC clinical samples were plated at a concentration of 300,000 cells/well of 96 well ELSPOT plate along with sex matched PBMC from healthy control subject.

On day 1, plates were coated with 80 µl/well of first antibody diluted in PBS and the plates are refrigerated overnight in humidified box. On day 2, plates were washed 3× with PBS, 200 µl/well; excess PBS was removed by flicking the plates. 100 µl/well of the antigen(s) desired for T cell activation were added followed by 100 µl/well of test or control PBMC. Cells were incubated at 37° C. in humidified incubator for 24 hours for IFN-γ □secretion. Until this step all steps were performed under sterile condition. On Day 3, plates were washed 3× with PBS, 3× with PBS-TWEEN followed by addition of 80 µl/well of biotinylated secondary antibody in PBS-TWEEN-BSA and incubated overnight in refrigerator, in a humidified box. On day 4, plates were washed 3× with PBS-TWEEN, 200 µl/well, followed by adding 100 µl/well of tertiary detection reagent in PBS-BSA and incubated at room temperature for 2 hours. Plates were washed 3× with PBS-TWEEN and 3× with PBS, and 200 µl/well freshly prepared development solution will be added. Spot development was monitored at room temperature, typically for 10-60 minutes, carefully checking for lack of color development in the medium control wells and appearance of spots in antigen containing wells. The reaction was stopped by rinsing plates with tap water while flicking it. Plates were air dried overnight and stored at room temperature in the dark. ELISPOT plates were then scanned using an automated plate analyzer. Raw SFU counts were processed and summarized to obtain data on antigen-induced IFN-γ secretion by PBMC.

ELISPOT Materials:
Solutions:
1. PBS: sterile tissue culture-tested
2. 0.05% PBS-TWEEN: e.g., 500 µl Tween-20 in 1 L PBS
3. 1% PBS-BSA: e.g., 10 g BSA-Fraction V in 1 L PBS (1%)
4. 1% PBS-TWEEN-BSA: e.g., 1 L PBS-TWEEN plus 10 g BSA-Fraction V Medium:
Serum-free test medium supplemented with 1% L-glutamine.

Test Cells:
Human PBMC (Frozen in liquid nitrogen and thawed) 3×10⁵ cells per well of the test samples
Incubator: 37° C., humidified, 7% $CO_2$
AEC Solution:
100 mg AEC (3-amino-9-ethyl carbazole) in 10 ml DMF (N,N,Dimethylformamide)
Prepared in a glass tube, in a fume hood
AEC Buffer (0.1 M Acetate):
148 ml 0.2 M acetic acid (11.55 ml glacial acidic acid per L $H_2O$) plus
352 ml 0.2 M sodium acetate (27.2 g per L $H_2O$).
Bring up to 1 L with $H_2O$. Adjust to pH 5.0
Development Solution (to be Used Immediately):
800 µl AEC solution plus 24 ml AEC buffer. Filter 0.45 µm. Add 12 µl $H_2O_2$ (30%)

(ii) Antigen-Specific CD8+ T Cells Using MHC-Multimers (Tetramers)

MHC-multimer reagents help to identify antigen-specific CD8+ T cells generated in vaccinated subjects. These specific T cells express TCR which can recognize and bind to the peptide(s) used in the vaccine (when conjugated with MHC molecules). Immune response to vaccine peptides is reflected by the expansion of antigen-specific T cells. Such CD8+ T cells were measured directly ex vivo soon after thawing of the PBMC and after in vitro stimulation and cytokine-induced expansion in the presence of the survivin peptide antigens included in DPX-Survivac.

MHC-multimer reagents, such as tetramers (Beckman Coulter or TC Metrix, for HLA-A1, A2 and A3; TC Metrix for HLA-A24 and B7) were used for specific detection of vaccine induced CD8+ T cells. For both ex vivo and in vitro activated PBMC, control PBMC and control MHC-multimer reagents were used in the assay. Known CMV+ healthy donor PBMC along with CMV-specific MHC-multimer were used as positive control and HIV-specific reagent will be used as negative control for inter- and intra-assay validation and quality assurance.

A. Ex Vivo Detection of Antigen-Specific CD8+ T Cells:

Ex vivo staining for specific T cells in the blood was performed in 10-color flow cytometry, along with regulatory T cell (Treg) phenotyping. The staining cocktail included: Live/dead, CD3, CD4, CD8, CD45RA, CD27, CD25, Ki67, Foxp3 and the tetramer reagent matching the subject's HLA type. The assay qualification tests to verify that cell permeabilization for intracellular Foxp3 staining for Treg cells does not interfere with cell surface staining were completed successfully. The ex vivo tetramer analysis consisted of staining thawed and overnight rested PBMC using the antibody cocktail (as shown above) and tetramer reagent for flow cytometry. Briefly, thawed PBMC were first stained with the tetramer reagent at 4° C. for 30 minutes and washed in IMF buffer (PBS+0.5% BSA+0.01% sodium azide). Cells were then stained with antibody mixture, containing different fluorochrome-conjugated antibodies as phenotypic markers, for 30 minutes at 4° C. Cells were then washed and fixed in 1% paraformaldehyde and used for flow cytometry. For detecting the levels of B cells, separate tubes were used to stain the cells with CD19 antibody, since cell permeabilization for Foxp3 adversely affects CD19 antibody binding.

B. In Vitro Activation of PBMC to Detect Specific CD8+ T Cells:

For in vitro activation and expansion of antigen-specific T cells, PBMC from the same cells thawed and used for ex vivo analysis were cultured in the presence of survivin peptide antigen and cytokines (IL-2 and IL-15) for 10 days. Briefly, viability of thawed and overnight rested cells was performed and PBMC were suspended at 1×10⁶ cells/ml in completed RPMI-1640 medium supplemented with 10% heat inactivated FCS, 2 mM L-glutamine, 50 µM (3-mercaptoethanol, 100 U/ml penicillin and 100 µg/ml streptomycin, 10 IU/ml human recombinant IL-2 and 10 ng/ml human recombinant IL-15. In a 24 well plate 1×10⁶ cells/well were placed in 1.0 ml medium and the cells were either left untreated or stimulated with appropriate HLA-matched survivin peptide at 5 µg/ml final concentration. Cells were incubated at 37° C. humidified incubator with 5% $CO_2$ supply. On day 3, 6 and 8, medium was carefully aspirated without disturbing the cells taking care to leave some medium so that cells do not go dry. Appropriate volume (1.0 ml) of pre-warmed complete RPMI medium with cytokines (10 IU/ml IL-2 and 10 ng/ml IL-15) was added. On day 10, all the cells were collected and washed once with plain RPMI medium, once with IMF buffer and used for tetramer staining (5 color) according to the protocol: live/dead, CD3, CD8, CD45RA and one or two MHC-multimer reagents, depending on the subjects' HLA-type. Since there could be cross reactivity of HLA-A2 tetramer with PBMC from either A1 or A3 subjects, cells from the subjects with the latter two HLA-types were also tested with the reagent designed for HLA-A2. In parallel with patient PBMC, known CMV+ healthy control PBMC were also activated with CEF peptide pool to generate positive control sample that could be used for intra- and inter-assay comparisons. Following staining, cells were fixed in 1% paraformaldehyde for flow cytometry.

(iii) Multi-Parametric Flow Cytometry (ICS)

Multi-parametric flow cytometry assay is considered very informative because it allows the simultaneous detection of multiple cytokines/chemokines (IFN-γ, TNF-α, IL-2, IL-4, IL-17 and others) and phenotypic and/or functional markers (CD3, CD4, CD8, CD19, CD27, CD45RA, CD107a Granzyme-B, CCR7, etc). Also, it has been shown that multi-functional T cells (secreting multiple cytokines) are associated with protective type 1 immune response and detecting such cells in enrolled subjects is likely to reflect immune-efficacy of the vaccine administered.

ICS assay was performed as a 12 color flow cytometry that included: live/dead marker, CD3, CD4, CD8, CD45RA, CD27 (as subset and memory differentiation markers) along with IFN-γ, TNF-γ, IL-2, IL-17, Granzyme-B, and CD107a (for cytokines and other functional markers). Selection of phenotypic markers used in the assay allows identification of specific effector/central memory T cells which are likely to respond to the vaccine antigens in the assay. Conditions of cell stimulation included: non-stimulated, PMA/Ionomycin positive controls, pooled survivin peptides that are included in the vaccine, HLA-matched peptide for a given subject and CEF (CMV/EBV/FLU) peptide pool stimulation of control PBMC. In addition to patient PBMC, known HLA-A2 healthy donors PBMC were used as an internal control for quality assurance. Briefly, $10^6$ PBMC, after overnight resting, were stimulated for 1 hour with individual peptides and pools of peptides in the presence of anti-CD107a antibodies. Final peptide pool or individual peptide concentrations used for stimulation were 1 μg/mL. Protein secretion inhibitors (GolgiPlug™/GolgiStop™, BD Bioscience) were added after 1 hour of stimulation, and cells were incubated for an additional 5 hours at 37° C. and 5% $CO_2$. Following in vitro stimulation, cells were washed and surface stained for 30 minutes at 4° C. (CD8, CD27 CD3, CD4 and CD45RA and viability marker) followed by intracellular staining (IFN-γ, TNF-α, IL-17, IL-2) of fixed/permeabilized cells for 30 minutes at 4° C. Labeled cells will be acquired on a LSR II flow cytometer using the FACS DiVa software (BD Bioscience) and analyzed using FlowJo software. Multifunctional cytokine analysis will be performed after stringent gating of each cytokine positive population. In addition, SPICE, a data mining software application, was used to analyze large FlowJo data sets from polychromatic flow cytometry and to organize the normalized data graphically.

Results:

Antigen specific immune responses, as assessed by the production of IFN-γ in ELISPOT analysis, were generally established with one or two vaccinations and increased or maintained with boosters (FIGS. 2-4). A dose response was observed, with cohort C patients producing significantly higher magnitude responses (cohort C versus cohort B, P=0.013). Low dose cyclophosphamide significantly enhanced the 0.5 ml dose (cohort C versus cohort A, P=0.015). These results demonstrate that the combination of immune modulation with low dose cyclophosphamide in combination with DPX-Survivac generated the strongest immune responses. Patients in cohort C were able to mount an immune response with as little as one dose of vaccine following as little as one week of prior low dose cyclophosphamide administration. The responses achieved in cohort C after one, two or three doses (as high as 2309, 1911 and 2517 spots per $10^6$ PBMC) could only be achieved with the combination of survivin vaccine and low dose cyclophosphamide.

Figure 5:
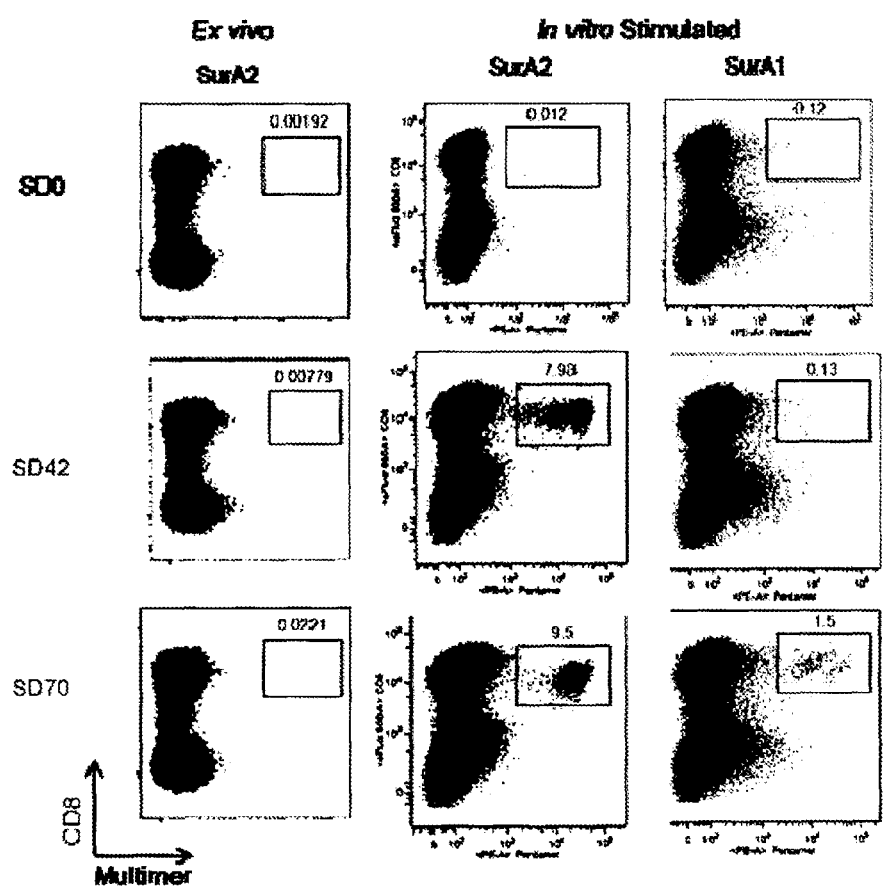
FIG. 5 illustrates the MHC-Multimer staining results from representative subject 02-04. Peripheral blood mononuclear cells were tested for the presence of peptide-specific CD8+ T cells by their ability to bind MHC-multimer reagents (tetramers) designed using the DPX-Survivac peptide and the corresponding MHC molecule. The assay was performed either on non-stimulated PBMC (ex vivo) or stimulated 10 days in vitro in the presence of HLA-matched survivin peptide(s). Irrelevant MHC-multimer based on HIV peptide served as negative control. Figures shown depict the percent CD8+ T cells in post-vaccination PBMC samples, binding specifically to MHC-multimer reagents. Specific T cells were detected using flow cytometry where PBMC were gated on CD3+ live cells, in order to show cells double positive for CD8+ and the tetramer binding.
Figure 6:
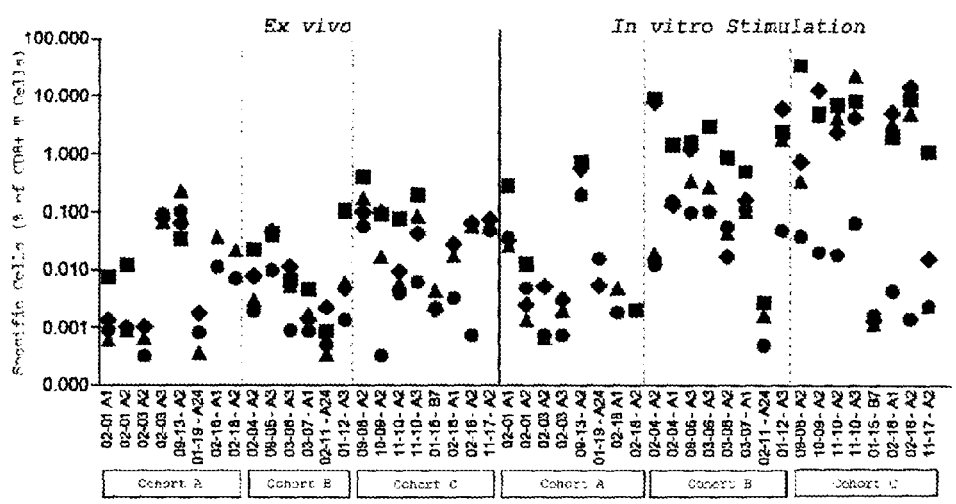
FIG. 6: Detection of a DPX-Survivac induced increase in CD8+ T cells in the peripheral blood mononuclear cells (PBMC) from vaccinated ovarian cancer patients. Subject PBMC were tested for the presence of peptide-specific CD8+ T cells by their ability to bind MHC-multimer reagents (tetramers) designed using the DPX-Survivac peptide and the corresponding MHC molecule. The assay was performed either on non-stimulated PBMC (ex vivo) or stimulated 10 days in vitro in the presence of HLA-matched survivin peptide(s). Data presented represent the percentage of CD8+ T cells in the peripheral blood of individual subjects at baseline (circles), after 1 dose (triangles), 2 doses (diamonds), and 3 doses (squares).

The higher magnitude of immune responses generated by the survivin vaccine in cohorts B and C were characterised by the detection of circulating antigen-specific T cell responses and a polyfunctional T cell response profile in the blood (FIGS. 5 and 6). In some subjects, these circulating antigen-specific CD8+ T cells can be detected ex vivo by tetramer staining, and such specific T cells can also be expanded further by stimulation with HLA-matched peptide antigen(s) in vitro. 10 of 12 subjects receiving the DPX-Survivac combination therapy were evaluable by tetramer staining; all 10 showed strong evidence of survivin-specific CD8+ T cell induction following one or two vaccinations with DPX-Survivac. Importantly, the CD8+ T cell responses were maintained with booster vaccinations. The activation and maintenance of these specific immune cells is of particular interest in immunotherapy since CD8+ T cells are implicated in identifying cancer cells, infiltrating tumors and killing cancer targets. The strongest responses were observed in cohort C by tetramer analysis, confirming the results obtained by ELISPOT. The majority of patients in cohort C had tetramer positivity above 1% of total CD8+ T cells (with in vitro stimulation) and reaching as high as 22% of total CD8+ T cells. In contrast, the highest tetramer positivity recorded in cohort A was below 1% of total CD8+ T cells (0.7%). This demonstrates that the combination of low dose cyclophosphamide and vaccine generated significantly higher antigen specific immune responses.

Several subjects treated with DPX-Survivac also showed the induction of polyfunctional CD8+ T cells which are indicative of protective immune response. Two subjects each, out of six, in each of cohorts A and B and 5 subjects out of 6 in cohort C were positive for multiple-cytokine secreting CD8+ T cells. Most of these CD8 cells were of central memory phenotype indicating previous antigen exposure and induction of lasting immune response against survivin in treated subjects. Results from representative subjects positive for multi-cytokine positivity following treatment are shown in Table 4.

TABLE 4

| Subject Id | Cytokines | Pre-Treatment | Post-Treatment |
|---|---|---|---|
| 09-08 | IFN-γ + TNF-α + IL2 | ND* | + |
| | IFN-γ + TNF-α | ND* | − |
| | TNF-α + IL2 | ND* | + |
| | IFN-γ + IL2 | ND* | + |
| 10-09 | IFN-γ + TNF-α + IL2 | − | + |
| | IFN-γ + TNF-α | − | + |
| | TNF-α + IL2 | − | + |
| | IFN-γ + IL2 | − | − |
| 11-10 | IFN-γ + TNF-α + IL2 | − | + |
| | IFN-γ + TNF-α | − | − |

TABLE 4-continued

| Subject Id | Cytokines | Pre-Treatment | Post-Treatment |
|---|---|---|---|
| | TNF-α + IL2 | − | + |
| | IFN-γ + IL2 | − | − |
| 02-16 | IFN-γ + TNF-α + IL2 | − | + |
| | IFN-γ + TNF-α | − | + |
| | TNF-α + IL2 | − | + |
| | IFN-γ + IL2 | − | + |

The above table (Table 4) provides the ICS staining results from representative responders, subjects 09-08, 10-09, 11-10 and 02-16, showing multi-cytokine secreting central memory CD8 T cells. Peripheral blood mononuclear cells were tested for the presence of polyfunctional CD8+ T cells by intracellular cytokine staining (ICS). After short term (5 hour) stimulation with survivin peptides, cells were surface stained for phenotypic markers such as CD3, CD4, CD8, CD27, CD45RA, fixed, permeabilized and stained further for the presence of intracellular cytokines such as INF-γ, TNF-α and IL-2. Flow cytometry analysis using Flow-Jo software was used to detect single/multiple cytokine secreting central memory (CD27+CD45RA−) CD8+ T cells at baseline and post-vaccination time points, except for subject 09-08 with late differentiated CD8+ T cells (CD3+CD8+CD45RA+CD27−). (+) indicates detection of poly-functional T cells in post-treatment blood samples with a frequency range of >0.05% to >3.0% of memory CD8+ T cell subsets analyzed. (−) indicates absence of detectable poly-functional CD8 T cells. (*) not determined due to poor quality PBMC.

Example 2

Peripheral Blood Mononuclear Cells (PBMCs) from patients 02-04, 11-10, 02-16, 03-07, 09-08, 10-09 and 01-12 were collected on study day 70, 4 weeks after the third vaccination with DPX-Survivac, given in combination with metronomic cyclophosphamide as described. The exception is patient 09-08, where the sample analyzed was from study day 126, 12 weeks after third vaccination. The HLA haplotype of all patients was determined, and are shown in brackets along with patient ID numbers (see FIG. 7). The immune response in these patients was analyzed ex vivo using ELISPOT assay (FIG. 7; left panel) or in vitro tetramer analysis by flow cytometry (FIG. 7; right panel), following stimulation with pooled survivin peptides. In ELISPOT assay, patient PBMCs were stimulated with pooled peptides, representing either the modified peptides included in the vaccine DPX-Survivac (black bars; SurA1.T (SEQ ID NO: 2), SurA2.M (SEQ ID NO: 4), SurA3.K (SEQ ID NO: 6), as well as the unmodified SurA24 (SEQ ID NO: 7) and SurB7 (SEQ ID NO: 8) peptides), or a peptide pool substituting the modified peptides for the native peptides from survivin protein (white bars; SurA1 (SEQ ID NO: 1), SurA2 (SEQ ID NO: 3), SurA3 (SEQ ID NO: 5)).

Modified Peptides contained in DPX-Survivac are shown in Table 5:

TABLE 5

| Native Peptide | Native Peptide Sequence | Modified Peptide | Modified Peptide Sequence |
|---|---|---|---|
| SurA1 | FEELTLGEF (SEQ ID NO: 1) | SurA1.T | FTELTLGEF (SEQ ID NO: 2) |
| SurA2 | LTLGEFLKL (SEQ ID NO: 3) | SurA2.M | LMLGEFLKL (SEQ ID NO: 4) |
| SurA3 | RISTFKNWPF (SEQ ID NO: 5) | SurA3.K | RISTFKNWPK (SEQ ID NO: 6) |

For tetramer analysis, single peptide (native or modified) was used to stimulate PBMC in the presence of IL-2/IL-15 cytokines for 10 days and the frequency of antigen-specific T cells was detected using tetramer reagents designed based on modified peptide and corresponding HLA molecules. Patients are expected to generate immune responses to the peptides corresponding to their relevant HLA type (i.e., SurA1 to HLA-A1 SurA2 to HLA-A2 and SurA3 to HLA-A3). As demonstrated in FIG. 7, immune responses generated to the modified survivin peptides contained in DPX-Survivac demonstrate significant cross reactivity to the native peptides, as seen in both ELISPOT and tetramer analysis of post-vaccination blood samples. Hence, DPX-Survivac vaccine-induced CD8+ T cells are expected to target tumor cells expressing native peptides in conjunction with corresponding HLA molecules on the cell surface. Because of the observed immune cross-reactivity towards native survivin peptide sequences, it is expected that the inclusion of native peptides in a vaccines would produce an immune response that is capable of recognizing native sequences if present on cells targeted by the vaccine.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "carrying", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the invention disclosed and/or claimed herein.

---

The invention claimed is:

1. A method for improving the efficacy of a vaccine in the treatment of cancer in a subject, said method comprising:
   (i) administering to the subject cyclophosphamide in a metronomic regimen in an amount sufficient to provide an immune-modulating effect, wherein the metronomic regimen comprises a two week cycle, wherein cyclophosphamide is administered to the subject during the first week of said cycle, wherein cyclophosphamide is not administered to the subject during the second week of said cycle, and wherein said metronomic regimen comprises at least two cycles; and
   (ii) administering to the subject a therapeutically effective amount of the vaccine one week after beginning the cyclophosphamide metronomic regimen, wherein the vaccine comprises at least one survivin antigen.

2. The method according to claim 1 comprising administering the cyclophosphamide to the subject at least 1, 2, 3 or 4 times daily prior to administering the vaccine.

3. The method according to claim 1 comprising administering the cyclophosphamide twice daily prior to administering the vaccine.

4. The method according to claim 1 comprising administering the vaccine to the subject about once every three weeks, and administering the vaccine to the subject 2, 3, 4 or more times.

5. The method according to claim 1, wherein the survivin antigen is a peptide antigen or a nucleic acid encoding an antigen.

6. The method according to claim 5, wherein the survivin antigen is:
   a peptide antigen comprising an amino acid sequence from the survivin protein (SEQ ID NO: 11) that is capable of eliciting a cytotoxic T-lymphocyte (CTL) response in the subject, or a nucleic acid molecule encoding said peptide antigen;
   a peptide antigen comprising the amino acid sequence FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); LPPAWQPFL (SEQ ID NO: 8), or any combination thereof; or a nucleic acid molecule encoding said peptide antigen; or
   a mixture of five peptide antigens comprising the amino acid sequence FTELTLGEF (SEQ ID NO: 2); LMLGEFLKL (SEQ ID NO: 4); RISTFKNWPK (SEQ ID NO: 6); STFKNWPFL (SEQ ID NO: 7) or LPPAWQPFL (SEQ ID NO: 8).

7. The method according to claim 1, wherein the amount sufficient to provide an immune-modulating effect is about 25-300 mg/day of cyclophosphamide.

8. The method according to claim 1, wherein the amount sufficient to provide an immune-modulating effect is about 50 mg of cyclophosphamide per dose.

9. The method according to claim 1 comprising orally administering the cyclophosphamide to the subject and administering the vaccine to the subject by injection.

10. The method according to claim 1, wherein the vaccine is a composition comprising the at least one survivin antigen, liposomes, and a carrier comprising a continuous phase of a hydrophobic substance.

11. The method according to claim 10, wherein the composition further comprises a T-helper epitope.

12. The method according to claim 11, wherein the composition further comprises an adjuvant.

13. The method according to claim 10, wherein the carrier is a hydrophobic substance such as a vegetable oil, nut oil or mineral oil.

14. The method according to claim 12, wherein:
   the carrier is mineral oil or is a mannide oleate in mineral oil solution and/or
   the T-helper epitope is a peptide comprising the amino acid sequence AQYIKANSKFIGITEL (SEQ ID NO: 9); and/or
   the adjuvant is a polyI:C polynucleotide; and/or
   the survivin antigen is a peptide antigen comprising the amino acid sequence FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); LPPAWQPFL (SEQ ID NO: 8), or any combination thereof.

15. The method according to claim 1, wherein:
the agent improves the efficacy of the vaccine by directly enhancing the immune response against the antigen, such as by increasing the activity or number of antigen-specific CD8+ T cells and/or
the agent improves the efficacy of the vaccine by reducing the number or activity of suppressive immune cells, for example CD4+FoxP3+ regulatory T cells (Tregs), myeloid-derived suppressor cells (MDSCs), and/or CD19+CD1d+CD5+ B cells (Bregs).

16. The method according to claim 15, wherein increasing the activity or number of antigen-specific CD8+ T cells involves an enrichment of antigen-specific CD8+ T cells due to a relative decrease in total CD8+ T cells.

17. The method according to claim 1, wherein the cancer is a subcutaneous solid tumor, ovarian cancer, fallopian tube cancer or peritoneal cancer.

18. The method according to claim 1, wherein the subject is a human.

19. The method according to claim 1, wherein the amount sufficient to provide an immune-modulating effect is about 50-100 mg/day of cyclophosphamide.

20. The method according to claim 1, wherein the amount sufficient to provide an immune-modulating effect is about 100 mg/day of cyclophosphamide.

21. The method according to claim 6, wherein the survivin antigen is a peptide antigen comprising an amino acid sequence from the survivin protein (SEQ ID NO: 11) that is capable of eliciting a cytotoxic T-lymphocyte (CTL) response in the subject.

22. The method according to claim 6, wherein the survivin antigen is a peptide antigen comprising the amino acid sequence FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); LPPAWQPFL (SEQ ID NO: 8), or any combination thereof.

23. The method according to claim 6, wherein the survivin antigen is a mixture of five peptide antigens comprising the amino acid sequence FTELTLGEF (SEQ ID NO: 2); LMLGEFLKL (SEQ ID NO: 4); RISTFKNWPK (SEQ ID NO: 6); STFKNWPFL (SEQ ID NO: 7) and LPPAWQPFL (SEQ ID NO: 8).

24. The method according to claim 6, wherein the survivin antigen is a nucleic acid molecule encoding a peptide antigen comprising an amino acid sequence from the survivin protein (SEQ ID NO: 11) that is capable of eliciting a cytotoxic T-lymphocyte (CTL) response in the subject.

25. The method according to claim 6, wherein the survivin antigen is a nucleic acid molecule encoding a peptide antigen comprising the amino acid sequence FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); LPPAWQPFL (SEQ ID NO: 8), or any combination thereof.

26. The method according to claim 9, wherein the injection is a subcutaneous injection.

27. The method according to claim 12, wherein:
the carrier is mineral oil or is a mannide oleate in mineral oil solution; and/or
the T-helper epitope is a peptide comprising the amino acid sequence AQYIKANSKFIGITEL (SEQ ID NO: 9); and/or
the adjuvant is a polyI:C polynucleotide; and/or
the survivin antigen is a nucleic acid molecule encoding peptide antigen comprising the amino acid sequence FEELTLGEF (SEQ ID NO: 1); FTELTLGEF (SEQ ID NO: 2); LTLGEFLKL (SEQ ID NO: 3); LMLGEFLKL (SEQ ID NO: 4); RISTFKNWPF (SEQ ID NO: 5); RISTFKNWPK (SEQ ID NO: 6); STFKNWPFL (SEQ ID NO: 7); LPPAWQPFL (SEQ ID NO: 8), or any combination thereof.

28. The method according to claim 13, wherein the hydrophobic substance is mineral oil.

29. The method according to claim 17, wherein the cancer is ovarian cancer.

* * * * *